US011834448B2

(12) United States Patent
Li et al.

(10) Patent No.: US 11,834,448 B2
(45) Date of Patent: *Dec. 5, 2023

(54) 2-AMINO-QUINOLINE DERIVATIVES

(71) Applicant: BIRDIE BIOPHARMACEUTICALS, INC., Grand Cayman (KY)

(72) Inventors: Lixin Li, Beijing (CN); Huiping Guan, Beijing (CN)

(73) Assignee: Birdie Biopharmaceuticals, Inc., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/315,156

(22) Filed: May 7, 2021

(65) Prior Publication Data

US 2021/0261548 A1   Aug. 26, 2021

Related U.S. Application Data

(62) Division of application No. 16/608,581, filed as application No. PCT/CN2018/084674 on Apr. 26, 2018, now Pat. No. 11,053,240.

(30) Foreign Application Priority Data

Apr. 27, 2017 (CN) .......................... 201710287322.2

(51) Int. Cl.
C07D 471/04 (2006.01)
C07D 498/16 (2006.01)

(52) U.S. Cl.
CPC ......... *C07D 471/04* (2013.01); *C07D 498/16* (2013.01)

(58) Field of Classification Search
CPC .................................................. C07D 471/04
See application file for complete search history.

(56) References Cited

U.S. PATENT DOCUMENTS

| | | |
|---|---|---|
| 4,689,338 A | 8/1987 | Gerster |
| 5,352,784 A | 10/1994 | Nikolaides |
| 5,389,640 A | 2/1995 | Gerster et al. |
| 5,482,936 A | 1/1996 | Lindstrom |
| 6,110,929 A | 8/2000 | Gerster et al. |
| 6,194,425 B1 | 2/2001 | Gerster et al. |
| 6,331,539 B1 | 12/2001 | Crooks et al. |
| 6,451,810 B1 | 9/2002 | Coleman et al. |
| 6,924,271 B2 | 8/2005 | Averett |
| 7,488,802 B2 | 2/2009 | Collins et al. |
| 7,576,068 B2 | 8/2009 | Averett |
| 7,943,743 B2 | 5/2011 | Korman et al. |
| 7,994,135 B2 | 8/2011 | Doronina et al. |
| 8,008,449 B2 | 8/2011 | Korman et al. |
| 8,067,546 B2 | 11/2011 | McDonagh et al. |
| 8,138,172 B2 | 3/2012 | Crook et al. |
| 8,246,968 B2 | 8/2012 | Zale et al. |
| 8,337,856 B2 | 12/2012 | Blattler et al. |
| 8,383,768 B2 | 2/2013 | Singh et al. |
| 8,552,154 B2 | 10/2013 | Freeman et al. |
| 8,575,180 B2 | 11/2013 | Kurimoto et al. |
| 8,663,643 B2 | 3/2014 | Berry et al. |
| 8,779,108 B2 | 7/2014 | Queva et al. |
| 8,951,528 B2 | 2/2015 | Stoermer et al. |
| 9,259,459 B2 | 2/2016 | Keler et al. |
| 9,308,253 B2 | 4/2016 | Kim et al. |
| 9,522,958 B2 | 12/2016 | Epstein et al. |
| 9,827,329 B2 | 11/2017 | Li |
| 9,878,052 B2 | 1/2018 | Li |
| 9,920,060 B2 | 3/2018 | Kawai et al. |
| 10,328,158 B2 | 6/2019 | Li |
| 10,548,985 B2 | 2/2020 | Li |
| 10,548,988 B2 | 2/2020 | Li |
| 10,660,971 B2 | 5/2020 | Li |
| 10,744,206 B2 | 8/2020 | Li |
| 10,780,180 B2 | 9/2020 | Li |
| 11,046,781 B2 | 6/2021 | Li |
| 11,053,240 B2 | 7/2021 | Li et al. |
| 11,130,812 B2 | 9/2021 | Li et al. |
| 11,136,397 B2 | 10/2021 | Li et al. |
| 11,220,552 B2 | 1/2022 | Li |
| 11,279,761 B2 | 3/2022 | Li |
| 2003/0119861 A1 | 6/2003 | Gerster |
| 2003/0139364 A1 | 7/2003 | Krieg et al. |
| 2004/0014779 A1 | 1/2004 | Gorden et al. |
| 2004/0162309 A1 | 8/2004 | Gorden et al. |
| 2005/0180983 A1 | 8/2005 | Keler et al. |
| 2005/0239735 A1 | 10/2005 | Miller et al. |

(Continued)

FOREIGN PATENT DOCUMENTS

| | | |
|---|---|---|
| AR | 086196 A1 | 11/2013 |
| EA | 200800781 | 8/2008 |

(Continued)

OTHER PUBLICATIONS

McMahon et al (2000).*
Pinedo et al. (2000).*
U.S. Appl. No. 17/315,162, filed Apr. 26, 2018.*
Burke et al., Design, synthesis, and biological evaluation of antibody-drug conjugates comprised of potent camptothecin analogues. Bioconjugate Chem, 20:1242-1250 (2009).
Guidance for Industry Estimating the Maximum Safe Starting Dose in Initial Clinical Trials for Therapeutics in Adult Healthy Volunteers. U.S. Dept. of Health and Human Services Food and Drug Administration Center for Drug Evaluation and Research (CDER) Jul. 2005, Pharmacology and Toxicology.

(Continued)

*Primary Examiner* — Paul V Ward
(74) *Attorney, Agent, or Firm* — K&L Gates LLP; Louis C. Cullman; Benjamin D. Heuberger

(57) ABSTRACT

Described herein are 2-amino-quinoline derivatives that are agonists of toll-like receptors 7 and 8 (TLR7/8), pharmaceutical compositions, and methods of use of the compounds and compositions to treat various diseases, such as viral, cancer, and allergic diseases, in need thereof by administering a therapeutically effective amount of a 2-amino-quinoline derivative.

44 Claims, No Drawings

(56) References Cited

U.S. PATENT DOCUMENTS

| | | |
|---|---|---|
| 2006/0110383 A1 | 5/2006 | Honjo et al. |
| 2006/0135459 A1 | 6/2006 | Epstein et al. |
| 2006/0142202 A1 | 6/2006 | Alkan et al. |
| 2006/0188913 A1 | 8/2006 | Krieg et al. |
| 2008/0025980 A1 | 1/2008 | Hardy et al. |
| 2008/0031887 A1 | 2/2008 | Lustgarten |
| 2009/0004194 A1 | 1/2009 | Kedl |
| 2009/0111756 A1 | 4/2009 | Doronina et al. |
| 2009/0123467 A1 | 5/2009 | Atul et al. |
| 2009/0182005 A1 | 7/2009 | Maus et al. |
| 2009/0202626 A1 | 8/2009 | Carson et al. |
| 2010/0143301 A1 | 6/2010 | Desai et al. |
| 2010/0256169 A1 | 10/2010 | Averett |
| 2011/0077263 A1 | 3/2011 | Kast et al. |
| 2011/0123629 A1 | 5/2011 | Pitcovski et al. |
| 2011/0195923 A1 | 8/2011 | Cherfils et al. |
| 2011/0274685 A1 | 11/2011 | Keler et al. |
| 2012/0027806 A1 | 2/2012 | Ilyinskii et al. |
| 2012/0039916 A1 | 2/2012 | Zurawski et al. |
| 2012/0219615 A1 | 8/2012 | Hershberg et al. |
| 2012/0231023 A1 | 9/2012 | Zurawski et al. |
| 2013/0022595 A1 | 1/2013 | Rotem-Yehudar et al. |
| 2013/0309250 A1 | 11/2013 | Cogswell et al. |
| 2014/0044738 A1 | 2/2014 | Langermann et al. |
| 2014/0088085 A1 | 3/2014 | Burgess et al. |
| 2015/0141625 A1 | 5/2015 | Stoermer et al. |
| 2015/0174268 A1 | 6/2015 | Li |
| 2015/0374815 A1 | 12/2015 | Kishimoto et al. |
| 2016/0324983 A1 | 11/2016 | Li |
| 2016/0339090 A1 | 11/2016 | Hacohen et al. |
| 2016/0375148 A1 | 12/2016 | Li |
| 2017/0028079 A1 | 2/2017 | Li |
| 2017/0056391 A1 | 3/2017 | Li |
| 2017/0114137 A1 | 4/2017 | Li |
| 2017/0128477 A1 | 5/2017 | Seong et al. |
| 2017/0290923 A1 | 12/2017 | Li |
| 2018/0110874 A1 | 4/2018 | Li |
| 2018/0134701 A1 | 5/2018 | David et al. |
| 2018/0148452 A1 | 5/2018 | Ding et al. |
| 2018/0177887 A1 | 6/2018 | Li |
| 2018/0177888 A1 | 6/2018 | Li |
| 2018/0346572 A1 | 12/2018 | Li |
| 2019/0016808 A1 | 1/2019 | Li |
| 2019/0016819 A1 | 1/2019 | Li |
| 2019/0048084 A1 | 2/2019 | Li |
| 2019/0099415 A1 | 4/2019 | Li |
| 2019/0269789 A1 | 9/2019 | Li |
| 2019/0269790 A1 | 9/2019 | Li |
| 2020/0155700 A1 | 5/2020 | Li |
| 2020/0179527 A1 | 6/2020 | Li |
| 2020/0345860 A1 | 7/2020 | Li |
| 2020/0246478 A1 | 8/2020 | Li |
| 2020/0276327 A1 | 9/2020 | Li |
| 2020/0353093 A1 | 11/2020 | Li |
| 2021/0214354 A1 | 7/2021 | Yang |
| 2021/0261549 A1 | 8/2021 | Li et al. |
| 2021/0330664 A1 | 10/2021 | Li |
| 2021/0347911 A1 | 11/2021 | Li |
| 2021/0363271 A1 | 11/2021 | Li |
| 2022/0016152 A1 | 1/2022 | Li et al. |
| 2022/0033503 A1 | 2/2022 | Li et al. |
| 2022/0089749 A1 | 3/2022 | Li |
| 2022/0175762 A1 | 6/2022 | Li |
| 2022/0204641 A1 | 6/2022 | Li |
| 2022/0251212 A1 | 8/2022 | Li |

FOREIGN PATENT DOCUMENTS

| | | |
|---|---|---|
| EP | 0145340 A2 | 6/1985 |
| JP | 2010-270129 | 12/2010 |
| RU | 2412942 C2 | 2/2011 |
| RU | 2426734 C2 | 8/2011 |
| RU | 2460728 C2 | 9/2012 |
| RU | 2475487 C2 | 2/2013 |
| WO | 2001/000244 A2 | 1/2001 |
| WO | 2001/034709 | 5/2001 |
| WO | 2002/046191 A2 | 6/2002 |
| WO | 2002/046192 | 6/2002 |
| WO | 2002/046194 | 6/2002 |
| WO | 2003/043572 A2 | 5/2003 |
| WO | 2003/050121 A1 | 6/2003 |
| WO | 2003/070234 A1 | 8/2003 |
| WO | 2004/029206 A2 | 4/2004 |
| WO | 2004/056875 | 7/2004 |
| WO | 2004/058759 A1 | 7/2004 |
| WO | 2004/062603 A2 | 7/2004 |
| WO | 2005/025583 A2 | 3/2005 |
| WO | 2005/032484 A2 | 4/2005 |
| WO | 2005/034979 A2 | 4/2005 |
| WO | 2005/079195 A2 | 9/2005 |
| WO | 2006/020266 A2 | 2/2006 |
| WO | 2006/071997 A2 | 7/2006 |
| WO | 2006/091720 A2 | 8/2006 |
| WO | 2006/091769 A1 | 8/2006 |
| WO | 2006/108627 A1 | 10/2006 |
| WO | 2006/116423 A2 | 11/2006 |
| WO | 2006/134423 | 12/2006 |
| WO | 2007/024612 | 3/2007 |
| WO | 2007/030642 A2 | 3/2007 |
| WO | 2007/040840 | 4/2007 |
| WO | 2007/103048 A2 | 9/2007 |
| WO | 2008/052187 A2 | 5/2008 |
| WO | 2008/079924 A1 | 7/2008 |
| WO | 2008/082601 A2 | 7/2008 |
| WO | 2008/097870 A2 | 8/2008 |
| WO | 2008/115319 A2 | 9/2008 |
| WO | 2009/018500 A1 | 2/2009 |
| WO | 2009/089900 A1 | 7/2009 |
| WO | 2009/093250 A2 | 7/2009 |
| WO | 2009/099650 A2 | 8/2009 |
| WO | 2010/132622 A2 | 11/2010 |
| WO | 2011/066389 A1 | 6/2011 |
| WO | 2011/084725 | 7/2011 |
| WO | 2011/084726 | 7/2011 |
| WO | 2012/078771 A1 | 6/2012 |
| WO | 2012/104344 A1 | 8/2012 |
| WO | 2012/143143 A1 | 10/2012 |
| WO | 2013/019906 A1 | 2/2013 |
| WO | 2013/022595 A1 | 2/2013 |
| WO | 2013/043647 A1 | 3/2013 |
| WO | 2013/063275 A1 | 5/2013 |
| WO | 2013/067597 A1 | 5/2013 |
| WO | 2013/0166110 A1 | 11/2013 |
| WO | 2014/012479 A1 | 1/2014 |
| WO | 2014/022758 A1 | 2/2014 |
| WO | 2014/032021 A1 | 2/2014 |
| WO | 2014/060112 A1 | 4/2014 |
| WO | 2014/060113 A1 | 4/2014 |
| WO | 2014/161887 | 10/2014 |
| WO | 2015/103987 A1 | 7/2015 |
| WO | 2015/103989 A1 | 7/2015 |
| WO | 2015/103990 A1 | 7/2015 |
| WO | 2016/004875 A1 | 1/2016 |
| WO | 2016/004876 A1 | 1/2016 |
| WO | 2016/034085 A1 | 3/2016 |
| WO | 2017/118405 A1 | 7/2017 |
| WO | 2017/118406 A1 | 7/2017 |
| WO | 2018/196823 A1 | 11/2018 |
| WO | 2018/232725 A1 | 12/2018 |
| WO | 2020/051356 A1 | 3/2020 |
| WO | 2020/139618 A1 | 7/2020 |
| WO | 2022/047083 A9 | 3/2022 |

OTHER PUBLICATIONS

Hamblett et al., Effects of drug loading on the antitumor activity of a monoclonal antibody drug conjugate. Clinical Cancer Research, 10:7063-7070 (2004).

Nakajiima et al., Mechanism of amide formation by carbodiimide for bioconjugation in aqueous media. Bioconjugate Chem., 6:123-130 (1995).

Molecular Probes, et al., Protein-Protein Crosslinking Kit, Catalog No. P6305 (2011).

(56) References Cited

OTHER PUBLICATIONS

Peine et al., Liposomal resiquimod for the treatment of Leishmania donovani infection. J Antimicrob Chemother, 69:168-175 (2014).
Sesay et al., Monoclonal antibody conjugation via chemical modification. BioPharm International, 16(12) (2003).
Agata et al., Expression of the PD-1 antigen on the surface of stimulated mouse T and B lymphocytes. Int. Immunol. 8(5):765-772 (1996).
Betting, et al., In vivo eradication of a rituximab-resistant human CD20+ B cell lymphoma by rituximab-CpG oligodeoxynucleotide conjugate is mediated by natural killer cells and complement. Blood (ASH Annual Meeting Abstracts), 114: Abstract 723 (2009).
Blencowe et al., Self-immolative linkers in polymeric delivery systems. Polym. Chem., 2:773-790 (2011).
Bonifaz, et al., Efficient targeting of protein antigen to the dendritic cell receptor DEC-205 in the steady state leads to antigen presentation on major histocompatibility complex class I products and peripheral CD8+ T cell tolerance. The Journal of Experimental Medicine, vol. 196, No. 12, pp. 1627-1638 (2002).
Braga et al., Crystal polymorphism and multiple crystal forms. Struct Bond, 132:25-50 (2009).
Butchar et al., TLR7/8 Agnosits overcome the suprresion of Fc gamma R activity in monocytes from chronic lymphocytic leukemia patients. Blood, vol. 120, No. 21, pp. 4595 (2012).
Carter, et al., Preferential induction of CD4+ T cell responses through in vivo targeting of antigen to dendritic cell-associated C-type lectin-1. The Journal of Immunology, vol. 177, No. 4, pp. 2276-2284 (2006).
Cherfils-Vicini et al., Triggering of TLR7 and TLR8 expressed by human lung cancer cells induces cell survival and chemoresistance. J. Clin. Investigation. 120(4):1285-1297 (2010).
Dummer et al., Imiquimod in basal cell carcinoma: How does it work? Br. J. Dermatol., 149(Suppl. 66):57-58 (2003).
Engel et al., The pharmacokinetics of Toll-like receptor agonists and the impact on the immune system. Expert Rev. Clin. Pharmacol., 4(2):275-289 (2011).
Extended European Search Report for European Patent Application No. 15818970.4 dated May 14, 2018.
Hofman et al., Phase I evaluation of intralesionally injected TLR9-agonist PF-3512676 in patients with basal cell carcinoma or metastatic melanoma. J. Immunother. 31:520-527 (2008).
Hurvitz et al., The potential for trastuzumab emtansine in human epidermal growth factor receptor 2 positive metastatic breast cancer: latest evidence and ongoing studies. Therapeutic Advances in Medical Oncology, 4(5):235-245 (2012).
International Search Report and Written Opinion for International Application No. PCT/CN2015/083583 filed on Jul. 8, 2015.
Berenbaum, M.C. Synergy, additivism and antagonism in immunosuppression. Clin. Exp. Immunol., 28, 1-18 (1977).
Wiesenthal, http://weisenthal.org/feedback, 2002.
Butchar et al., Reciprocal regulation of activating and inhibitory Fcgamma receptors by TLR7/8 activation: Implications for tumor immunotherapy. Clin. Cancer Res., 16(7): 2065-2075 (2010).
Hengge et al., Letter to the editor: Topical imiquimod to treat recurrent breast cancer. Breast Cancer Research and Treatment, 94:93-94 (2005).
Pinedo et al., Translational Research: The role of VEGF in tumor angiogenesis. The Oncologist, 5(suppl):1-2 (2000).
International Search Report and Written Opinion, dated Dec. 27, 2019, for International Patent Application Serial No. PCT/US2019/049784 filed on Sep. 5, 2019.
Lu et al., VTX-2337 is a novel TLR8 agonist that activates NK cells and augments ADCC. Clin. Cancer Res., 18(2):499-509 (2011).
Van Egmond et al., Cross-talk between pathogen recognizing Toll-like receptors and immunoglobulin Fc receptors in immunity. Immunological Reviews, 268(1):311-327 (2015).
Schneble et al., Breast cancer immunotherapy. Medica—A Journal of Clinical Medicine, 10(2):185-191 (2015).
Smorlesi et al., Imiquimod and S-27609 as adjuvants of DNA vaccination in a transgenic murine model of HER2/heu-positive mammary carcinoma. Gene Therapy, 12:1324-1332 (2005).
Tomai et al., Resiquimod and other immune response modifiers as vaccine adjuvants. Expert Rev. Vaccines 6 (5):835-847 (2007).
Eriksson et al., Gemcitabine reduces MDSCs tregs and TGFB. 1 while restoring the teff/treg ratio in patients with pancreatic cancer. J. Transl. Med., 14:282, 12 pp (2016).
Mcmahon et al., VEGF receptor signaling in tumor angiogenesis. The Oncologist, 5(suppl 1):3-10 (2000).
International Search Report and Written Opinion, dated Mar. 9, 2020, for International Patent Application Serial No. PCT/US2019/066796 filed on Dec. 17, 2019.
Dotan et al., Impact of Rituximab (Rituxan) on the treatment of B-cell non-hodgkin's lymphoma. P&T, 35(3):148-157 (2010).
Dovedi et al., Systemic delivery of a TLR7 agonist in combination with radiation primes durable antitumor immune responses in mouse models of lymphoma. Blood, 121(2):251-259 (2013).
Damiano et al., A Novel Toll-Like Receptor 9 Agonist Cooperates with Trastuzumab in Trastuzumab-Resistant Breast Tumors through Multiple Mechanisms of Action. Clinical Cancer Research, 15(22):6921-6930 (2009).
Shah et al., Toll-like receptor 2 Ligands Regulate Monocyte Fc gamma Receptor Expression and Function. J. Biol. Chem., 288(17)12345-12352 (2013).
Pirker et al., Cetuximab in non-small-cell lung cancer. Transl Lung Cancer Res 1(1): 54-60 (2012).
Schon et al., Review: TLR7 and TLR8 as targets in cancer therapy. Oncogene 27, 190-199 (2008).
U.S. Appl. No. 17/669,177, filed Feb. 10, 2022.
Berge et al., Review Article: Pharmaceutical Salts. J. Pharm. Sci., 66(1):1-19 (1977).
Byrn et al., Pharmaceutical Research, vol. 12, No. 7, pp. 945-954 (1996).
Meyer et al., Resiquimod, a topical drug for viral skin lesions and skin cancer. Expert Opinion on Investigational Drugs, vol. 22, Issue 1, pp. 149-159 (2013).
Caira, Crystalline polymorphism of organic compounds. Topics in Current Chemistry, Springer Verlag, Berlin/Heidelberg, 1998, vol. 198, pp. 163-208 (1998).
Caisova et al., Effective cancer immunotherapy based on combination of TLR agonists with stimulation of phagocytosis. International Immunopharmacology., 59:86-96 (2018).
International Search Report and Written Opinion, dated Feb. 3, 2022, for International Application Serial No. PCT/US2021/047826 filed Aug. 26, 2021.
Kukes, Clinical Pharmacokinetics: Theoretical, Applied, and Analytical Aspects, A Guide, Ed. (Chapter 11.2: Relationship between the Crystal Structure of the Substance, on the One Hand, and the Pharmacokinetics and Efficiency of the Medicine, on the Other, by I.G. Smirnova and V.V. Chistyakov) (2009). (Original and Translation enclosed).
Mathijssen et a., Flat-fixed dosing versus body surface area-based dosing of anticancer drugs in adults: Does it make a difference? the Oncologist, 12(8):913-923 (2007).
Balmana et al., BRCA in breast cancer: ESMO clinical recommendations. Annals of Oncology, 20 (Supplement 4):iv19-iv20 (2009).
Barnes, Sheri. A20: Modeling B cell lymphoma in mice. Covance by labcorp. Scientific Development (Oct. 2017).
Butte et al., Interaction of human PD-L1 and B7-1. Molecular Immunology, 45:3567-3572 (2008).
Campione et al., Lack of efficacy of imiquimod in patients with basal cell carcinoma previously treated with rituximab for B cell lymphoma. J. Medical Case Reports, 10(1):57-59 (2016).
Cang et al., Novel CD20 monoclonal antibodies for lymphoma therapy. Journal of Hematology & Oncology, 5:64, 9 pp (2012).
Coiffier et al., Rituximab (anti-CD20 monoclonal antibody) for the treatment of patients with relapsing or refractory aggressive lymphoma: a multicenter phase II study. Blood, vol. 92(6), pp. 1927-1932 (1998).
European Examination Report for Application No. 17735845.4 dated Nov. 9, 2020.

(56) References Cited

OTHER PUBLICATIONS

Extended European Search Report for European Patent Application No. 17914627.9 dated Nov. 18, 2020.
Gorden et al., Synthetic TLR agonists reveal functional differences between human TLR7 and TLR8. J Immunol, 174:1259-1268 (2005).
International Search Report and Written Opinion, dated Dec. 27, 2019, for International Application Serial No. PCT/US2019/049784 filed Sep. 5, 2019.
Johnston et al., The immunoreceptor TIGIT regulates antitumor and antiviral CD8+ T cell effector function. Cancer Cell 26, 923-937 (2014).
Kataja et al., Primary breast cancer: ESMO clinical recommedations for diagnosis, treatment and follow-up. Annals of Oncology, 20 (Supplement 4): iv10-iv14 (2009).
Kim et al., Establishment and characterization of BALB/c lymphoma lines with B cell properties. The Journal of Immunology, 122:549-554 (1979).
Lau et al., Tumour and host cell PD-L1 is required to mediate suppression of anti-tumor immunity in mice. Nat. Commun. 8, 14572, 11 pp. (2017).
Lee et al., Molecular basis for the immunostimulatory activity of guanine nucleoside analogs: Activation of Toll-like receptor 7. PNAS, vol. 100, No. 11, pp. 6646-6651 (2003).
Malm et al., Abstract 3976: PD-1 blockade combined with TEGVAX (TLR agonists-enhanced GVAX) can induce regression of established palpable tumors. Cancer Research, 73 (8 Supplment) abstract 3976 (2013).
Matin et al., Therapeutic targeting of Toll-like receptors in cutaneous disorders. Expert Opinion on Therapeutic Targets, vol. 19(12), pp. 1651-1663 (2015).
Mbow et al., Small molecule and biologic modulators of the immune response to hepatitis C virus. Mini-Reviews in Medicinal Chemistry, 6:527-531 (2006).
Nelson et al., Screening for breast cancer: an update for the U.S. preventive services task force. Ann. Intern Med., 151:727-737 (2009).
Parvinen et al., Primary non-hodgkin's lymphoma ('Reticulum Cell Sarcoma') of bone in adults. Acta Radiologica: Oncology, 22:6, 449-454 (1983).
Rituxan Prscribing Information. Revised Aug. 2020.
Schaer et al., The CDK4/6 inhibitor Abemaciclib induces a T cell inflamed tumor microenvironment and enhances the efficacy of PD-L1 checkpoint blockade. Cell Reports 22, 2978-2994 (2018).
Search results list for resiquimod | Cancer. ClinicalTrials.gov, accessed Apr. 16, 2021.
Shukla et al., Regioisomerism-dependent TLR7 agonism and antagonism in an imidazoquinoline. Bioorg. Med. Chem. Lett., 19:2211-2214 (2009).
Shukla et al., Structure-activity relationships in human toll-like receptor 7-active imidazoquinoline analogues. J. Med. Chem., vol. 53, No. 11, pp. 4450-4465 (2010).
Singaporean Written Opinion for Singaporean Patent Application No. 11201909325R dated Feb. 5, 2021.
Smits et al., The use of TLR7 and TLR8 ligands for the enhancement of cancer immunotherapy. The Oncologist, 13:859-875 (2008).
Third Party Observation submitted Aug. 27, 2019 for PCT International Patent Application Serial No. PCT/CN2018/084674 filed on Apr. 26, 2018.
U.S. Appl. No. 17/315,162, filed May 7, 2021.
U.S. Appl. No. 17/328,103, filed May 24, 2021.
U.S. Appl. No. 17/328,116, filed May 24, 2021.
U.S. Appl. No. 17/417,357, filed Jun. 22, 2021.
Extended European Search Report for European Patent Application No. 22151690.9 dated Apr. 28, 2022.
<https://en.wikipedia.org/wiki/Epidermal_growth_factor_receptor>, downloaded May 7, 2021 (in U.S. Appl. No. 16/068,338 in Non-Final Office Action dated May 11, 2021).
<https://en.wikipedia.org/wiki/Resiquimod>, downloaded May 7, 2021 (in U.S. Appl. No. 16/068,338 in Non-Final Office Action dated May 11, 2021).
Bastin et al., Salt selection and optimisation procedures for pharmaceutical new chemical entities. Organic Process Research & Development, 4(5):427-435 (2000).
Makkouk et al., The potential use of toll-like receptor (TLR) agonists and antagonists as prophylactic and/or therapeutc agents. Immunopharmacology and Immunotoxicology, vol. 31, No. 3, pp. 331-338 (2009).
Morissette et al., High-throughput crystallization: polymorphs, salts, co-crystals and solvates of pharmaceutical solids. Advanced Drug Delivery Reviews, 56:275-300 (2004).
Office Action, dated Aug. 19, 2020 for Russian Patent Application No. 2020102453 (Original and Translation enclosed).
Search Report for Russian Patent Application No. 2020102453 (Original and Translation enclosed).
Shi et al., Discovery of imidazoquinolines with Toll-like receptor 7/8 independent cytokine induction. ACS Medicinal Chemistry Letters, vol. 3, No. 6, pp. 501-504 (2012).
Supplementary European Search Report, dated Jul. 14, 2020, for European Application Serial No. 18792253.
Tanji et al., Structural reorganization of the toll-like receptor 8 dimer induced by agonistic ligands. Science, vol. 339, pp. 1426-1429 (2013) (also includes supplementary materials).
Gandini et al., PD-L1 expression in cancer patients receiving anti PD-1/PD-L1 antibodies: A systematic review and meta-analysis. Critical Reviews in Oncology/Hematology 100, pp. 88-98 (2016).
International Search Report and Written Opinion, dated Aug. 12, 2020, for International Application Serial No. PCT/US2020/022575 filed Mar. 13, 2020.
Krishnan et al., PD-1 expression in T-cell lymphomas and reactive lymphoid entities: Potential overlap in staining patterns between lymphoma and viral lymphadenitis. Am. J. Surg. Pathol., vol. 34, No. 2, pp. 178-179 (2010).
Ma et al., The TLR7 agonists imiquimod and gardiquimod improve DC-based immunotherapy for melanoma in mice. Cellular and Molecular Immunology, 7, pp. 381-388 (2010).
Patnaik et al., Phase I study of MK-3475 (anti-PD-1 monoclonal antibody) in patients with advanced solid tumors. Journal of Clinical Oncology, vol. 30, No. 15, pp. 2512 (2012).
Sharpe et al., The diverse functions of the PD1 inhibitory pathway. Nature Reviews: Immunology, vol. 18, pp. 153-167 (2018).
Topalian et al., Safety, activity, and immune correlates of anti-PD-1 antibody in cancer. The New England Journal of Medicine, vol. 366, No. 26 (2012).
U.S. Appl. No. 17/405,680, filed Aug. 18, 2021.
U.S. Appl. No. 17/439,333, filed Sep. 14, 2021.
U.S. Appl. No. 17/478,153, filed Sep. 17, 2021.
U.S. Appl. No. 17/546,779, filed Dec. 9, 2021.
Vippagunta et al., Crystalline solids. Advanced Drug Delivery Reviews, 48:3-26 (2001).
West, Anthony. Solid State Chemistry and its Applications. Wiley, New York, 358 (1988).
Grosso et al., Association of tumor PD-L1 expression and immune biomarkers with clinical activity in patients (pts) with advanced solid tumors treated with nivolumab (anti-PD-1; BMS-936558; ONO-4538). J. Clin. Oncol., Jun. 1, 2013, vol. 31, No. 15.
Hamid et al., Safety and tumor responses with lambrolizumab (anti-PD-1) in melanoma. New Engl. J. Med., Jun. 2, 2013, vol. 369, No. 2, pp. 134-144.
Search results by the Chinese Patent Office for Chinese Patent Application No. CN201410325480 dated Dec. 21, 2018 (English translation included).
Singaporean Further Written Opinion for Singaporean Patent Application No. 11201700079V filed on Jul. 8, 2015, dated Mar. 20, 2019.
Roses et al., Differential production of IL-23 and IL-12 by myeloid-derived dendritic cells in response to TLR agonists. J. Immunol., 181:5120-5127 (2008).
Yrlid et al., Regulation of intestinal dendritic cell migration and activation by plasmacytoid dendritic cells, TNF-alpha and Type 1 IFNs after feeding a TLR7/8 ligand. J. Immunol., 176:5205-5212 (2006).

(56) References Cited

OTHER PUBLICATIONS

Pockros et al., Oral resiquimod in chronic HCV infection: Safety and efficacy in 2 placebo-controlled, double-blind phase IIa studies. Journal of Hepatology, 47:174-182 (2007).
Johnson et al., Impact of NRAS Mutations for Patients with Advanced Melanoma Treated with Immune Therapies. Cancer Immunol Res, 3(3):288-295 (2015).
Lee et al., Resiquimod, a TLR7/8 agonist, promotes differentiation of myeloid-derived suppressor cells into macrophages and dendritic cells. Arch. Pharm. Res., 37:1234-1240 (2014).
Lu et al., TLR agonists for cancer immunotherapy: tipping the balance between the immune stimulatory and inhibitory effects. Front. Immunol., vol. 5, pp. 1-4 (2014).
Melani, et al., Targeting of Interleukin 2 to human ovarian carcinoma by fusion with a single-chain Fv of antifolate receptor antibody. Cancer Research, vol. 58, No. 18, pp. 4146-4154 (1998).
Miller et al., Imiquimod applied topically: a novel immune response modifier and new class of drug. Int. J. Immunopharmacol. 21:1-14 (1999).
Mosser et al., Exploring the full spectrum of macrophage activation. Nat Rev Immunol., 8(12):958-969 (2008).
Pribble et al., EC145: A novel targeted agent for adenocarcinoma of the lung. Expert Opin. Investig. Drugs 21:755-761 (2012).
Rudnick et al., IT-020: A dramatic clinical and cytologic response to ipilimumab in a multi-drug regiment with bevacizumab. Neuro-Oncology, vol. 15, Suppl. 3, pp. iii68-iii74 (2013).
Scott et al., Antibody therapy of cancer. Nat. Rev. Cancer 12:278-87 (2012).
Singaporean Search Report and Written Opinion for Singaporean Patent Application No. 11201500399S filed on Jul. 16, 2013 (Search completed on Mar. 16, 2016 and dated Apr. 12, 2016).
Singaporean Search Report and Written Opinion for Singaporean Patent Application No. 11201700079V filed on Jul. 8, 2015 (search completed on Mar. 6, 2018 and dated Mar. 9, 2018).
Smyth et al., Activation of NK cell cytotoxicity. Molecular Immunology, 42:501-510 (2005).
Sznol et al., Antagonist antibodies to PD-1 and B7-H1 (PD-L1) in the treatment of advanced human cancer. Clin. Cancer Res., 19(5): 1021-1034 (2013).
Sousa, Activation of dendritic cells: translating innate into adaptive immunity. Current Opinion in Immunology, 16:21-25 (2004).
Stephenson et al., TLR8 Stimulation enchances cetuximab-mediated natural killer cell lysis of head and neck cancer cells and dendritic cell cross priming of EGFR-specific CD8+ T cells. Cancer Immunol. Immunother., vol. 62, No. 8, pp. 1347-1357 (2013).
Stier et al., Combinations of TLR Ligands: A Promising Approach in Cancer Immunotherapy. Clin. & Dev. Immunol. 2013:1-14 (2013).
Supplementary European Search Report for European Patent Application No. 13820359.1 filed on Jul. 16, 2013 (Search completed on Jan. 27, 2016 and dated Apr. 1, 2016).
Supplementary Partial European Search Report for European Patent Application No. 13820359.1 filed on Jul. 16, 2013 (Search completed on Jan. 27, 2016 and dated Feb. 3, 2016).
Supplementary European Search Report for European Patents Application No. 15735122 dated Aug. 23, 2017.
Supplementary European Search Report for European Patent Application No. 15735519 dated Aug. 23, 2017.
Supplementary European Search Report and Opinion for European Patent Application No. 15818970 (search completed on Jan. 29, 2018 and dated May 14, 2018).
Supplementary Partial European Search Report for European Patent Application No. 15818970 (search completed on Jan. 29, 2018 and dated Feb. 8, 2018).
Supplementary European Search Report and Opinion for European Patent Application No. 15819519 (search completed on Jan. 29, 2018 and dated Feb. 2, 2018).
Supplementary European Search Report and Opinion for European Patent Application No. 15839010 (search completed on Feb. 20, 2018 and dated Mar. 1, 2018).
Supplementary European Search Report and Opinion for European Patent Application No. 15734849 (search completed on Aug. 11, 2017 and dated Apr. 13, 2018).
Suzanne et al., Targeting the PD-1/B7-H1(PD-L1) pathway to activate anti-tumor immunity. Current Opinion in Immunology, vol. 24, No. 2, pp. 207-212 (2012).
Timmerman, et al., In vivo activity of rituximab-CpG oligodeoxynucleotide conjugate against rituximab-resistant human CD20+ B-cell lymphoma. Journal of Clinical Oncology (ASCO Annual Meeting Proceedings—Post-Meeting Edition), vol. 27, No. 158: 8529 (2009).
Topalian et al., Targeting the PD-1/B7-H1(PD-L1) pathway to activate anti-tumor immunity. Curr. Opin. Immunol., 24(2):207-212 (2012).
International Search Report and Written Opinion for International Application No. PCT/CN2015/083585 filed on Jul. 8, 2015.
International Search Report and Written Opinion for International Application No. PCT/CN2015/070377 filed on Jan. 8, 2015.
International Search Report and Written Opinion for International Application No. PCT/CN2015/070380 filed on Jan. 8, 2015.
International Search Report and Written Opinion for International Application No. PCT/CN2015/070379 filed on Jan. 8, 2015.
International Search Report of PCT/CN2015/070379 dated Apr. 8, 2015.
International Search Report and Written Opinion for International Application No. PCT/CN2015/088456 filed on Aug. 29, 2015.
Gerster, John F. Synthesis and structure-activity-relationships of 1H-imidazo[4, 5-c]quinolines that induce interferon production. Journal of Medicinal Chemistry, No. 10, vol. 48, pp. 3481-3491 (2005).
International Search Report and Written Opinion, dated Aug. 6, 2018, for International Application No. PCT/CN2018/084674 filed on Apr. 26, 2018.
International Search Report and Written Opinion, dated Mar. 28, 2018, for International Application No. PCT/CN2017/089718 filed on Jun. 23, 2017.
U.S. Appl. No. 16/624,860, filed Dec. 19, 2019.

* cited by examiner

2-AMINO-QUINOLINE DERIVATIVES

CROSS REFERENCE TO RELATED APPLICATIONS

This application is a division of U.S. patent application Ser. No. 16/608,581, filed Oct. 25, 2019, now U.S. Pat. No. 11,053,240, issued Jul. 6, 2021, which is a 35 U.S.C. 371 national phase entry of PCT/CN2018/084674, filed Apr. 26, 2018, which claims the benefit of, and priority to, Chinese Patent Application Serial No. 201710287322.2, filed Apr. 27, 2017, the entire disclosures of which are each hereby incorporated by reference in their entireties.

FIELD OF THE INVENTION

The present invention relates to 2-amino-quinoline derivatives, such as imidazoquinoline and pyrazoloquinoline analogs as agonists of toll-like receptors 7 and 8 (TLR7 and TLR8), as well as pharmaceutical compositions comprising the same. The present invention also relates to the use of the compounds, compositions, and the method of activating TLR7 and TLR8 in treating various diseases.

BACKGROUND OF THE INVENTION

The TLR family plays a fundamental role in pathogen recognition and activation of innate immunity. TLR7 and TLR8 are toll-like receptors 7 and 8 respectively, and they lie in close proximity to each other on the human X chromosome. Both TLR7 and TLR8 recognize single-stranded RNA of viruses such as HIV and HCV. TLR7 has been shown to play a significant role in the pathogenesis of autoimmune disorders such as Systemic Lupus Erythematosus (SLE) as well as in the regulation of antiviral immunity. Genetic variants in TLR8 have recently been linked to susceptibility to pulmonary tuberculosis. TLR7 is functional both in human and mouse, while TLR8 is only functional in human, but it seems to counteract TLR7 activity. The major benefit of TLR7/8 agonists as immune response enhancers is their simultaneous stimulation of several cell types. TLR7 and TLR8 are expressed mostly on immune cells such as antigen presenting cells, including plasmacytoid dendritic cells (pDC) and myeloid dendritic cells (mDC), as well as natural killer cells, and macrophages. Activation of TLR7/8 on pDCs and mDCs results in the induction and release of type I interferons (IFN), tumor necrosis factor alpha (TNFα), and interleukin 12 (IL-12), which is an important step for the initiation of innate and adaptive immunities to kill cancer cells. For these reasons, TLR7 and TLR8 have become interesting targets in both antiviral and cancer therapy. There is also a growing interest in the targeting of toll-like receptors, such as TLR7/8 for the treatment of allergic diseases.

Small molecule agonists at TLR7 and TLR8 have increased interest in both antiviral and cancer research own to their profound antiviral and antitumor activity. The lead compound of the imidazoquinoline family, imiquimod, is efficacious against many primary skin tumors and cutaneous metastases and is marketed as a topical formulation. Resiquimod (R-848), from the same imidazoquinoline family, is a low molecular weight synthetic molecule that activates immune cells via the TLR7/TLR8 MyD88-dependent signaling pathway. It acts as an immune response modifier and has antiviral and antitumor activity. It has several mechanisms of action, being both an agonist for toll-like receptors 7 and 8, and an upregulator of the opioid growth factor receptor. R-848 is used as a topical gel in the treatment of skin lesions such as those caused by the herpes simplex virus and cutaneous T cell lymphoma, as an adjuvant to increase the effectiveness of vaccines, and as an adjuvant to immunotherapy in allergic rhinitis (AR) patient. Therefore, in addition to their use as stand-alone immunotherapeutic agent, TLR7/8 agonists hold promise as adjuvants in cancer vaccine or adoptive T cell transfer protocols. Extension of the families of the known synthetic TLR7/8 agonists, such as described above, pave the way to the development and identification of TLR7/8 agonists that are well tolerated, more selective with potent antitumor and antiviral activity, broadly applicable, and more effective as adjuvants.

SUMMARY OF THE INVENTION

Described herein are 2-amino-quinoline derivatives, pharmaceutically acceptable salts, solvates, prodrug and active metabolites, that are agonists of toll-like receptors 7 and 8 (TLR7/8). These compounds may be used to treat viral infection, such as HCV, cancer, and allergic diseases in need thereof by administering a therapeutically effective amount of a 2-amino-quinoline derivative.

Some embodiments include a compound represented by Formula 1:

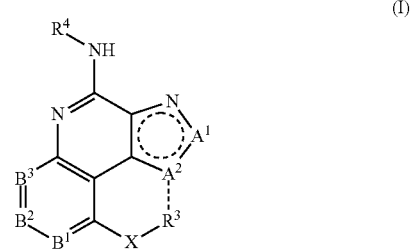

(I)

wherein a dashed line represents the presence or absence of a bond; $A^1$ is $CR^1$, $NR^{1A}$, or N; $A^2$ is $CR^2$, $NR^{2A}$, O, or S; $B^1$ is $CR^5$ or N; $B^2$ is $CR^6$ or N; $B^3$ is $CR^7$ or N; $R^1$ and $R^2$ are independently F, Cl, Br, I, $NO_2$, CN, $R^a$, $-OR^a$, $-NR^aR^b$, $-NHCOR^a$, $-NHSO_2R^a$, $-OCOR^a$, or $-SO_2R^a$; X is a bond, O, $NR^a$, $-CO-$, $-SO-$, or $-SO_2-$, $-CONR^a$, hydrocarbyl, and $R^3$ is H or $C_{1-30}$ organyl; or $X-R^3$ is F or Cl; $R^{1A}$, $R^{2A}$, $R^4$, $R^a$, and $R^b$ are independently H or $C_{1-30}$ organyl; $R^5$, $R^6$, and $R^7$ are independently F, Cl, Br, I, $NO_2$, CN, $R^a$, $-OR^a$, $-NR^aR^b$, $-NHCOR^a$, $-NHSO_2R^a$, $-OCOR^a$, $-SO_2R^a$, $-SO_2NHR^a$, or $-X^1-(C_mH_{2m}O_{0-1})-Z-(C_nH_{2n+1})$, $-(C_mH_{2m}O_{0-1})-Z-(C_nH_{2n+1})$, wherein R and $R^6$ or $R^6$ and $R^7$ can be optionally linked to form a ring; wherein $X^1$ is a bond, O, $NR^a$, $-CO-$, $-SO-$, or $-SO_2-$; Z is a bond, 0, $NHSO_2$, or NHCO; m is 0, 1, 2, 3, 4, 5, 6, 7, 8, 9, or 10; and n is 1, 2, 3, 4, 5, 6, 7, 8, 9, 10, 11, 12, 13, 14, 15, 16, 17, 18, 19, 20, 21, 22, or 23.

Some embodiments include a pharmaceutical dosage form comprising a subject compound. A subject compound or a subject composition may be used for activating TLR7/8. In addition to its use as a stand-alone immunotherapeutic agent, such as an antiviral and anticancer agent, a subject compound or composition may be used as adjuvants in cancer vaccine or adoptive T cell transfer protocols.

Some embodiments include a method of treating a disease or disorder associated with a TLR7/8 agonist comprising administering an effective amount of a subject compound to a mammal in need thereof.

Some embodiments include use of a subject compound in the manufacture of a medicament for the treatment of a disease or disorder associated with a TLR7/8 agonist.

DETAILED DESCRIPTION OF THE INVENTION

Unless otherwise indicated, when a compound or chemical structural feature, such as alkyl, alkenyl, alkynyl, aryl, heteroaryl, etc., is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15-50 g/mol, 15-100 g/mol, 15-150 g/mol, 15-200 g/mol, 15-300 g/mol, or 15-500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, aryl, heteroaryl, hydroxy, alkoxy, aryloxy, acyl, acyloxy, alkylcarboxylate, thiol, alkylthio, cyano, halo, thiocarbonyl, 0-carbamyl, N-carbamyl, 0-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

As used herein, the term "alkyl" has the broadest meaning generally understood in the art and may include a moiety composed of carbon and hydrogen containing no double or triple bonds. Alkyl may be linear alkyl, branched alkyl, cycloalkyl, or a combination thereof and in some embodiments, may contain from one to thirty-five carbon atoms. In some embodiments, alkyl may include $C_{1-10}$ linear alkyl, such as methyl (—$CH_3$), methylene (—$CH_2$—), ethyl (—$CH_2CH_3$), ethylene (—$C_2H_4$—), propylene (—$C_3H_6$—), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein the term "aryl" includes a group that can be derived from a monocyclic and polycyclic aromatic hydrocarbon by removal of a hydrogen atom from a ring carbon atom. The "aryl" may include an aromatic ring or aromatic ring system such as phenyl, naphthyl, etc.

The term "heteroaryl" has the broadest meaning understood by a person of ordinary skill in the art and includes an "aryl" which has one or more heteroatoms in the ring or ring system, such as pyridinyl, furyl, thienyl, oxazolyl, thiazolyl, imidazolyl, triazolyl, oxadiazolyl, isoxazolyl, indolyl, quinolinyl, benzofuranyl, benzothienyl, benzooxazolyl, benzothiazolyl, benzoimidazolyl, etc.

Unless otherwise indicated, any reference to a compound herein by structure, name, or any other means includes pharmaceutically acceptable salts, such as HCl, HBr, HI, $H_2SO_4$, acetate, citrate, phosphate, sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described.

If stereochemistry is not indicated, a name or structural representation includes any stereoisomer or any mixture of stereoisomers.

For the purposes of this disclosure, "treat," "treating," or "treatment" includes use of a compound, composition, therapeutically active agent, or drug in the diagnosis, cure, mitigation, treatment, or prevention of disease or other undesirable condition.

With respect to any relevant structural representation, such as Formula 1, a dashed line represents the presence or absence of a bond. For example, compounds represented by Formulas 1A and 1B are included.

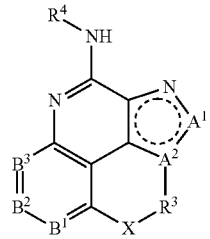

Formula 1A

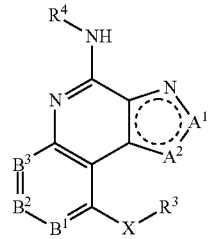

Formula 1B

With respect to any relevant structural representation, such as Formula 1, 1A, or 1B, $A^1$ is $CR^1$, $NR^{1A}$, or N. In some embodiments, $A^1$ is $CR^1$. In some embodiments, $A^1$ is $NR^{1A}$. In some embodiment, $A^1$ is N.

With respect to any relevant structural representation, such as Formula 1, 1A, or 1B $A^2$ is $CR^2$ $NR^{2A}$, O, or S. In some embodiments, $A^2$ is $CR^2$. In some embodiments, $A^2$ is $NR^{2A}$. In some embodiments, $A^2$ is O. In some embodiments, $A^2$ is S.

With respect to any relevant structural representation, such as Formula 1, 1A, or 1B, X is a bond, O, $NR^a$, —C(=O)—, —S(=O)—, —S(=O)$_2$—, —$CONR^a$, hydrocarbyl, and $R^3$ is H or $C_{1-30}$ organyl; or X—$R^3$ is F or Cl. In some embodiments, X is a bond. In some embodiments, X is 0. In some embodiments, X is $NR^a$. In some embodiments, X is —C(=O)—. In some embodiments, X is —S(=O)—.

In some embodiments, X is —S(=O)$_2$—. In some embodiments, X—R$^3$ is F. In some embodiment, X—R$^3$ is Cl.

With respect to any relevant structural representation, such as R$^a$, NR$^a$, —OR$^a$, —OCOR$^a$, or —SO$_2$R$^a$, —NR$^a$R$^b$, in such as Formula 1, 1A or 1B, R$^a$ or R$^b$ is independently H or organyl, such as C$_{1-30}$ organyl, including any organic substituent group, regardless of functional type, having a free valence at a carbon, such as optionally substituted alkyl, e.g. optionally substituted C$_{1-30}$, C$_{1-12}$, C$_{1-6}$, or C$_{1-3}$ alkyl, including methyl, ethyl, C$_3$ alkyl, C$_4$ alkyl, C$_5$ alkyl, C$_6$ alkyl, C$_7$ alkyl, C$_8$ alkyl, C$_9$ alkyl, C$_{10}$ alkyl, C$_{11}$ alkyl, C$_{12}$ alkyl, C$_{13}$ alkyl, C$_{14}$ alkyl, C$_{15}$ alkyl, C$_{16}$ alkyl, C$_{17}$ alkyl, C$_{18}$ alkyl, C$_{19}$ alkyl, C$_{20}$ alkyl, C$_{21}$ alkyl, C$_{22}$ alkyl, C$_{23}$ alkyl, C$_{24}$ alkyl, C$_{25}$ alkyl, C$_{26}$ alkyl, C$_{27}$ alkyl, C$_{28}$ alkyl, C$_{29}$ alkyl, C$_{30}$ alkyl, C$_3$ cycloalkyl, C$_4$ cycloalkyl, C$_5$ cycloalkyl, C$_6$ cycloalkyl, C$_7$ cycloalkyl, C$_8$ cycloalkyl, C$_9$ cycloalkyl, C$_{10}$ cycloalkyl, C$_{11}$ cycloalkyl, C$_{12}$ cycloalkyl, etc.; optionally substituted alkenyl, e.g. optionally substituted C$_{2-12}$ or C$_{2-6}$, alkenyl, including ethenyl, C$_3$ alkenyl, C$_4$ alkenyl, C$_5$ alkenyl, C$_6$ alkenyl, C$_7$ alkenyl, C$_8$ alkenyl, C$_9$ alkenyl, C$_{10}$ alkenyl, C$_{11}$ alkenyl, C$_{12}$ alkenyl, C$_4$ cycloalkenyl, C$_5$ cycloalkenyl, C$_6$ cycloalkenyl, C$_7$ cycloalkenyl, C$_8$ cycloalkenyl, C$_9$ cycloalkenyl, C$_{10}$ cycloalkenyl, C$_{11}$ cycloalkenyl, C$_{12}$ cycloalkenyl, etc.; optionally substituted alkynyl, e.g. optionally substituted C$_{2-12}$ or C$_{2-6}$ alkynyl, including ethynyl, C$_3$ alkynyl, C$_4$ alkynyl, C$_5$ alkynyl, C$_6$ alkynyl, C$_7$ alkynyl, C$_8$ alkynyl, C$_9$ alkynyl, C$_{10}$ alkynyl, C$_{11}$ alkynyl, C$_{12}$ alkynyl, C$_5$ cycloalkynyl, C$_6$ cycloalkynyl, C$_7$ cycloalkynyl, C$_8$ cycloalkynyl, C$_9$ cycloalkynyl, C$_{10}$ cycloalkynyl, C$_1$ cycloalkynyl, C$_{12}$ cycloalkynyl, etc.; optionally substituted aryl, such as optionally substituted phenyl, optionally substituted naphthyl, etc.; optionally substituted heterocyclyl, optionally substituted heteroaryl, etc.; organyl also includes CN, —C(O)R$^a$, —C(O)OR$^a$, —C(O)NHR$^a$, —C(O)NR$^a$R$^b$, —C(O)—Z-organyl, wherein Z is a bond, O, S, or NR$^a$R$^b$, —C(R$^a$R$^b$)—OR$^a$, —C(R$^a$R$^b$)—NR$^a$R$^b$. In some embodiments, R$^a$ or R$^b$ is independently H or C$_{1-30}$ hydrocarbyl, such as alkyl, alkenyl, alkynyl, or phenyl.

In some embodiments, C$_{1-30}$ organyl can be substituted by halogen, hydroxyl, amines, alkoxyl, aryl, heteroaryl, sulfone, sulfonamide, carboxylic acid, amide, reversed amide, ester, cycloalkyl, heterocycloalkyl, carbonyl, alkyl, alkenyl, alkynyl, phosphonamidic acid, phosphinic amide, or phosphine oxide.

Some embodiments include a compound of Formula 2 or Formula 2A.

Formula 2

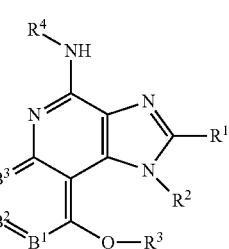

Formula 2A

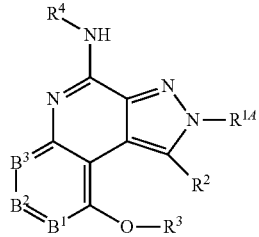

With respect to any relevant structural representation, such as Formula 1, 1A, 1B, 2, or 2A, B$^1$ is CR$^5$ or N. In some embodiments, B$^1$ is CR$^5$. In some embodiments, B$^1$ is N.

With respect to any relevant structural representation, such as Formula 1, 1A, 1B, 2, or 2A, B$^2$ is CR$^6$ or N. In some embodiments, B$^2$ is CR$^6$. In some embodiments, B$^2$ is N.

With respect to any relevant structural representation, such as Formula 1, 1A, 1B, 2, or 2A, B$^3$ is CR$^7$ or N. In some embodiments, B$^3$ is CR$^7$. In some embodiments, B$^3$ is N.

Some embodiments include a compound of Formula 3A, 3B, 3C, 3D, 3E, 4, 5, 6, 7, 8, 9, 10, 11, 12, or 13.

Formula 3A

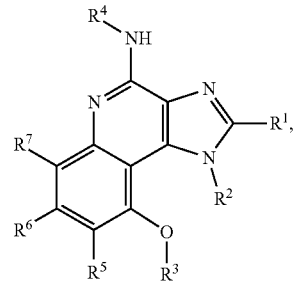

Formula 3B

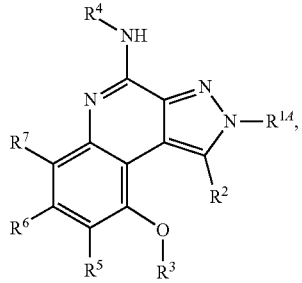

Formula 3C

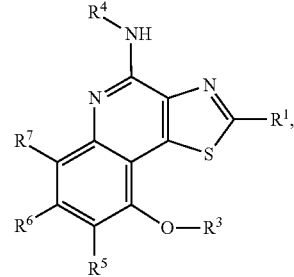

Formula 3D
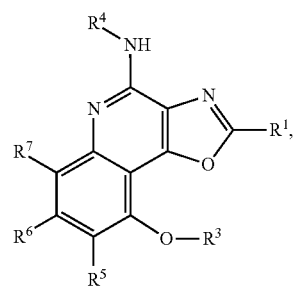
Formula 3E
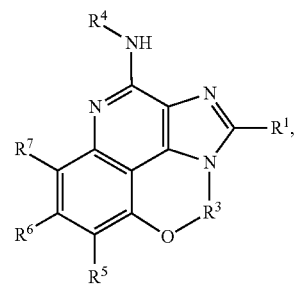
Formula 4
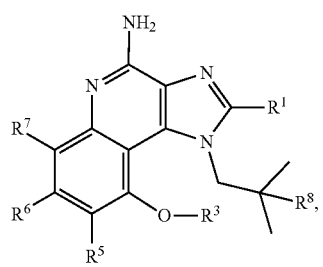
Formula 5
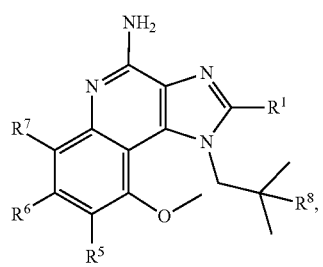
Formula 6
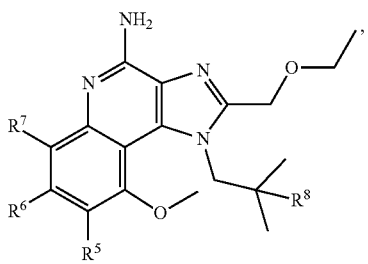
Formula 7
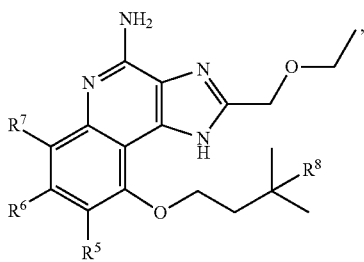
Formula 8
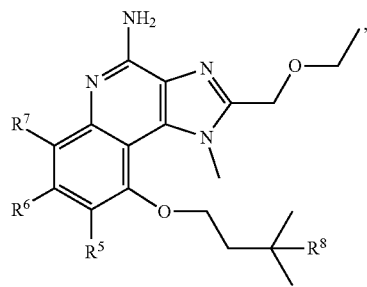
Formula 9
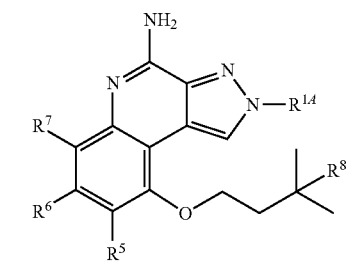
Formula 10
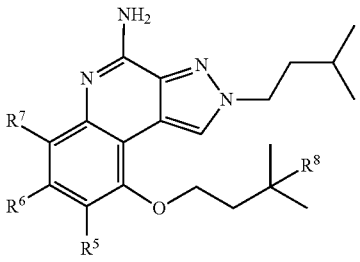
Formula 11
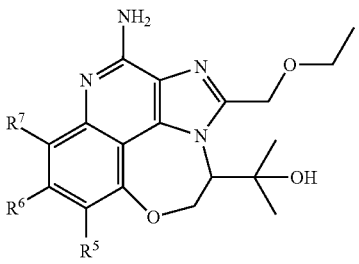
Formula 12
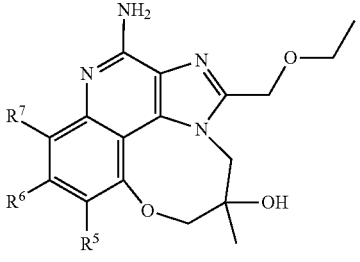
Formula 13
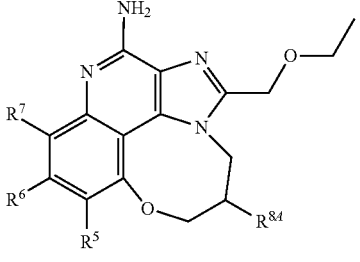

With respect to any relevant structural representation, such as Formula 1, 1A, 1B, 2, 2A, 3A, 3B, 3C, 3D, 3E, 4, 5, 6, 7, 8, 9, 10, 11, 12, or 13, $R^1$ or $R^{1A}$ is independently H or any substituent, such as F, Cl, Br, I, $NO_2$, CN, $R^a$, —$OR^a$, —$NR^aR^b$, —$NHCOR^a$, —$NHSO_2R^a$, —$OCOR^a$, or —$SO_2R^a$. In some embodiments, $R^1$ or $R^{1A}$ is $C_rH_{2r+1}O$, wherein r is 1, 2, 3, 4, 5, 6, 7, 8, 9, or 10, including $C_2H_5O$, such as —$(CH_2)_2OH$; $C_3H_7O$, such as —$CH_2OCH_2CH_3$, —$(CH_2)_2OCH_3$, etc.; $C_{1-12}$ alkyl, such as —$(CH_2)_3CH_3$, —$CH_2CH_2CH(CH_3)_2$.

In some embodiments, $R^1$ or $R^{1A}$ is —$(CH_2)_2OH$. In some embodiments, $R^1$ or $R^{1A}$ is —$CH_2OCH_2CH_3$. In some embodiments, $R^1$ or $R^{1A}$ is —$(CH_2)_2OCH_3$. In some embodiments, $R^1$ or $R^{1A}$ is —$(CH_2)_3CH_3$. In some embodiments, $R^1$ or $R^{1A}$ is —$CH_2CH_2CH(CH_3)_2$.

With respect to any relevant structural representation, such as Formula 1, 1A, 1B, 2, 2A, 3A, 3B, 4, 5, 6, 7, 8, 9, or 10, $R^2$ or $R^{2A}$ is independently H or any substituent, such as —$CH_3$, —$CH_2CH(CH_3)_2$, —$CH_2C(CH_3)_2R^8$, —$CH_2CH_2C(CH_3)_2R^8$, —$C_4H_9O$, —$CH_2CH_2OCH(CH_3)_2$.

In some embodiments, $R^2$ or $R^{2A}$ is H. In some embodiments, $R^2$ or $R^{2A}$ is $CH_3$. In some embodiments, $R^2$ or $R^{2A}$ is —$CH_2CH(CH_3)_2$. In some embodiments, $R^2$ or $R^{2A}$ is —$CH_2C(CH_3)_2R^8$. In some embodiments, $R^2$ or $R^{2A}$ is —$CH_2C(CH_3)_2OH$. In some embodiments, $R^2$ or $R^{2A}$ is —$CH_2CH_2C(CH_3)_2OH$.

In some embodiments, $R^2$ or $R^{2A}$ is —$CH_2CH_2OCH(CH_3)_2$.

With respect to any relevant structural representation, such as Formula 1, 1A, 1B, 2, 2A, 3A, 3B, 3C, 3D, 4, 5, 6, 7, 8, 9, or 10, $R^3$ is any substituent, such as $C_{1-30}$ optionally substituted alkyl, —$C_wH_{2w+1}O$ or an ester thereof, wherein w is 0, 1, 2, 3, 4, 5, 6, 7, 8, 9, or 10; —$(C_uH_{2u}O_{0-1})$—Z—$(C_vH_{2v+1})$, wherein Z is a bond, O, $NHSO_2$, or NHCO, u is 0, 1, 2, 3, 4, 5, 6, 7, 8, 9, or 10, and v is 1, 2, 3, 4, 5, 6, 7, 8, 9, 10, 11, 12, 13, 14, 15, 16, 17, 18, 19, 20, 21, 22, 23, or 24; or —$(C_tH_{2t}O_{0-1})$—Ht, wherein t is 0, 1, 2, 3, 4, 5, 6, 7, 8, 9, 10, 11, 12, 13, 14, 15, 16, 17, 18, 19, or 20, and Ht is optionally substituted $C_{3-10}$ heterocyclyl.

In some embodiments, $R^3$ is H. In some embodiment, $R^3$ is $CH_3$. In some embodiments, $R^3$ is —$CH_2CH(CH_3)_2$. In some embodiments, $R^3$ is —$(CH_2)_2CH(CH_3)_2$. In some embodiments, $R^3$ is —$CH_2CH(OH)CH_3$. In some embodiments, $R^3$ is —$(CH_2)_2CH(OH)CH_3$. In some embodiments, $R^3$ is —$(CH_2)_2C(CH_3)_2OH$. In some embodiments, $R^3$ is $(CH_2)_2OCH(CH_3)_2$, —$(CH_2)_3NHSO_2CH_3$, —$(CH_2)_4NHSO_2CH_3$, —$(CH_2)_2O(CH_2)_2NHSO_2CH_3$, —$(CH_2)_3NHCOC_{17}H_{35}$, —$(CH_2)_3NHCOCH_3$, —$(CH_2)_4NHCOCH_3$, —$(CH_2)_4NHCOC_{17}H_{35}$, —$(CH_2)_3NH_2$,

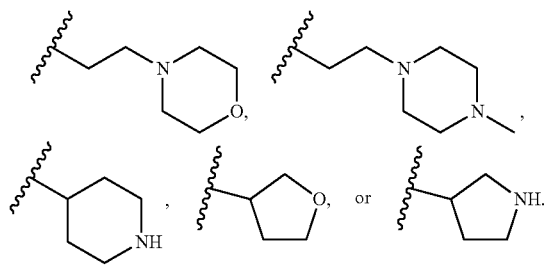

With respect to any relevant structural representation, such as Formula 3E, $R^3$ is $C_{1-3}$ alkyl optionally substituted with 1 to 6 of $R^{8A}$, same or different, wherein $R^{8A}$ is OH, oxide, $C_{1-6}$ organyl, or —O—$(C_{1-6}$ organyl).

With respect to any relevant structural representation, such as Formula 1, 1A, 1B, 2, 2A, 3A, 3B, 3C, 3D, 3E, 4, 5, 6, 7, 8, 9, 10, 11, 12, or 13, $R^4$ is H or any substituent, such as hydrocarbyl.

In some embodiments, $R^4$ is H.

With respect to any relevant structural representation, such as Formula 1, 1A, 1B, 2, 2A, 3A, 3B, 3C, 3D, 3E, 4, 5, 6, 7, 8, 9, 10, 11, 12, or 13, $R^5$ is H or any substituent, such as F, Cl, $R^a$, —$CO_2R^a$, —$CONR^aR^b$, CN, —$OR^a$, —$NR^aR^b$, —$NHCOR^a$, —$NHSO_2R^a$, —$OCOR^a$, or —$SO_2R^a$, wherein $R^a$ and $R^b$ are independently H or $C_{1-30}$ organyl. In some embodiments, $R^5$ is —$(C_mH_{2m}O_{0-1})$—Z—$(C_nH_{2n+1})$, wherein Z is a bond, 0, —$NHSO_2$, or —NHCO, m is 0, 1, 2, 3, 4, 5, 6, 7, 8, 9, or 10, and n is 1, 2, 3, 4, 5, 6. 7. 8. 9. 10, 11, 12, 13, 14, 15, 16, 17, 18, 19, 20, 21, 22, 23, or 24. In some embodiments, $R^5$ is H.

With respect to any relevant structural representation, such as Formula 1, 1A, 1B, 2, 2A, 3A, 3B, 3C, 3D, 3E, 4, 5, 6, 7, 8, 9, 10, 11, 12, or 13, $R^6$ is H or any substituent, such as F, Cl, $R^a$, —$CO_2R^a$, —$CONR^aR^b$, CN, —$OR^a$, —$NR^aR^b$, —$NHCOR^a$, —$NHSO_2R^a$, —$OCOR^a$, or —$SO_2R^a$, wherein $R^a$ and R are independently H or $C_{1-30}$ organyl. In some embodiment, $R^6$ is —$(C_mH_{2m}O_{0-1})$—Z—$(C_nH_{2n+1})$, wherein Z is a bond, 0, —$NHSO_2$, or —NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, 23, or 24. In some embodiments, $R^6$ is H.

With respect to any relevant structural representation, such as Formula 1, 1A, 1B, 2, 2A, 3A, 3B, 3C, 3D, 3E, 4, 5, 6, 7, 8, 9, 10, 11, 12, or 13, $R^7$ is H or any substituent, such as F, Cl, $R^a$, —$CO_2R^a$, —$CONR^aR^b$, CN, —$OR^a$, —$NR^aR^b$, —$NHCOR^a$, —$NHSO_2R^a$, —$OCOR^a$, or —$SO_2R^a$, wherein $R^a$ and R are independently H or $C_{1-30}$ organyl. In some embodiment, $R^7$ is —$(C_mH_{2m}O_{0-1})$—Z—$(C_nH_{2n+1})$, wherein Z is a bond, 0, —$NHSO_2$, or —NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, 23, or 24. In some embodiments, $R^7$ is H.

With respect to any relevant structural representation, such as Formula 4, 5, 6, 7, 8, 9, or 10, $R^8$ is H, OH or $C_{1-6}$ alkyl. In some embodiments, $R^8$ is H. In some embodiments, $R^8$ is OH. In some embodiment, $R^8$ is $CH_3$.

With respect to any relevant structural representation, such as Formula 3E, $R^{8A}$ is OH, oxide, $C_{1-6}$ organyl, or —O—$(C_{1-6}$ organyl). 1 to 6, same or different $R^{8A}$ can be attached at any ring C-atom. In some embodiments, $R^{8A}$ is OH. In some embodiments, $R^{8A}$ is $CH_3$. In some embodiments, two different $R^{8A}$, such as $CH_3$ and OH, are attached to a same ring C-atom. In some embodiments, $R^{8A}$ is —$C(CH_3)_2OH$.

With respect to any relevant structural representation, such as Formula 1, 1A, 1B, 2, 2A, 3A, 3B, 3C, 3D, 4, 5, 6, 7, 8, 9, or 10, in some embodiment, $R^3$ and $R^4$ are independently H or $C_{1-12}$ organyl; $R^1$, $R^2$, $R^5$, $R^6$, and $R^7$ are independently F, Cl, Br, I, $NO_2$, CN, —$OR^a$, —$NR^aR^b$, —$OCOR^a$, or —$SO_2R^a$; $R^{1A}$ and $R^{2A}$ are $R^a$; $R^a$ and $R^b$ are independently H or $C_{1-12}$ organyl; and $R^8$ is H or OH. In some embodiment, R and $R^6$ or $R^6$ and $R^7$ can be optionally linked to form a saturated or an unsaturated ring.

Some embodiments include optionally substituted 9-methoxy-1H-imidazo[4,5-c]quinolin-4-amine or a salt thereof.

Some embodiments include optionally substituted 1-(4-amino-2-(ethoxymethyl)-9-methoxy-1H-imidazo[4,5-c]quinolin-1-yl)-2-methylpropan-2-ol or a salt thereof, optionally substituted 2-(ethoxymethyl)-1-isobutyl-9-methoxy-1H-imidazo[4,5-c]quinolin-4-amine or a salt thereof, optionally substituted 1-(4-amino-9-methoxy-2-(2-methoxyethyl)-1H-imidazo[4,5-c]quinolin-1-yl)-2-methylpropan-2-ol or a salt thereof, optionally substituted 1-(4-amino-2-(2-hydroxyethyl)-9-methoxy-1H-imidazo[4,5-c]quinolin-1-yl)-2-methylpropan-2-ol or a salt thereof, optionally substituted 4-((4-amino-2-(ethoxymethyl)-1H-imidazo[4,5-c]quinolin-9-yl)oxy)-2-methylbutan-2-ol or a salt thereof, optionally substituted 2-(ethoxymethyl)-9-(isopentyloxy)-1H-imidazo[4,5-c]quinolin-4-amine or a salt thereof, optionally substituted 4-((4-amino-2-(ethoxymethyl)-1H-imidazo[4,5-c]quinolin-9-yl)oxy)butan-2-ol or a salt thereof, optionally substituted 1-((4-amino-2-(ethoxymethyl)-1H-imidazo[4,5-c]quinolin-9-yl)oxy)propan-2-ol or a salt thereof, optionally substituted 4-((4-amino-2-(2-methoxyethyl)-1H-imidazo[4,5-c]quinolin-9-yl)oxy)-2-methylbutan-2-ol or a salt thereof, optionally substituted 4-((4-amino-2-(ethoxymethyl)-1-methyl-1H-imidazo[4,5-c]quinolin-9-yl)oxy)-2-methylbutan-2-ol or a salt thereof, optionally substituted 2-(ethoxymethyl)-9-(2-isopropoxyethoxy)-1H-imidazo[4,5-c]quinolin-4-amine or a salt thereof; or optionally substituted 4-((4-amino-2-(ethoxymethyl)-1-isobutyl-1H-imidazo[4,5-c]quinolin-9-yl)oxy)-2-methylbutan-2-ol or a salt thereof, optionally substituted 2-(ethoxymethyl)-1-(2-isopropoxyethyl)-9-methoxy-1H-imidazo[4,5-c]quinolin-4-amine or a salt thereof, optionally substituted 4-(4-amino-2-(ethoxymethyl)-9-methoxy-1H-imidazo[4,5-c]quinolin-1-yl)-2-methylbutan-2-ol or a salt thereof, optionally substituted 2-(ethoxymethyl)-9-isobutoxy-1H-imidazo[4,5-c]quinolin-4-amine or a salt thereof, optionally substituted 2-(ethoxymethyl)-9-(2-isopropoxyethoxy)-1-methyl-1H-imidazo[4,5-c]quinolin-4-amine or a salt thereof, optionally substituted 2-(ethoxymethyl)-9-(isopentyloxy)-1-methyl-1H-imidazo[4,5-c]quinolin-4-amine or a salt thereof, optionally substituted 2-(ethoxymethyl)-9-isobutoxy-1-methyl-1H-imidazo[4,5-c]quinolin-4-amine or a salt thereof; optionally substituted N-(3-((4-amino-2-(ethoxymethyl)-1-methyl-1H-imidazo[4,5-c]quinolin-9-yl)oxy)propyl)methanesulfonamide or a salt thereof, optionally substituted N-(2-(2-((4-amino-2-(ethoxymethyl)-1-methyl-1H-imidazo[4,5-c]quinolin-9-yl)oxy)ethoxy)ethyl)-methanesulfonamide or a salt thereof, optionally substituted N-(3-((4-amino-2-(ethoxymethyl)-1-methyl-1H-imidazo[4,5-c]quinolin-9-yl)oxy)propyl)acetamide or a salt thereof, optionally substituted N-(4-((4-amino-2-(ethoxymethyl)-1-methyl-1H-imidazo[4,5-c]quinolin-9-yl)oxy)butyl)methanesulfonamide or a salt thereof, optionally substituted N-(3-((4-amino-2-(ethoxymethyl)-1-methyl-1H-imidazo[4,5-c]quinolin-9-yl)oxy)propyl)stearamide or a salt thereof, optionally substituted N-(4-((4-amino-2-(ethoxymethyl)-1-methyl-1H-imidazo[4,5-c]quinolin-9-yl)oxy)butyl)acetamide or a salt thereof, optionally substituted N-(4-((4-amino-2-(ethoxymethyl)-1-methyl-1H-imidazo[4,5-c]quinolin-9-yl)oxy)butyl)-stearamide or a salt thereof, optionally substituted 2-(ethoxymethyl)-1-methyl-9-(2-morpholinoethoxy)-1H-imidazo[4,5-c]quinolin-4-amine or a salt thereof, optionally substituted 2-(ethoxymethyl)-1-methyl-9-((tetrahydrofuran-3-yl)oxy)-1H-imidazo[4,5-c]quinolin-4-amine or a salt thereof, optionally substituted 2-(ethoxymethyl)-1-methyl-9-(pyrrolidin-3-yloxy)-1H-imidazo[4,5-c]quinolin-4-amine or a salt thereof, optionally substituted 2-(ethoxymethyl)-1-methyl-9-(piperidin-4-yloxy)-1H-imidazo[4,5-c]quinolin-4-amine or a salt thereof, optionally substituted N-(3-((4-amino-2-(ethoxymethyl)-1-methyl-1H-imidazo[4,5-c]quinolin-9-yl)oxy)propyl)palmitamide or a salt thereof, optionally substituted N-(4-((4-amino-2-(ethoxymethyl)-1-methyl-1H-imidazo[4,5-c]quinolin-9-yl)oxy)butyl)palmitamide or a salt thereof, optionally substituted 9-(3-aminopropoxy)-2-(ethoxymethyl)-1-methyl-1H-imidazo[4,5-c]quinolin-4-amine or a salt thereof, optionally substituted 2-(ethoxymethyl)-9-isopropoxy-1-methyl-1H-imidazo[4,5-c]quinolin-4-amine or a salt thereof, optionally substituted 1-((4-amino-2-(ethoxymethyl)-1-methyl-1H-imidazo[4,5-c]quinolin-9-yl)oxy)-2-methylpropan-2-ol or a salt thereof, optionally substituted 2-(ethoxymethyl)-3,4-dihydro-5-oxa-1,2a,9-triazanaphtho[2,1,8-cde]azulen-10-amine or a salt thereof; optionally substituted (R)-2-(10-amino-2-(ethoxymethyl)-3,4-dihydro-5-oxa-1,2a,9-triazanaphtho[2,1,8-cde]azulen-3-yl)propan-2-ol or a salt thereof, optionally substituted (S)-2-(10-amino-2-(ethoxymethyl)-3,4-dihydro-5-oxa-1,2a,9-triazanaphtho[2,1,8-cde]azulen-3-yl)propan-2-ol or a salt thereof, optionally substituted (S)-2-amino-12-(ethoxymethyl)-6-methyl-6,7-dihydro-5H-3,4-(azenometheno)[1,5]oxazocino[4,3,2-de]quinolin-6-ol or a salt thereof, optionally substituted (R)-2-amino-12-(ethoxymethyl)-6-methyl-6,7-dihydro-5H-3,4-(azenometheno)[1,5]oxazocino[4,3,2-de]quinolin-6-ol or a salt thereof, optionally substituted (R)-2-amino-12-(ethoxymethyl)-6,7-dihydro-5H-3,4-(azenometheno)[1,5]oxazocino[4,3,2-de]quinolin-6-ol or a salt thereof, optionally substituted (S)-2-amino-12-(ethoxymethyl)-6,7-dihydro-5H-3,4-(azenometheno)[1,5]oxazocino-[4,3,2-de]quinolin-6-ol or a salt thereof, optionally substituted 2-amino-12-(ethoxymethyl)-5H-3,4-(azenometheno)[1,5]oxazocino[4,3,2-de]quinolin-6(7H)-one or a salt thereof, or optionally substituted tert-butyl 4-((4-amino-2-(ethoxymethyl)-1-methyl-1H-imidazo[4,5-c]quinolin-9-yl)oxy)piperidine-1-carboxylate or a salt thereof.

TABLE 3

| Compound Name | Structure |
| --- | --- |
| 9-methoxy-1H-imidazo[4,5-c]quinolin-4-amine | 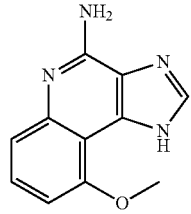 [SMILES: COc1cccc2nc(N)c3nc[nH]c3c12] |

TABLE 3-continued

| Compound Name | Structure |
|---|---|
| 1-(4-amino-2-(ethoxymethyl)-9-methoxy-1H-imidazo[4,5-c]quinolin-1-yl)-2-methylpropan-2-ol | 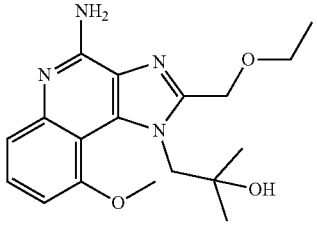 [SMILES: CCOCc1nc2c(N)nc3cccc(OC)c3c2n1CC(C)(C)O] |
| 2-(ethoxymethyl)-1-isobutyl-9-methoxy-1H-imidazo[4,5-c]quinolin-4-amine | 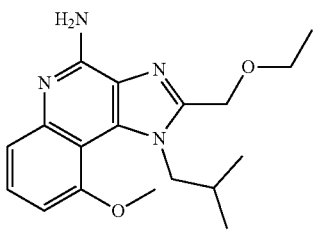 |
| 1-(4-amino-9-methoxy-2-(2-methoxyethyl)-1H-imidazo[4,5-c]quinolin-1-yl)-2-methylpropan-2-ol | 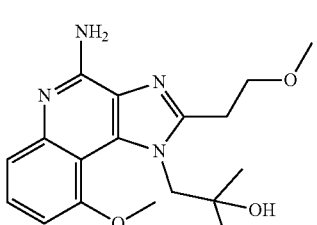 |
| 1-(4-amino-2-(2-hydroxyethyl)-9-methoxy-1H-imidazo[4,5-c]quinolin-1-yl)-2-methylpropan-2-ol | 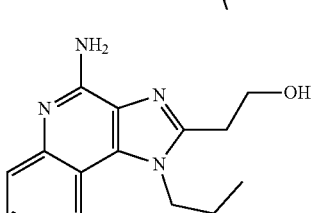 |
| 4-((4-amino-2-(ethoxymethyl)-1H-imidazo[4,5-c]quinolin-9-yl)oxy)-2-methylbutan-2-ol | 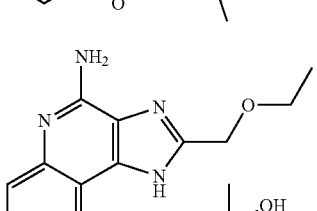 |
| 2-(ethoxymethyl)-9-(isopentyloxy)-1H-imidazo[4,5-c]quinolin-4-amine | 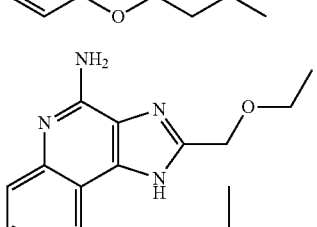 |
| 4-((4-amino-2-(ethoxymethyl)-1H-imidazo[4,5-c]quinolin-9-yl)oxy)butan-2-ol | 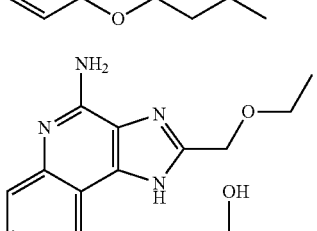 |

TABLE 3-continued

| Compound Name | Structure |
|---|---|
| 1-((4-amino-2-(ethoxymethyl)-1H-imidazo[4,5-c]quinolin-9-yl)oxy)propan-2-ol | 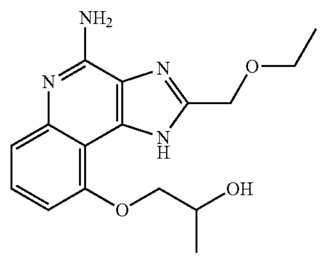 [SMILES: CCOCc1nc2c(N)nc3cccc(OCC(C)O)c3c2[nH]1] |
| 4-((4-amino-2-(2-methoxyethyl)-1H-imidazo[4,5-c]quinolin-9-yl)oxy)-2-methylbutan-2-ol | 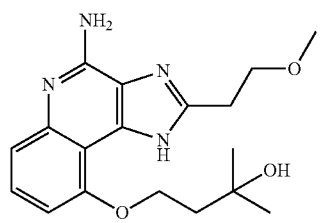 [SMILES: COCCc1nc2c(N)nc3cccc(OCCC(C)(C)O)c3c2[nH]1] |
| 4-((4-amino-2-(ethoxymethyl)-1-methyl-1H-imidazo[4,5-c]quinolin-9-yl)oxy)-2-methylbutan-2-ol | 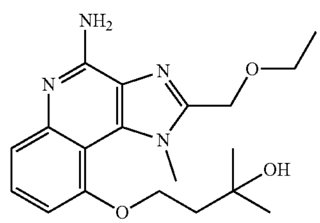 [SMILES: CCOCc1nc2c(N)nc3cccc(OCCC(C)(C)O)c3c2n1C] |
| 2-(ethoxymethyl)-9-(2-isopropoxyethoxy)-1H-imidazo[4,5-c]quinolin-4-amine | 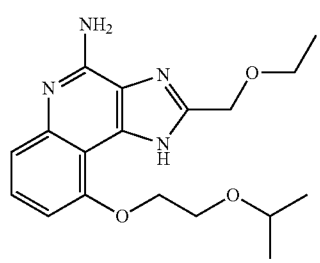 [SMILES: CCOCc1nc2c(N)nc3cccc(OCCOC(C)C)c3c2[nH]1] |
| 4-((4-amino-2-(ethoxymethyl)-1-isobutyl-1H-imidazo[4,5-c]quinolin-9-yl)oxy)-2-methylbutan-2-ol | 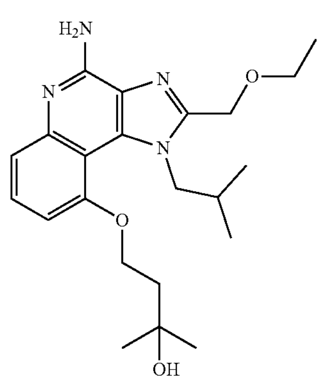 [SMILES: CCOCc1nc2c(N)nc3cccc(OCCC(C)(C)O)c3c2n1CC(C)C] |

TABLE 3-continued

| Compound Name | Structure |
|---|---|
| 2-(ethoxymethyl)-1-(2-isopropoxyethyl)-9-methoxy-1H-imidazo[4,5-c]quinolin-4-amine | 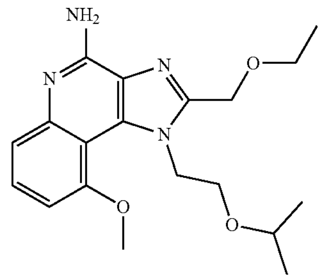 [SMILES: CCOCc1nc2c(N)nc3cccc(OC)c3c2n1CCOC(C)C] |
| 4-(4-amino-2-(ethoxymethyl)-9-methoxy-1H-imidazo[4,5-c]quinolin-1-yl)-2-methylbutan-2-ol | 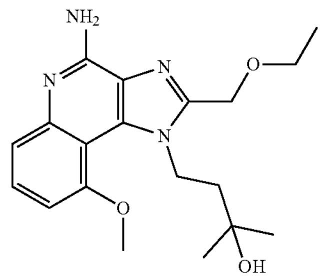 [SMILES: CCOCc1nc2c(N)nc3cccc(OC)c3c2n1CCC(C)(C)O] |
| 2-(ethoxymethyl)-9-isobutoxy-1H-imidazo[4,5-c]quinolin-4-amine | 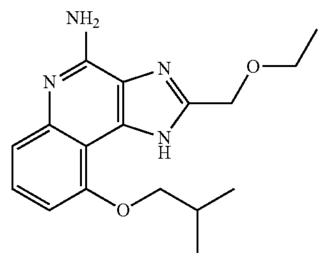 [SMILES: CCOCc1nc2c(N)nc3cccc(OCC(C)C)c3c2[nH]1] |
| 2-(ethoxymethyl)-9-(2-isopropoxyethoxy)-1-methyl-1H-imidazo[4,5-c]quinolin-4-amine | 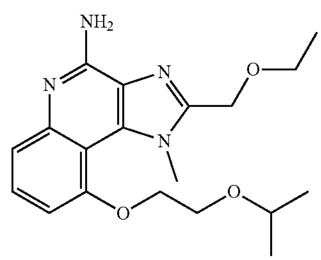 [SMILES: CCOCc1nc2c(N)nc3cccc(OCCOC(C)C)c3c2n1C] |
| 2-(ethoxymethyl)-9-isobutoxy-1-methyl-1H-imidazo[4,5-c]quinolin-4-amine | |
| 2-(ethoxymethyl)-9-isobutoxy-1-methyl-1H-imidazo[4,5-c]quinolin-4-amine | |

TABLE 3-continued

| Compound Name | Structure |
| --- | --- |
| N-(3-((4-amino-2-(ethoxymethyl)-1-methyl-1H-imidazo[4,5-c]quinolin-9-yl)oxy)propyl)methanesulfonamide | 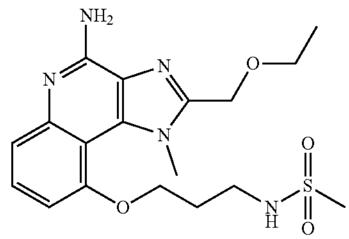 [SMILES: CCOCc1nc2c(N)nc3cccc(OCCCNS(C)(=O)=O)c3c2n1C] |
| N-(2-(2-((4-amino-2-(ethoxymethyl)-1-methyl-1H-imidazo[4,5-c]quinolin-9-yl)oxy)ethoxy)ethyl)methanesulfonamide | 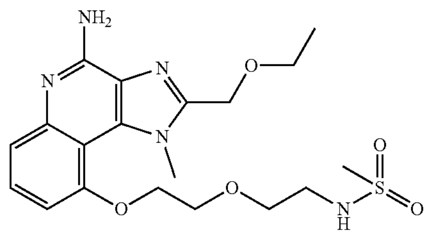 [SMILES: CCOCc1nc2c(N)nc3cccc(OCCOCCNS(C)(=O)=O)c3c2n1C] |
| N-(3-((4-amino-2-(ethoxymethyl)-1-methyl-1H-imidazo[4,5-c]quinolin-9-yl)oxy)propyl)acetamide | 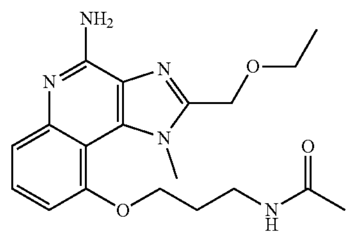 [SMILES: CCOCc1nc2c(N)nc3cccc(OCCCNC(C)=O)c3c2n1C] |
| N-(4-((4-amino-2-(ethoxymethyl)-1-methyl-1H-imidazo[4,5-c]quinolin-9-yl)oxy)butyl)methanesulfonamide | 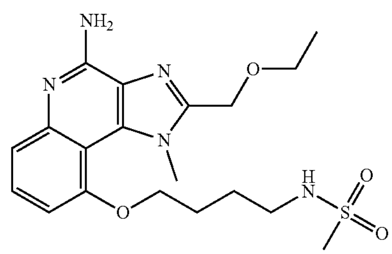 [SMILES: CCOCc1nc2c(N)nc3cccc(OCCCCNS(C)(=O)=O)c3c2n1C] |
| N-(3-((4-amino-2-(ethoxymethyl)-1-methyl-1H-imidazo[4,5-c]quinolin-9-yl)oxy)propyl)stearamide | 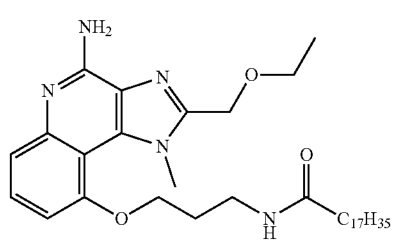 |
| N-(4-((4-amino-2-(ethoxymethyl)-1-methyl-1H-imidazo[4,5-c]quinolin-9-yl)oxy)butyl)acetamide | 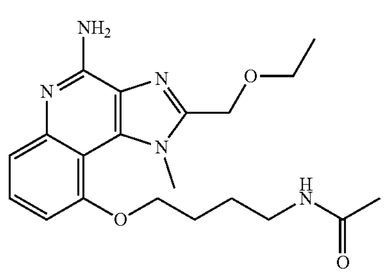 [SMILES: CCOCc1nc2c(N)nc3cccc(OCCCCNC(C)=O)c3c2n1C] |

TABLE 3-continued

| Compound Name | Structure |
|---|---|
| N-(4-((4-amino-2-(ethoxymethyl)-1-methyl-1H-imidazo[4,5-c]quinolin-9-yl)oxy)butyl)stearamide | 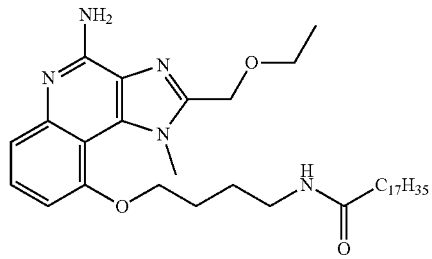 |
| 2-(ethoxymethyl)-1-methyl-9-(2-morpholinoethoxy)-1H-imidazo[4,5-c]quinolin-4-amine | 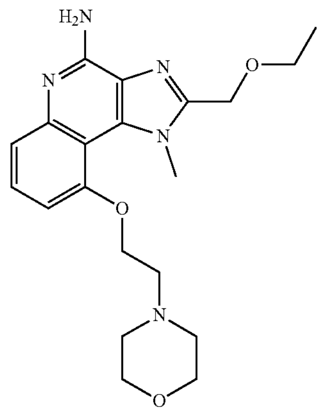 [SMILES: CCOCc1nc2c(N)nc3cccc(OCCN4CCOCC4)c3c2n1C] |
| 2-(ethoxymethyl)-1-methyl-9-((tetrahydrofuran-3-yl)oxy)-1H-imidazo[4,5-c]quinolin-4-amine | 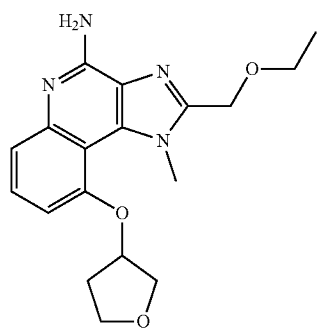 [SMILES: CCOCc1nc2c(N)nc3cccc(OC4CCOC4)c3c2n1C] |
| 2-(ethoxymethyl)-1-methyl-9-(pyrrolidin-3-yloxy)-1H-imidazo[4,5-c]quinolin-4-amine | 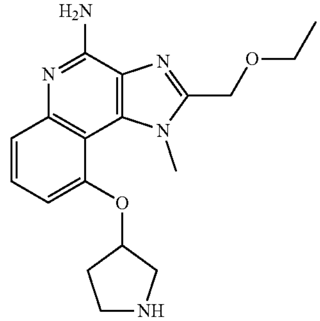 [SMILES: CCOCc1nc2c(N)nc3cccc(OC4CCNC4)c3c2n1C] |

TABLE 3-continued

| Compound Name | Structure |
|---|---|
| 2-(ethoxymethyl)-1-methyl-9-(piperidin-4-yloxy)-1H-imidazo[4,5-c]quinolin-4-amine | 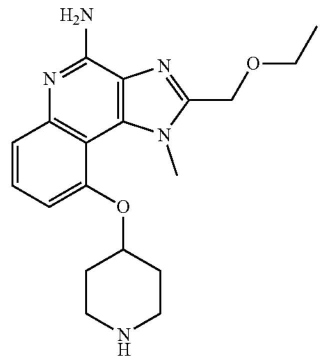 [SMILES: CCOCc1nc2c(N)nc3cccc(OC4CCNCC4)c3c2n1C] |
| N-(3-((4-amino-2-(ethoxymethyl)-1-methyl-1H-imidazo[4,5-c]quinolin-9-yl)oxy)propyl)palmitamide | 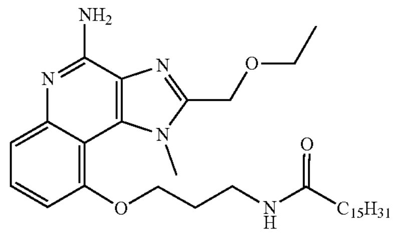 |
| N-(4-((4-amino-2-(ethoxymethyl)-1-methyl-1H-imidazo[4,5-c]quinolin-9-yl)oxy)butyl)palmitamide | 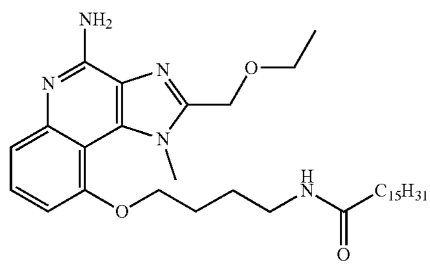 |
| 9-(3-aminopropoxy)-2-(ethoxymethyl)-1-methyl-1H-imidazo[4,5-c]quinolin-4-amine | 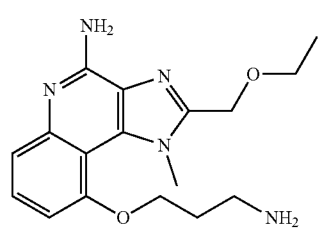 [SMILES: CCOCc1nc2c(N)nc3cccc(OCCCN)c3c2n1C] |
| 2-(ethoxymethyl)-9-isopropoxy-1-methyl-1H-imidazo[4,5-c]quinolin-4-amine | 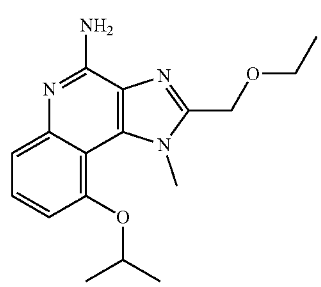 [SMILES: CCOCc1nc2c(N)nc3cccc(OC(C)C)c3c2n1C] |

TABLE 3-continued

| Compound Name | Structure |
|---|---|
| 1-((4-amino-2-(ethoxymethyl)-1-methyl-1H-imidazo[4,5-c]quinolin-9-yl)oxy)-2-methylpropan-2-ol | 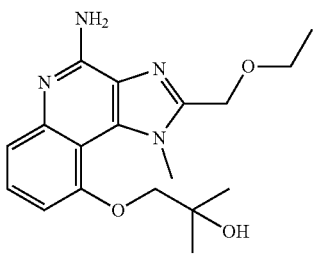 [SMILES: CCOCc1nc2c(N)nc3cccc(OCC(C)(C)O)c3c2n1C] |
| 2-(ethoxymethyl)-3,4-dihydro-5-oxa-1,2a,9-triazanaphtho[2,1,8-cde]azulen-10-amine | 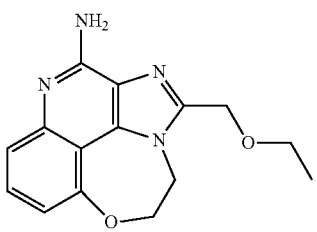 [SMILES: CCOCc1nc2c(N)nc3cccc4c3c2n1CCO4] |
| (R)-2-(10-amino-2-(ethoxymethyl)-3,4-dihydro-5-oxa-1,2a,9-triazanaphtho[2,1,8-cde]azulen-3-yl)propan-2-ol | 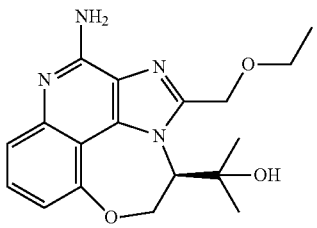 [SMILES: CCOCc1nc2c(N)nc3cccc4c3c2n1[C@@H](C(C)(C)O)CO4] |
| (S)-2-(10-amino-2-(ethoxymethyl)-3,4-dihydro-5-oxa-1,2a,9-triazanaphtho[2,1,8-cde]azulen-3-yl)propan-2-ol | 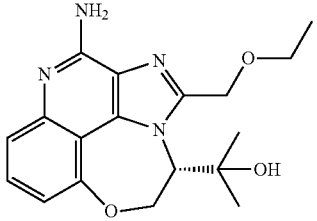 [SMILES: CCOCc1nc2c(N)nc3cccc4c3c2n1[C@H](C(C)(C)O)CO4] |
| (S)-2-amino-12-(ethoxymethyl)-6-methyl-6,7-dihydro-5H-3,4-(azenometheno)[1,5]oxazocino[4,3,2-de]quinolin-6-ol | 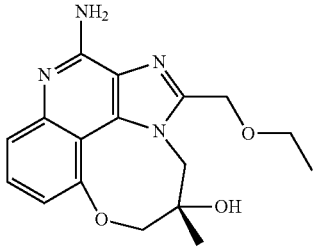 [SMILES: CCOCc1nc2c(N)nc3cccc4c3c2n1C[C@](C)(O)CO4] |
| (R)-2-amino-12-(ethoxymethyl)-6-methyl-6,7-dihydro-5H-3,4-(azenometheno)[1,5]oxazocino[4,3,2-de]quinolin-6-ol | 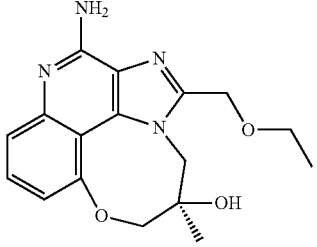 [SMILES: CCOCc1nc2c(N)nc3cccc4c3c2n1C[C@@](C)(O)CO4] |

TABLE 3-continued

| Compound Name | Structure |
|---|---|
| (R)-2-amino-12-(ethoxymethyl)-6,7-dihydro-5H-3,4-(azenometheno)[1,5]oxazocino[4,3,2-de]quinolin-6-ol | 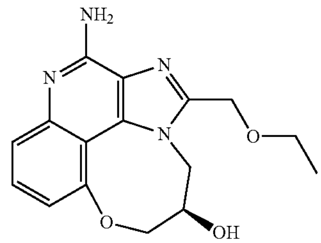 [SMILES: CCOCc1nc2c(N)nc3cccc4c3c2n1C[C@@H](O)CO4] |
| (S)-2-amino-12-(ethoxymethyl)-6,7-dihydro-5H-3,4-(azenometheno)[1,5]oxazocino[4,3,2-de]quinolin-6-ol | 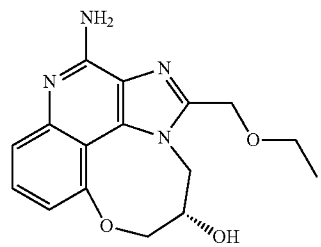 [SMILES: CCOCc1nc2c(N)nc3cccc4c3c2n1C[C@H](O)CO4] |
| 2-amino-12-(ethoxymethyl)-5H-3,4-(azenometheno)[1,5]oxazocino[4,3,2-de]quinolin-6(7H)-one | 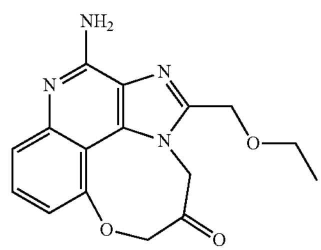 [SMILES: CCOCc1nc2c(N)nc3cccc4c3c2n1CC(=O)CO4] |
| tert-butyl 4-((4-amino-2-(ethoxymethyl)-1-methyl-1H-imidazo[4,5-c]quinolin-9-yl)oxy)piperidine-1-carboxylate | 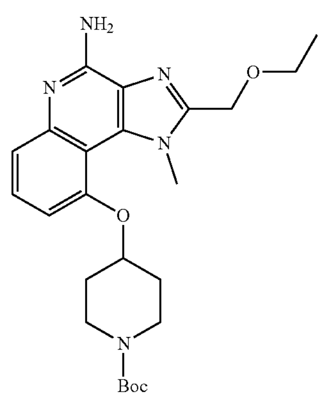 [SMILES: CCOCc1nc2c(N)nc3cccc(OC4CCN(C(=O)OC(C)(C)C)CC4)c3c2n1C] |

Some embodiments include optionally substituted 4-amino-2H-pyrazolo[3,4-c]quinolin-9-ol or a salt thereof; or optionally substituted 4-amino-2-isopentyl-2H-pyrazolo[3,4-c]quinolin-9-ol or a salt thereof optionally substituted 2-isopentyl-9-(isopentyloxy)-2H-pyrazolo[3,4-c]quinolin-4-amine or a salt thereof, or optionally substituted 2-butyl-9-(isopentyloxy)-2H-pyrazolo[3,4-c]quinolin-4-amine or a salt thereof.

TABLE 4

| Compound Name | Structure |
|---|---|
| 4-amino-2H-pyrazolo[3,4-c]quinolin-9-ol | 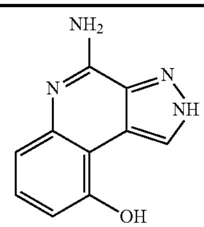 |
| 4-amino-2-isopentyl-2H-pyrazolo[3,4-c]quinolin-9-ol | 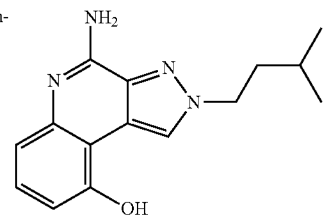 |
| 2-isopentyl-9-(isopentyloxy)-2H-pyrazolo[3,4-c]quinolin-4-amine | 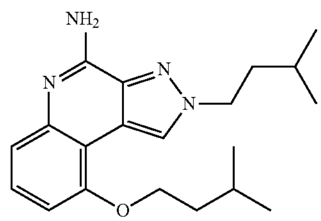 [SMILES: CC(C)CCOc1cccc2nc(N)c3nn(CCC(C)C)cc3c12] |
| 2-butyl-9-(isopentyloxy)-2H-pyrazolo[3,4-c]quinolin-4-amine | 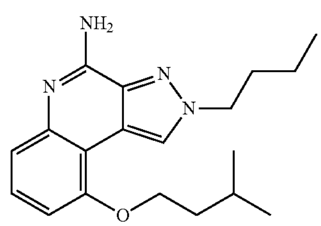 |

The following embodiments are specifically contemplated herein.

Embodiment 1. A compound represented by a formula:

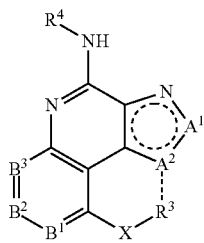

or a salt thereof;
wherein a dashed line represents the presence or absence of a bond;
$A^1$ is $CR^1$, $NR^{1A}$, or N;
$A^2$ is $CR^2$, $NR^{2A}$, O, or S;
$B^1$ is $CR^5$ or N;
$B^2$ is $CR^6$ or N;
$B^3$ is $CR^7$ or N;
$R^1$ and $R^2$ are independently F, Cl, Br, I, $NO_2$, CN, $R^a$, $-OR^a$, $-NR^aR^b$, $-NHCOR^a$, $-NHSO_2R^a$, $-OCOR^a$, or $-SO_2R^a$;
X is a bond, O, $NR^a$, $-CO-$, $-SO-$, or $-SO_2-$, $-CONR^a$, hydrocarbyl, and $R^3$ is H or $C_{1-30}$ organyl; or $X-R^3$ is F or Cl;
$R^{1A}$, $R^{2A}$, $R^4$, $R^a$, and R are independently H or $C_{1-30}$ organyl;
$R^5$, $R^6$, and $R^7$ are independently F, Cl, Br, I, $NO_2$, CN, $R^a$, $-OR^a$, $-NR^aR^b$, $-NHCOR^a$, $-NHSO_2R^a$, $-OCOR^a$, $-SO_2R^a$, or $-X^1-(C_mH_{2m}O_{0-1})-Z-(C_nH_{2n+1})$, $-(C_mH_{2m}O_{0-1})-Z-(C_nH_{2n+1})$, wherein $R^5$ and $R^6$ or $R^6$ and $R^7$ can be optionally linked to form a ring;
wherein $X^1$ is a bond, O, $NR^a$, $-CO-$, $-SO-$, or $-SO_2-$;
Z is a bond, O, $NHSO_2$, or NHCO;
m is 0, 1, 2, 3, 4, 5, 6, 7, 8, 9, or 10; and
n is 1, 2, 3, 4, 5, 6, 7, 8, 9, 10, 11, 12, 13, 14, 15, 16, 17, 18, 19, 20, 21, 22, or 23.

Embodiment 2. The compound of embodiment 1, further represented by a formula:

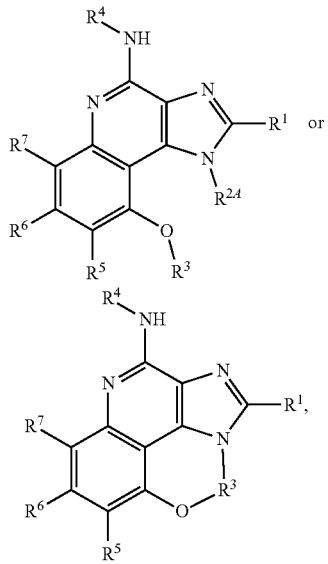

or a salt thereof, wherein $R^3$ is $C_{1-30}$ organyl. In some embodiments, $R^3$ is $C_{1-3}$ alkyl optionally substituted with 1 to 6 $R^{8A}$ groups, wherein each $R^{8A}$ group is independently OH, oxide, $C_{1-6}$ organyl, or —O—($C_{1-6}$ organyl).

Embodiment 3. The compound of embodiment 1, further represented by a formula:

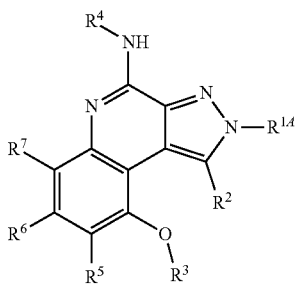

or a salt thereof,
wherein $R^4$ is H, $C_{1-30}$ non-aromatic organyl, or $C_{1-30}$ aromatic organyl containing an aromatic group that is not directly attached to the N atom.

Embodiment 4. The compound of embodiment 1, 2 or 3, wherein $R^1$ or $R^{14}$ is $C_{1-12}$ optionally substituted alkyl.

Embodiment 5. The compound of embodiment 4, wherein $R^1$ or $R^{14}$ is —$C_rH_{2r+10}$, or an ester thereof, wherein r is 1, 2, 3, 4, 5, 6, 7, 8, 9, or 10.

Embodiment 6. The compound of embodiment 5, wherein $R^1$ or $R^{14}$ is —$C_3H_7O$.

Embodiment 7. The compound of embodiment 6, wherein $R^1$ or $R^{14}$ is —$CH_2OCH_2CH_3$.

Embodiment 8. The compound of embodiment 1, 2, 3, 4, 5, 6, or 7, wherein $R^2$ or $R^{2A}$ is H or $C_{1-12}$ optionally substituted alkyl.

Embodiment 9. The compound of embodiment 8, wherein $R^2$ or $R^{2A}$ is $C_{1-6}$ alkyl, or —$C_yH_{2y+10}$ or an ester thereof, wherein y is 1, 2, 3, 4, 5, 6, 7, 8, 9, or 10.

Embodiment 10. The compound of embodiment 9, wherein $R^2$ or $R^{2A}$ is —$C_4H_9O$.

Embodiment 11. The compound of embodiment 10, wherein $R^2$ or $R^{2A}$ is —$CH_2$—$CH(CH_3)_2$—OH.

Embodiment 12. The compound of embodiment 8, wherein $R^2$ or $R^{2A}$ is H.

Embodiment 13. The compound of embodiment 1, 2, 3, 4, 5, 6, 7, 8, 9, 10, 11, or 12, wherein $R^3$ is $C_{1-30}$ optionally substituted alkyl.

Embodiment 14. The compound of embodiment 13, wherein $R^3$ is $C_{1-10}$ alkyl, or —$C_wH_{2w+10}$ or an ester thereof, wherein w is 1, 2, 3, 4, 5, 6, 7, 8, 9, or 10.

Embodiment 15. The compound of embodiment 1, 2, 3, 4, 5, 6, 7, 8, 9, 10, 11, 12, or 13, wherein $R^3$ is —($C_tH_{2t}O_{0-1}$)—Ht, wherein t is 0, 1, 2, 3, 4, 5, 6, 7, 8, 9, or 10, and Ht is optionally substituted $C_{3-6}$ heterocyclyl.

Embodiment 16. The compound of embodiment 1, 2, 3, 4, 5, 6, 7, 8, 9, 10, 11, 12, or 13, wherein $R^3$ is —($C_uH_{2u}O_{0-1}$)—Z—($C_nH_{2v+1}$), wherein Z is a bond, 0, $NHSO_2$, or NHCO, u is 0, 1, 2, 3, 4, 5, or 6, and v is 1, 2, 3, 4, 5, 6, 7, 8, 9, 10, 11, 12, 13, 14, 15, 16, 17, 18, 19, 20, 21, 22, or 23.

Embodiment 17. The compound of embodiment 1, 2, 3, 4, 5, 6, 7, 8, 9, 10, 11, 12, or 13, wherein $R^3$ is —($C_uH_{2u}O_{0-1}$)—$NR^aR^b$, and u is 1, 2, 3, 4, 5, or 6, wherein $R^a$ and R are independently H or $C_{1-6}$ alkyl.

Embodiment 18. The compound of embodiment 14, wherein $R^3$ is $C_5H_{11}O$.

Embodiment 19. The compound of embodiment 18, wherein $R^3$ is —$CH_2$—$CH_2$—$CH(CH_3)_2OH$.

Embodiment 20. The compound of embodiment 17, wherein $R^3$ is —$CH_2$—$CH_2$—$CH_2$—$NH_2$.

Embodiment 21. The compound of embodiment 1, 2, 3, 4, 5, 6, 7, 8, 9, 10, 11, 12, 13, 14, 15, 16, 17, 18, 19, or 20, wherein $R^4$ is H or $C_{1-6}$ alkyl.

Embodiment 22. The compound of embodiment 21, wherein $R^4$ is H.

Embodiment 23. The compound of embodiment 1, 2, 3, 4, 5, 6, 7, 8, 9, 10, 11, 12, 13, 14, 15, 16, 17, 18, 19, 20, 21, or 22, wherein $R^5$ is $R^a$, F, Cl, —$CO_2R^a$, —$CONR^aR^b$, CN, —$OR^a$, —$NR^aR^b$, —$OCOR^a$, or —$SO_2R^a$, wherein $R^a$ and R are independently H or $C_{1-6}$ alkyl.

Embodiment 24. The compound of embodiment 23, wherein $R^5$ is H.

Embodiment 25. The compound of embodiment 1, 2, 3, 4, 5, 6, 7, 8, 9, 10, 11, 12, 13, 14, 15, 16, 17, 18, 19, 20, 21, or 22, wherein $R^5$ is —($C_mH_{2m}O_{0-1}$)—Z—($C_nH_{2n+1}$), wherein Z is a bond, 0, $NHSO_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, 23, 24 or 25.

Embodiment 26. The compound of embodiment 1, 2, 3, 4, 5, 6, 7, 8, 9, 10, 11, 12, 13, 14, 15, 16, 17, 18, 19, 20, 21, 22, 23, 24, or 25, wherein $R^6$ is $R^a$, F, Cl, —$CO_2R^a$, —$CONR^aR^b$, CN, —$OR^a$, —$NR^aR^b$, —$OCOR^a$, or —$SO_2R^a$, wherein $R^a$ and R are independently H or $C_{1-6}$ alkyl.

Embodiment 27. The compound of embodiment 26, wherein $R^6$ is H.

Embodiment 28. The compound of embodiment 1, 2, 3, 4, 5, 6, 7, 8, 9, 10, 11, 12, 13, 14, 15, 16, 17, 18, 19, 20, 21, 22, 23, 24 or 25, wherein $R^6$ is —($C_mH_{2m}O_{0-1}$)—Z—($C_nH_{2n+1}$), wherein Z is a bond, O, $NHSO_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, or 23.

Embodiment 29. The compound of embodiment 1, 2, 3, 4, 5, 6, 7, 8, 9, 10, 11, 12, 13, 14, 15, 16, 17, 18, 19, 20, 21, 22, 23, 24, 25, 26, 27 or 28, wherein $R^7$ is $R^a$, F, Cl, —$CO_2R^a$, —$CONR^aR^b$, CN, —$OR^a$, —$NR^aR^b$, —$OOR^a$, or —$SO_2R^a$, wherein $R^a$ and R are independently H or $C_{1-6}$ alkyl.

Embodiment 30. The compound of embodiment 29, wherein $R^7$ is H.

Embodiment 31. The compound of embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein $R^7$ is $-(C_mH_{2m}O_{0-1})-Z-(C_nH_{2n+1})$, wherein Z is a bond, O, NHSO$_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, or 23.

Embodiment 32. The compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, $R^8$ is H, OH, or CH$_3$.

Embodiment 33. The compound of embodiment 32, wherein $R^8$ is OH.

Embodiment 34. The compound of embodiment 32, wherein $R^8$ is H.

Embodiment 35. A compound, which is:

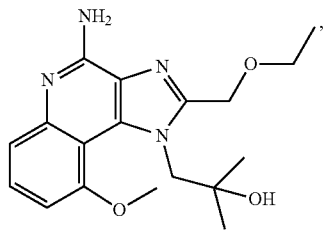

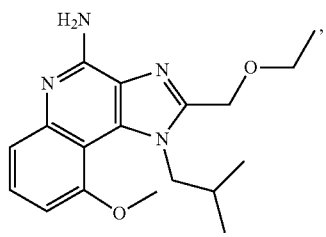

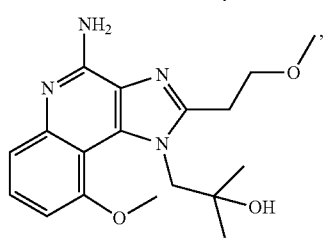

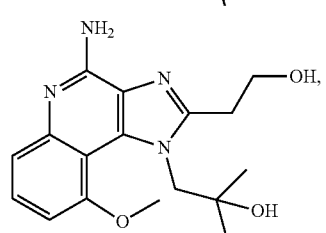

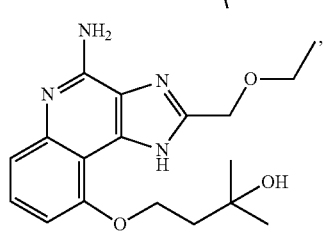

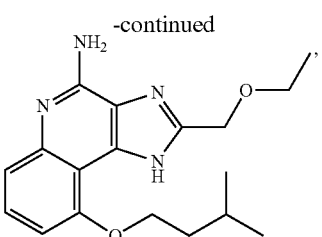

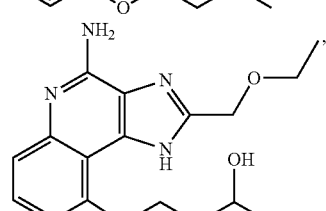

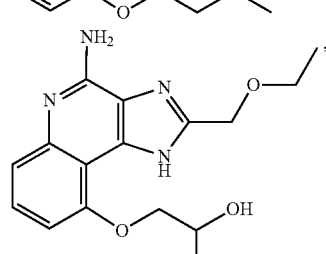

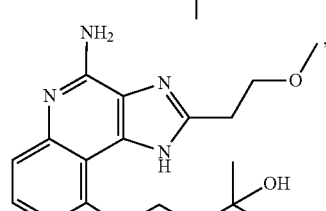

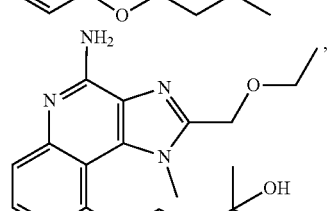

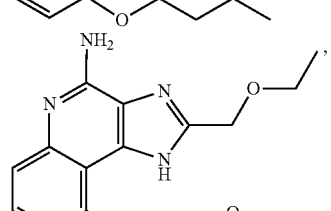

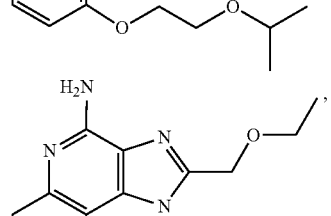

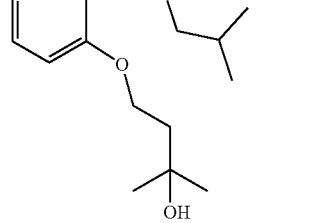

-continued
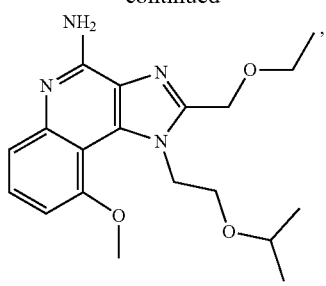
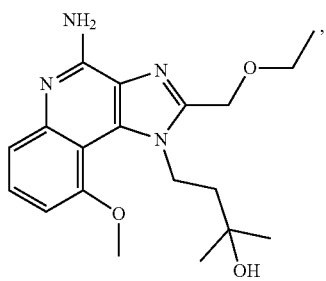
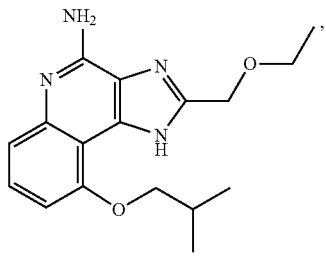
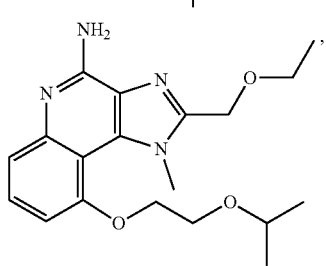
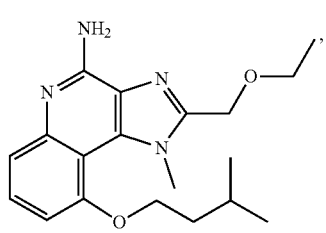
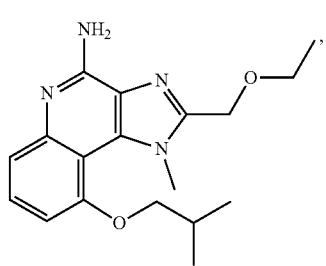
-continued
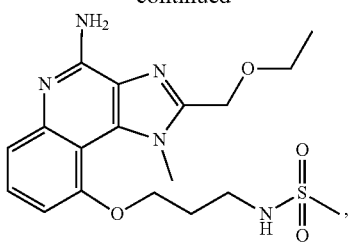
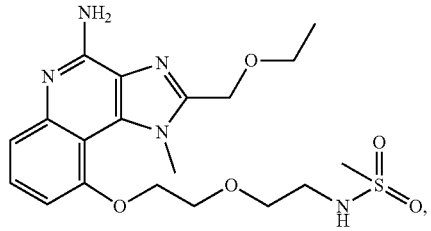
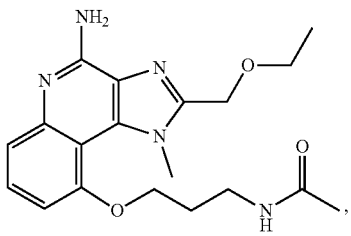
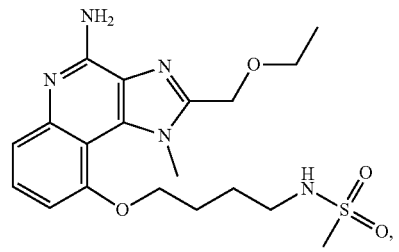
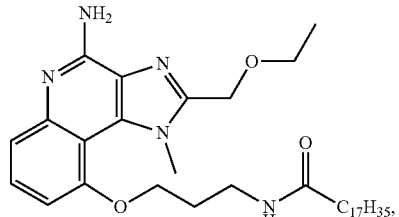
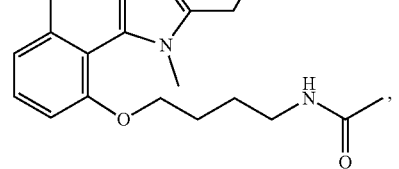
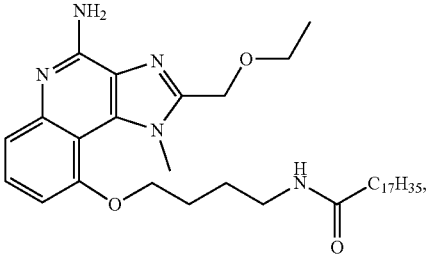

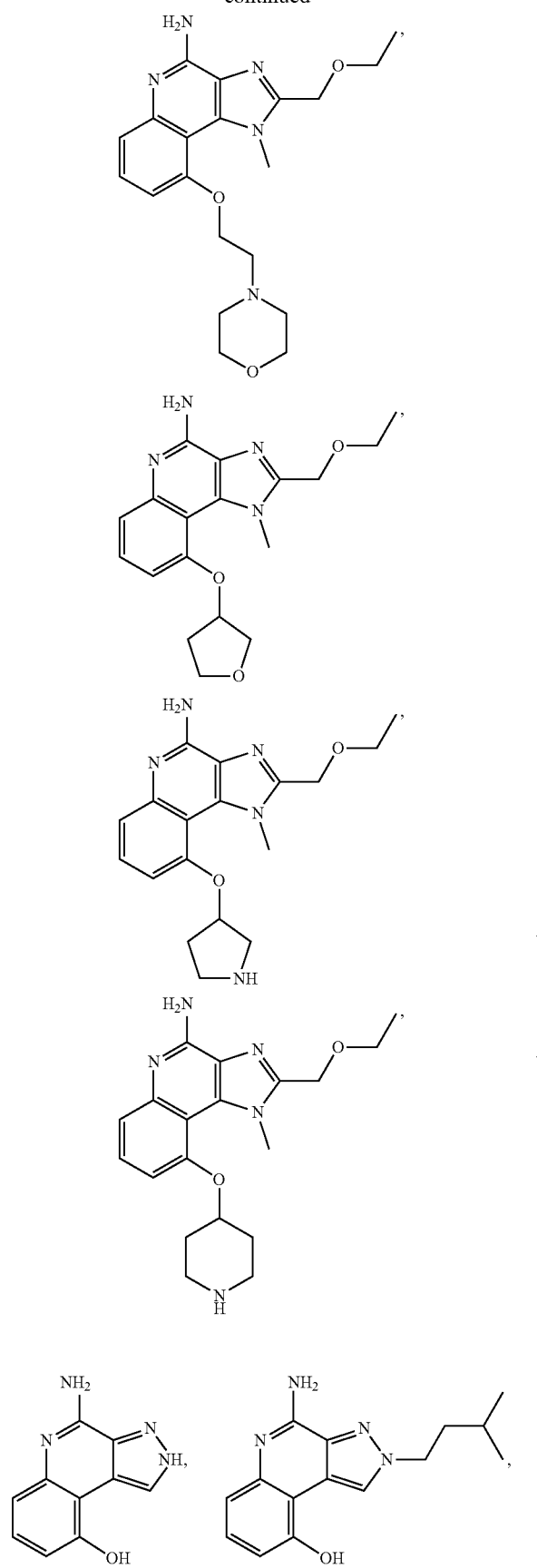
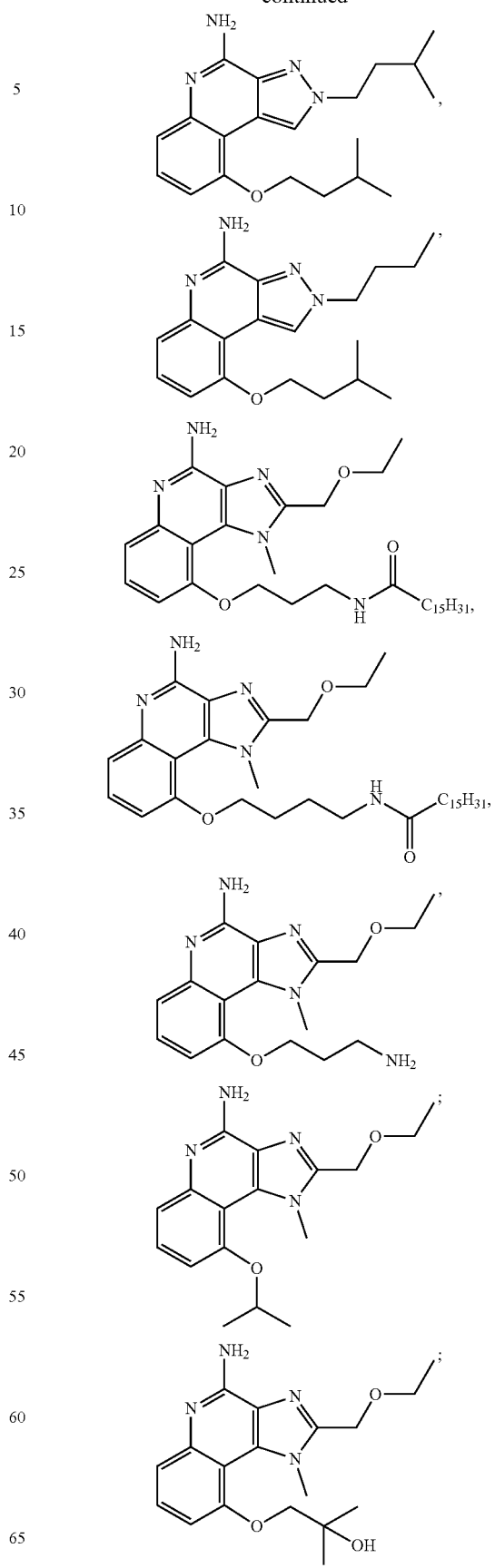

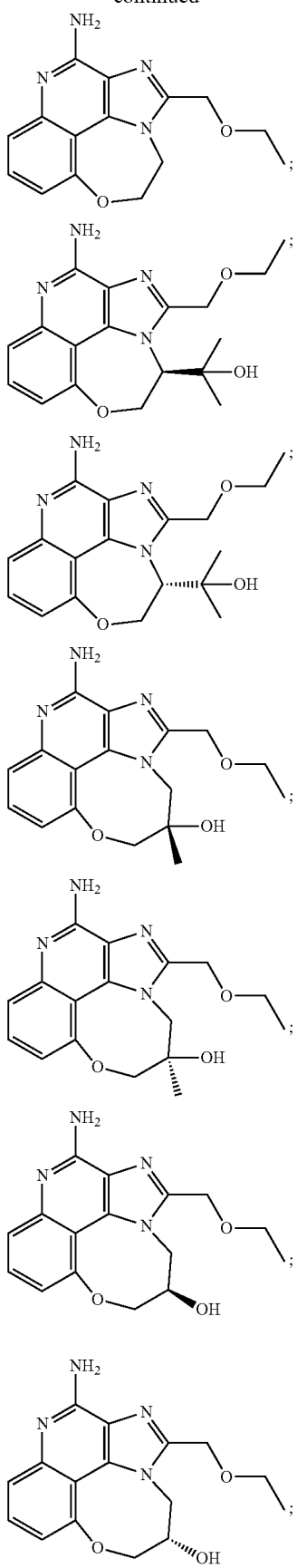

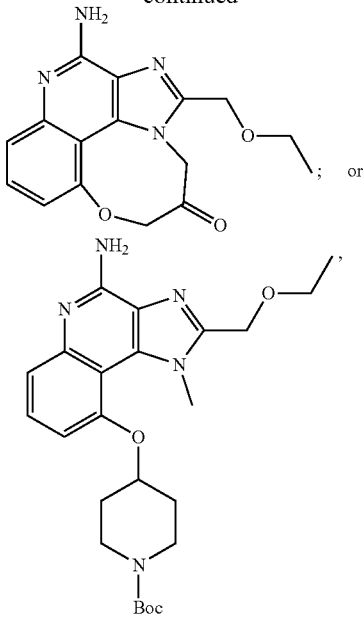

a salt of any of these compounds, or an ester of any of these compounds having an —OH group.

Embodiment 36. A compound which is optionally substituted 9-methoxy-1H-imidazo[4,5-c]quinolin-4-amine.

Embodiment 37. A compound which is optionally substituted 9-methoxy-2H-pyrazolo[3,4-c]quinolin-4-amine.

Embodiment 38. The compound of embodiment 36, which is optionally substituted 1-(4-amino-2-(ethoxymethyl)-9-methoxy-1H-imidazo[4,5-c]quinolin-1-yl)-2-methylpropan-2-ol or a salt thereof, optionally substituted 2-(ethoxymethyl)-1-isobutyl-9-methoxy-1H-imidazo[4,5-c]quinolin-4-amine or a salt thereof, optionally substituted 1-(4-amino-9-methoxy-2-(2-methoxyethyl)-1H-imidazo[4,5-c]quinolin-1-yl)-2-methylpropan-2-ol or a salt thereof, optionally substituted 1-(4-amino-2-(2-hydroxyethyl)-9-methoxy-1H-imidazo[4,5-c]quinolin-1-yl)-2-methylpropan-2-ol or a salt thereof, optionally substituted 4-((4-amino-2-(ethoxymethyl)-1H-imidazo[4,5-c]quinolin-9-yl)oxy)-2-methylbutan-2-ol or a salt thereof, optionally substituted 2-(ethoxymethyl)-9-(isopentyloxy)-1H-imidazo[4,5-c]quinolin-4-amine or a salt thereof, optionally substituted 4-((4-amino-2-(ethoxymethyl)-1H-imidazo[4,5-c]quinolin-9-yl)oxy)butan-2-ol or a salt thereof, optionally substituted 1-((4-amino-2-(ethoxymethyl)-1H-imidazo[4,5-c]quinolin-9-yl)oxy)propan-2-ol or a salt thereof, optionally substituted 4-((4-amino-2-(2-methoxyethyl)-1H-imidazo[4,5-c]quinolin-9-yl)oxy)-2-methylbutan-2-ol or a salt thereof, optionally substituted 4-((4-amino-2-(ethoxymethyl)-1-methyl-1H-imidazo[4,5-c]quinolin-9-yl)oxy)-2-methylbutan-2-ol or a salt thereof, optionally substituted 2-(ethoxymethyl)-9-(2-isopropoxyethoxy)-1H-imidazo[4,5-c]quinolin-4-amine or a salt thereof, optionally substituted 4-((4-amino-2-(ethoxymethyl)-1-isobutyl-1H-imidazo[4,5-c]quinolin-9-yl)oxy)-2-methylbutan-2-ol or a salt thereof, optionally substituted 2-(ethoxymethyl)-1-(2-isopropoxyethyl)-9-methoxy-1H-imidazo[4,5-c]quinolin-4-amine or a salt thereof, optionally substituted 4-(4-amino-2-(ethoxymethyl)-9-methoxy-1H-imidazo[4,5-c]quinolin-1-yl)-2-methylbutan-2-ol or a salt thereof, optionally substituted 2-(ethoxymethyl)-9-isobutoxy-1H-imidazo[4,5-c]quinolin-4-amine or a salt thereof, optionally substituted 2-(ethoxymethyl)-9-(2- isopropoxyethoxy)-1-methyl-1H-imidazo[4,5-c]quinolin-4-amine or a salt thereof, optionally substituted 2-(ethoxymethyl)-9-(isopentyloxy)-1-methyl-1H-imidazo[4,5-c]quinolin-4-amine or a salt thereof, optionally substituted 2-(ethoxymethyl)-9-isobutoxy-1-methyl-1H-imidazo[4,5-c]quinolin-4-amine or a salt thereof, optionally substituted N-(3-((4-amino-2-(ethoxymethyl)-1-methyl-1H-imidazo[4,5-c]quinolin-9-yl)oxy)propyl)methanesulfonamide or a salt thereof, optionally substituted N-(2-(2-((4-amino-2-(ethoxymethyl)-1-methyl-1H-imidazo[4,5-c]quinolin-9-yl)oxy)ethoxy)ethyl)-methanesulfonamide or a salt thereof, optionally substituted N-(3-((4-amino-2-(ethoxymethyl)-1-methyl-1H-imidazo[4,5-c]quinolin-9-yl)oxy)propyl)acetamide or a salt thereof, optionally substituted N-(4-((4-amino-2-(ethoxymethyl)-1-methyl-1H-imidazo[4,5-c]quinolin-9-yl)oxy)butyl)methane-sulfonamide or a salt thereof, optionally substituted N-(3-((4-amino-2-(ethoxymethyl)-1-methyl-1H-imidazo[4,5-c]quinolin-9-yl)oxy)propyl)stearamide or a salt thereof, optionally substituted N-(4-((4-amino-2-(ethoxymethyl)-1-methyl-1H-imidazo[4,5-c]quinolin-9-yl)oxy)butyl)acetamide or a salt thereof, optionally substituted N-(4-((4-amino-2-(ethoxymethyl)-1-methyl-1H-imidazo[4,5-c]quinolin-9-yl)oxy)butyl)stearamide or a salt thereof, optionally substituted 2-(ethoxymethyl)-1-methyl-9-(2-morpholinoethoxy)-1H-imidazo[4,5-c]quinolin-4-amine or a salt thereof, optionally substituted 2-(ethoxymethyl)-1-methyl-9-((tetrahydrofuran-3-yl)oxy)-1H-imidazo[4,5-c]quinolin-4-amine or a salt thereof, optionally substituted 2-(ethoxymethyl)-1-methyl-9-(pyrrolidin-3-yloxy)-1H-imidazo[4,5-c]quinolin-4-amine or a salt thereof, optionally substituted 2-(ethoxymethyl)-1-methyl-9-(piperidin-4-yloxy)-1H-imidazo[4,5-c]quinolin-4-amine or a salt thereof, optionally substituted N-(3-((4-amino-2-(ethoxymethyl)-1-methyl-1H-imidazo[4,5-c]quinolin-9-yl)oxy)propyl)palmitamide or a salt thereof, optionally substituted N-(4-((4-amino-2-(ethoxymethyl)-1-methyl-1H-imidazo[4,5-c]quinolin-9-yl)oxy)butyl)palmitamide or a salt thereof, optionally substituted 9-(3-aminopropoxy)-2-(ethoxymethyl)-1-methyl-1H-imidazo[4,5-c]quinolin-4-amine or a salt thereof, optionally substituted 2-(ethoxymethyl)-9-isopropoxy-1-methyl-1H-imidazo[4,5-c]quinolin-4-amine or a salt thereof, optionally substituted 1-((4-amino-2-(ethoxymethyl)-1-methyl-1H-imidazo[4,5-c]quinolin-9-yl)oxy)-2-methylpropan-2-ol or a salt thereof, optionally substituted 2-(ethoxymethyl)-3,4-dihydro-5-oxa-1,2a,9-triazanaphtho[2,1,8-cde]azulen-10-amine or a salt thereof; optionally substituted (R)-2-(10-amino-2-(ethoxymethyl)-3,4-dihydro-5-oxa-1,2a,9-triazanaphtho[2,1,8-cde]azulen-3-yl)propan-2-ol or a salt thereof, optionally substituted (S)-2-(10-amino-2-(ethoxymethyl)-3,4-dihydro-5-oxa-1,2a,9-triazanaphtho[2,1,8-cde]azulen-3-yl)propan-2-ol or a salt thereof, optionally substituted (S)-2-amino-12-(ethoxymethyl)-6-methyl-6,7-dihydro-5H-3,4-(azenometheno)[1,5]oxazocino[4,3,2-de]quinolin-6-ol or a salt thereof, optionally substituted (R)-2-amino-12-(ethoxymethyl)-6-methyl-6,7-dihydro-5H-3,4-(azenometheno)[1,5]oxazocino[4,3,2-de]quinolin-6-ol or a salt thereof, optionally substituted (R)-2-amino-12-(ethoxymethyl)-6,7-dihydro-5H-3,4-(azenometheno)[1,5]oxazocino[4,3,2-de]quinolin-6-ol or a salt thereof, optionally substituted (S)-2-amino-12-(ethoxymethyl)-6,7-dihydro-5H-3,4-(azenometheno)[1,5]oxazocino-[4,3,2-de]quinolin-6-ol or a salt thereof, optionally substituted 2-amino-12-(ethoxymethyl)-5H-3,4-(azenometheno)[1,5]oxazocino[4,3,2-de]quinolin-6(7H)-one or a salt thereof, or optionally substituted tert-butyl 4-((4-amino-2-(ethoxymethyl)-1-methyl-1H-imidazo[4,5-c]quinolin-9-yl)oxy)piperidine-1-carboxylate or a salt thereof.

Embodiment 39. The compound of embodiment 37 which is optionally substituted 4-amino-2H-pyrazolo[3,4-c]quinolin-9-ol or a salt thereof, optionally substituted 4-amino-2-isopentyl-2H-pyrazolo[3,4-c]quinolin-9-ol or a salt thereof, optionally substituted 2-isopentyl-9-(isopentyloxy)-2H-pyrazolo[3,4-c]quinolin-4-amine or a salt thereof, or optionally substituted 2-butyl-9-(isopentyloxy)-2H-pyrazolo[3,4-c]quinolin-4-amine or a salt thereof.

Embodiment 40. A method of treating viral infection, cancer, or an allergic disease, comprising administering a compound according to embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, or 39, to a mammal in need thereof.

Embodiment 41. Use of a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, in the manufacture of a medicament for the treatment of viral infection, cancer, or an allergic disease.

Embodiment 42. The method of embodiment 40 or use of embodiment 41, wherein the viral infection comprises HCV infection.

Embodiment 43. A dosage form suitable for administration to a mammal, comprising a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39.

EXAMPLES

In the synthetic schemes described below, unless otherwise indicated all temperatures are set forth in degrees Celsius and all parts and percentages are by weight. Reagents and solvents were purchased from commercial suppliers such as Aldrich Chemical Company and were used without further purification unless otherwise indicated. Tetrahydrofuran (THF) and N,N-dimethylforamide (DMF) were purchased from commercial sources in Sure Seal bottles and used as received.

The reactions set forth below were done generally under a positive pressure of argon or nitrogen at an ambient temperature (unless otherwise stated) in anhydrous solvents. Glassware was oven dried and/or heat dried. The reactions were assayed by TLC and/or analyzed by LC-MS and terminated as judged by the consumption of starting material. Analytical thin layer chromatography (TLC) was performed on glass plates pre-coated with silica gel 60 F254 0.25 mm plates (EM Science), and visualized with UV light (254 nm) and/or heating with commercial ethanolic phosphomolybdic acid. Preparative thin layer chromatography (TLC) was performed on glass-plates pre-coated with silica gel 60 F254 0.5 mm plates (20×20 cm, from commercial sources) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel.

$^1$H-NMR spectra and $^{13}$C-NMR were recorded on a Varian Mercury-VX400 instrument operating at 400 MHZ. NMR spectra were obtained as $CDCl_3$ solutions (reported in ppm), using chloroform as the reference standard (7.27 ppm for the proton and 77.00 ppm for carbon), CD$_3$OD (3.4 and 4.8 ppm for the protons and 49.3 ppm for carbon), DMSO-d$_6$ (2.49 ppm for proton), or internally tetramethylsilane (0.00 ppm) when appropriate. Other NMR solvents were used as needed.

Example 1

Synthesis of 1-[4-Amino-2-(ethoxymethyl)-9-methoxy-imidazo[4,5-c]quinolin-1-yl]-2-methyl-propan-2-ol

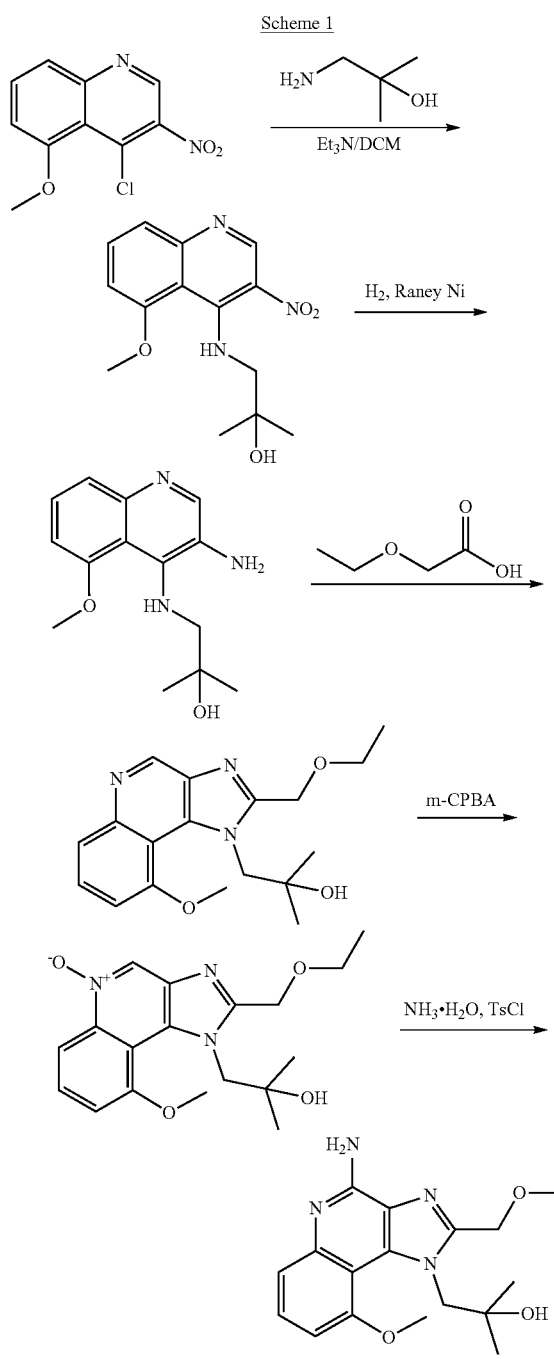

Scheme 1

Step 1: Synthesis of 1-[(5-Methoxy-3-nitro-4-quinolyl)amino]-2-methyl-propan-2-ol To a solution of 1-amino-2-methyl-propan-2-ol (747.10 mg, 8.38 mmol, 2.0 eq.) and Et$_3$N (2.12 g, 20.95 mmol, 2.90 mL, 5.0 eq.) in DCM (50.00 mL) was added 4-chloro-5-methoxy-3-nitro-quinoline (1.00 g, 4.19 mmol, 1.0 eq.). The resulting mixture was stirred at 25° C. for 0.5 h. The reaction mixture was washed with water (30 mL) and brine (30 mL) via extraction. The organic phase was dried over anhydrous Na$_2$SO$_4$, filtered, and concentrated in vacuo. The residue was purified with column chromatography (DCM to DCM/MeOH=20/1). The desired product of 1-[(5-methoxy-3-nitro-4-quinolyl)amino]-2-methyl-propan-2-ol (1.00 g, 3.43 mmol, 81.86% yield) was obtained as a yellow solid. $^1$H NMR (400 MHz, CDCl$_3$) δ ppm: 9.51 (s, 1H), 9.03 (s, 1H), 7.63 (t, J=8.0 Hz, 1H), 7.58 (d, J=8.4 Hz, 1H), 6.94 (d, J=7.2 Hz, 1H), 4.10 (s, 3H), 2.95 (d, J=4.8 Hz, 2H), 1.29 (s, 6H); ES-LCMS m z 292.3 [M+H]$^+$.

Step 2: Synthesis of 1-[(3-Amino-5-methoxy-4-quinolyl)amino]-2-methyl-propan-2-ol To a solution of 1-[(5-methoxy-3-nitro-4-quinolyl)amino]-2-methyl-propan-2-ol (1.00 g, 3.43 mmol, 1.0 eq.) in MeOH (100.00 mL) was added Raney-Ni (626.42 mg, 7.31 mmol, 2.1 eq.) under N$_2$. The suspension was degassed under vacuum and purged with H$_2$ several times. The resulting mixture was stirred under H$_2$ (15 psi) at 25° C. for 3 h. The reaction mixture was filtered. The filtrate was concentrated in vacuo. The desired product of 1-[(3-amino-5-methoxy-4-quinolyl)amino]-2-methyl-propan-2-ol (870.00 mg, 3.33 mmol, 97.08% yield) was obtained as a yellow solid. $^1$H NMR (400 MHz, CD$_3$OD) δ ppm: 8.26 (s, 1H), 7.38 (d, J=8.0 Hz, 1H), 7.31 (t, J=8.0 Hz, 1H), 6.88 (d, J=7.6 Hz, 1H), 4.02 (s, 3H), 3.22 (s, 2H), 1.29 (s, 6H); ES-LCMS m z 262.3 [M+H]$^+$.

Step 3: Synthesis of 1-[2-(Ethoxymethyl)-9-methoxy-imidazo[4,5-c]quinolin-1-yl]-2-methyl-propan-2-ol A solution of 1-[(3-amino-5-methoxy-4-quinolyl)amino]-2-methyl-propan-2-ol (400.00 mg, 1.53 mmol, 1.0 eq.) and 4 Å MS (200 mg) in 2-ethoxyacetic acid (3.30 g, 31.7 mmol, 3 mL, 20.7 eq.) was stirred at 120° C. for 4 h under microwave. The reaction mixture was then filtered. The filtrate was dissolved in DCM (80 mL) and adjusted to pH=8 with 2 M NaOH. The organic layer was separated and dried over anhydrous Na$_2$SO$_4$, filtered and concentrated in vacuo. The mixture was purified with column chromatography (DCM to DCM/MeOH=10/1). The desired product of 1-[2-(ethoxymethyl)-9-methoxy-imidazo[4,5-c]quinolin-1-yl]-2-methyl-propan-2-ol (230.00 mg, 698.26 μmol, 45.62% yield) was obtained as a yellow solid. $^1$H NMR (400 MHz, CD$_3$OD) δ ppm: 9.09 (s, 1H), 7.79 (d, J=8.0 Hz, 1H), 7.67 (t, J=8.2 Hz, 1H), 7.25 (d, J=7.2 Hz, 1H), 5.68 (s, 1H), 5.39 (s, 1H), 4.63 (m, 2H), 4.14 (s, 3H), 3.62 (m, 2H), 1.32-1.26 (m, 3H), 1.25-1.23 (m, 3H), 0.76 (m, 3H); ES-LCMS m/z: 330.3 [M+H]$^+$.

Step 4: Synthesis of 1-[2-(Ethoxymethyl)-9-methoxy-5-oxido-imidazo[4,5-c]quinolin-5-ium-1-yl]-2-methyl-propan-2-ol To a solution of 1-[2-(ethoxymethyl)-9-methoxy-imidazo[4,5-c]quinolin-1-yl]-2-methyl-propan-2-ol (230.00 mg, 698.26 µmol, 1.0 eq.) in DCM (30.00 mL) was added m-CPBA (212.64 mg, 1.05 mmol, 85% purity, 1.5 eq.). The resulting mixture was stirred at 25° C. for 1 h. The reaction mixture was then adjusted to pH=8 with aqueous $K_2CO_3$ and partitioned between DCM (50 mL) and water (20 mL). The organic layer was separated, washed with brine (20 mL), dried over $Na_2SO_4$, and filtered. After filtration, the filtrate was concentrated in vacuo. The residue was purified with prep-TLC (DCM/MeOH=8/1, $R_f$=0.3). The desired product of 1-[2-(ethoxymethyl)-9-methoxy-5-oxido-imidazo[4,5-c] quinolin-5-ium-1-yl]-2-methyl-propan-2-ol (150.00 mg, 434.29 µmol, 62.20% yield) was obtained as a yellow solid. $^1$H NMR (400 MHz, $CD_3OD$) δ ppm: 9.10 (s, 1H), 8.52 (d, J=8.8 Hz, 1H), 7.85 (t, J=8.6 Hz, 1H), 7.45 (d, J=7.6 Hz, 1H), 5.54 (s, 1H), 5.31 (s, 1H), 4.58 (s, 2H), 4.19 (s, 3H), 3.62 (m, 2H), 1.28-1.23 (m, 6H), 0.84 (m, 3H); ES-LCMS m/z: 346.3 $[M+H]^+$.

Step 5: Synthesis of 1-[4-Amino-2-(ethoxymethyl)-9-methoxy-imidazo[4,5-c]quinolin-1-yl]-2-methyl-propan-2-ol To a solution of 1-[2-(ethoxymethyl)-9-methoxy-5-oxido-imidazo[4,5-c]quinolin-5-ium-1-yl]-2-methyl-propan-2-ol (150.00 mg, 434.29 µmol, 1.0 eq.) and $NH_3·H_2O$ (543.64 mg, 4.34 mmol, 597.41 µL, 28% purity, 10.0 eq.) in $CHCl_3$ (20.00 mL) was added TsCl (99.36 mg, 521.15 µmol, 1.2 eq.). The resulting mixture was stirred at 20° C. for 0.5 h. The solvent was removed in vacuo. The residue was purified with prep-HPLC (MeCN/$H_2O$ as eluents, acidic condition). After lyophilization, the desired product of 1-[4-amino-2-(ethoxymethyl)-9-methoxy-imidazo[4,5-c]quinolin-1-yl]-2-methyl-propan-2-ol (50.00 mg, 131.28 µmol, 30.23% yield, 100% purity, as HCl salt) was obtained as a white solid. $^1$H NMR (400 MHz, $CD_3OD$) δ ppm: 7.63 (t, J=8.2 Hz, 1H), 7.30 (d, J=8.0 Hz, 1H), 7.13 (d, J=8.0 Hz, 1H), 5.50 (s, 1H), 5.21 (s, 1H), 4.76 (s, 1H), 4.55 (s, 1H), 4.09 (s, 3H), 3.59 (m, 2H), 1.23-1.20 (m, 6H), 0.82 (m, 3H); ES-LCMS m/z: 345.3 $[M+H]^+$ Example 2

Synthesis of 2-(Ethoxymethyl)-1-isobutyl-9-methoxy-imidazo[4,5-c]quinolin-4-amine Scheme 2

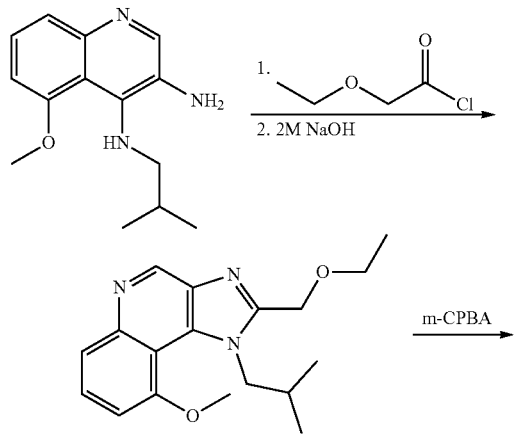

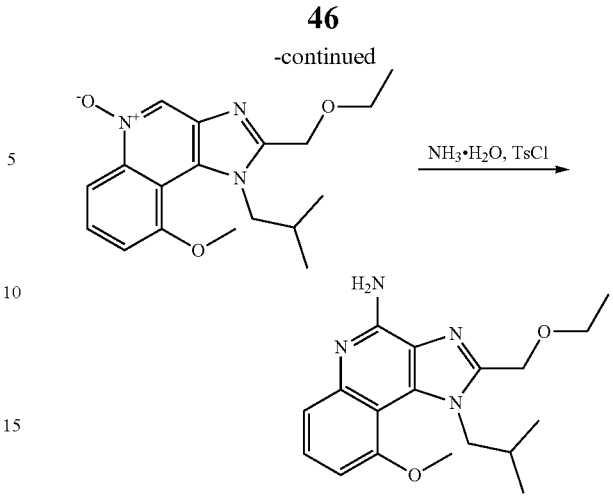

Step 1: Synthesis of 2-(Ethoxymethyl)-1-isobutyl-9-methoxy-imidazo[4,5-c]quinoline To a solution of $N^4$-isobutyl-5-methoxy-quinoline-3,4-diamine (100.00 mg, 407.63 µmol, 1.0 eq.) and pyridine (322.44 mg, 4.08 mmol, 329.02 µL, 10.0 eq.) in DCM (4.00 mL) was added 2-ethoxyacetyl chloride (99.91 mg, 815.26 µmol, 2.0 eq.). The resulting mixture was stirred at 25° C. for 1 h. The solvent was removed in vacuo. The residue was dissolved in NaOH (2 M, 4.95 mL, 24.3 eq.) and stirred at 100° C. for 5 h. The mixture was dissolved in water (10 mL) and extracted with DCM (50 mL×2).

The combined organic phase was washed with brine (20 mL), dried over anhydrous $Na_2SO_4$, filtered and concentrated in vacuo. The residue was purified with prep-TLC (DCM/MeOH=15/1). The desired product of 2-(ethoxymethyl)-1-isobutyl-9-methoxy-imidazo[4,5-c]quinoline (80.00 mg, 255.27 µmol, 62.62% yield) was obtained as a brown solid. $^1$H NMR (400 MHz, $CDCl_3$) δ ppm: 9.27 (s, 1H), 7.70 (d, J=8.4 Hz, 1H), 7.60 (t, J=8.2 Hz, 1H), 7.04 (d, J=8.0 Hz, 1H), 4.89 (s, 2H), 4.62 (br, s. 2H), 4.08 (s, 3H), 3.65-3.59 (m, 2H), 2.11-2.02 (m, 1H), 1.26 (t, J=7.0 Hz, 3H), 0.75-0.72 (m, 6H); ES-LCMS m/z: 314.3 $[M+H]^+$.

Step 2: 2-(Ethoxymethyl)-1-isobutyl-9-methoxy-5-oxido-imidazo[4,5-c]quinolin-5-ium To a solution of 2-(ethoxymethyl)-1-isobutyl-9-methoxy-imidazo[4,5-c]quinoline (50.00 mg, 159.55 µmol, 1.0 eq.) in DCM (5.00 mL) was added m-CPBA (48.59 mg, 239.33 µmol, 85% purity, 1.5 eq.). The resulting mixture was stirred at 25° C. for 0.5 h. DCM (40 mL) and water (10 mL) were added, and pH was adjusted to 8 by addition of aqueous NaOH. The organic layer was then separated, washed with brine (10 mL), dried over $Na_2SO_4$ and filtered. The filtrate was concentrated in vacuo. The desired product of 2-(ethoxymethyl)-1-isobutyl-9-methoxy-5-oxido-imidazo [4,5-c]quinolin-5-ium (50.00 mg, 151.80 µmol, 95.14% yield) was obtained as a yellow solid. $^1$H NMR (400 MHz, $CDCl_3$) δ ppm: 9.05 (s, 1H), 8.71 (d, J=8.8 Hz, 1H), 7.70 (t, J=8.2 Hz, 1H), 7.17 (d, J=7.2 Hz, 1H), 4.56 (s, 2H), 4.44 (br, s. 2H), 4.11 (s, 3H), 3.65-3.59 (m, 2H), 2.06-1.99 (m, 1H), 1.27 (t, J=7.0 Hz, 3H), 0.76-0.72 (m, 6H); ES-LCMS m/z: 330.2 $[M+H]^+$.

Step 3: 2-(Ethoxymethyl)-1-isobutyl-9-methoxy-imidazo[4,5-c]quinolin-4-amine

To a solution of 2-(ethoxymethyl)-1-isobutyl-9-methoxy-5-oxido-imidazo[4,5-c]-quinolin-5-ium (50.00 mg, 151.80

μmol, 1.0 eq.) and NH₃·H₂O (190.27 mg, 1.52 mmol, 209.09 μL, 28% purity, 10.0 eq.) in CHCl₃ (10.00 mL) was added TsCl (34.73 mg, 182.16 mol, 1.2 eq.). The resulting mixture was stirred at 25° C. for 0.5 h. The solvent was removed in vacuo. The residue was purified with prep-HPLC (MeCN/H₂O as eluents, acidic condition). After lyophilization, the desired product of 2-(ethoxymethyl)-1-isobutyl-9-methoxy-imidazo[4,5-c]quinolin-4-amine (30.00 mg, 78.31 μmol, 51.59% yield, 95.24% purity, as HCl salt) was obtained as a white solid. ¹H NMR (400 MHz, CD₃OD) δ ppm: 7.69 (t, J=8.2 Hz, 1H), 7.36 (d, J=8.0 Hz, 1H), 7.18 (d, J=8.4 Hz, 1H), 4.87 (s, 2H), 4.62 (br, s. 2H), 4.13 (s, 3H), 3.69-3.64 (m, 2H), 2.05-1.95 (m, 1H), 1.27 (t, J=7.0 Hz, 3H), 0.80-0.75 (m, 6H); ES-LCMS m/z: 329.4 [M+H]⁺.

The following compounds were prepared using the same method as that in Example 1 or 2 using corresponding reagents.

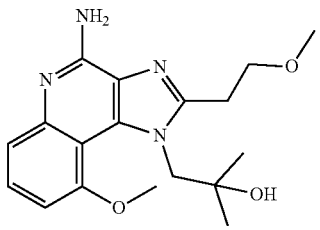 [SMILES: COCCc1nc2c(N)nc3cccc(OC)c3c2n1CC(C)(C)O]

1-[4-Amino-9-methoxy-2-(2-methoxyethyl)imidazo[4,5-c]quinolin-1-yl]-2-methyl-propan-2-ol was obtained as a white solid in 9.18% yield as a HCl salt with 98.5% purity. ¹H NMR (400 MHz, CD₃OD) δ ppm: 7.67 (t, J=8.4 Hz, 1H), 7.35 (d, J=8.4 Hz, 1H), 7.18 (d, J=8.4 Hz, 1H), 5.60 (m, 1H), 4.48 (m, 1H), 4.14 (s, 3H), 3.97 (m, 2H), 3.47-3.44 (m, 2H), 3.42 (s, 3H), 1.26 (s, 3H), 0.89 (s, 3H); ES-LCMS m/z: 345.3 [M+H]⁺.

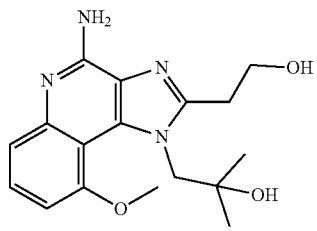 [SMILES: COc1cccc2nc(N)c3nc(CCO)n(CC(C)(C)O)c3c12]

1-[4-Amino-2-(2-hydroxyethyl)-9-methoxy-imidazo[4,5-c]quinolin-1-yl]-2-methyl-pro-pan-2-ol was obtained as a white solid in 3.47% yield as a HCl salt with 100% purity. ¹H NMR (400 MHz, CD₃OD) δ ppm: 7.61 (t, J=8.4 Hz, 1H), 7.28 (d, J=8.0 Hz, 1H), 7.12 (d, J=7.6 Hz, 1H), 5.54 (m, 1H), 4.41 (m, 1H), 4.08 (s, 3H), 4.07-4.05 (m, 2H), 3.27 (m, 2H), 1.20 (s, 3H), 0.85 (s, 3H); ES-LCMS m/z: 331.2 [M+H]⁺.

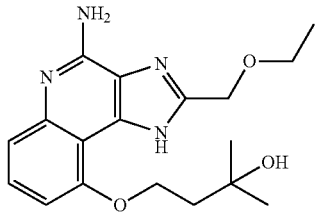 [SMILES: CCOCc1nc2c(N)nc3cccc(OCCC(C)(C)O)c3c2[nH]1]

4-[[4-Amino-2-(ethoxymethyl)-1H-imidazo[4,5-c]quinolin-9-yl]oxy]-2-methyl-butan-2-ol was obtained as a white solid in 40.57% yield as a HCl salt. H NMR (400 MHz, CD₃OD) δ ppm: 7.68 (t, J=8.4 Hz, 1H), 7.34 (d, J=8.4 Hz, 1H), 7.15 (d, J=8.4 Hz, 1H), 4.84 (s, 2H), 4.50 (t, J=6.0 Hz, 2H), 3.76-3.70 (m, 2H), 2.19 (t, J=5.8 Hz, 2H), 1.43 (s, 6H), 1.31 (t, J=7.0 Hz, 3H); ES-LCMS m/z: 345.3 [M+H]⁺.

Example 3

Synthesis of 2-(Ethoxymethyl)-9-isopentyloxy-1H-imidazo[4,5-c]quinolin-4-amine

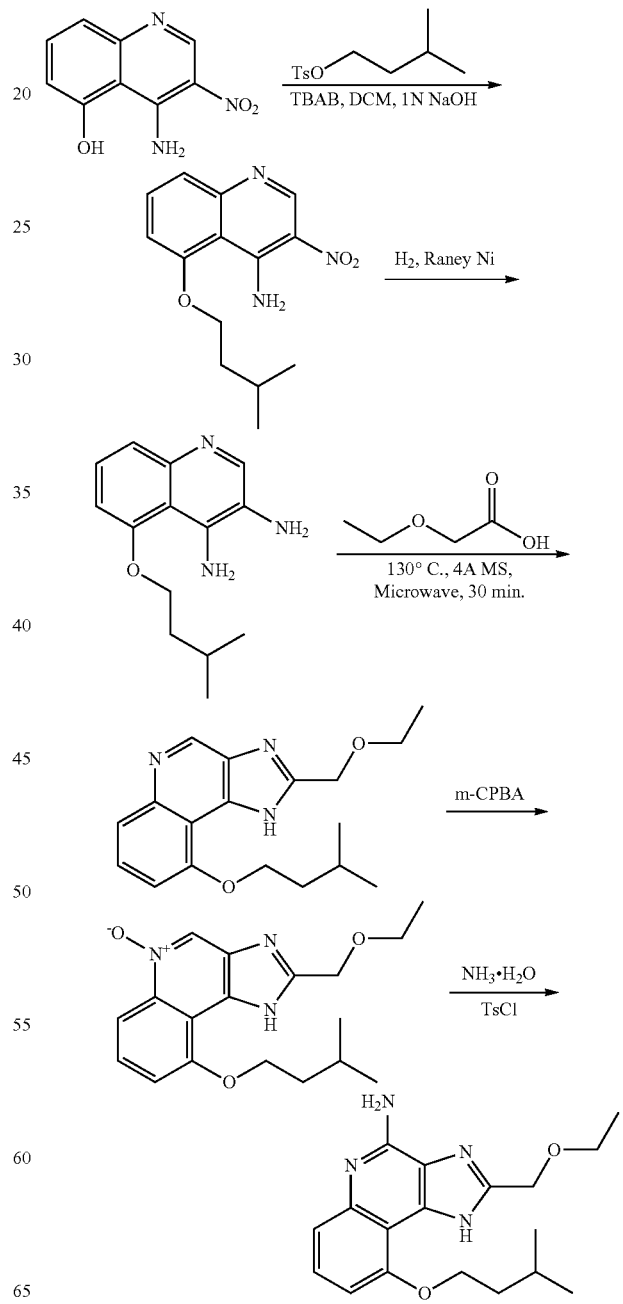

Scheme 3

Step 1: Synthesis of 5-Isopentyloxy-3-nitro-quinolin-4-amine

To a solution of 4-amino-3-nitro-quinolin-5-ol (300.00 mg, 1.46 mmol, 1.0 eq.), TBAB (470.66 mg, 1.46 mmol, 1.0 eq.) and KI (242.36 mg, 1.46 mmol, 1.0 eq.) in NaOH (1 M, 4.38 mL, 3.0 eq.) was added a solution of isopentyl 4-methylbenzenesulfonate (1.06 g, 4.38 mmol, 3.0 eq.) in DCM (4.00 mL). The resulting mixture was stirred at 20° C. for 40 h. The reaction mixture was diluted with $H_2O$ (10 mL) and extracted with DCM (30 mL×2). The combined organic layers were washed with brine (10 mL), dried over $Na_2SO_4$, filtered and concentrated under reduced pressure to give a residue. The residue was purified with column chromatography (PE to PE/EA=1/2). The desired product of 5-isopentyloxy-3-nitro-quinolin-4-amine (140.00 mg, 508.54 μmol, 34.83% yield) was obtained as a yellow solid. $^1$H NMR (400 MHz, $CDCl_3$) δ ppm: 9.33 (s, 1H), 9.25 (s, 1H), 9.10 (s, 1H), 7.66 (t, J=8.2 Hz, 1H), 7.57 (d, J=8.4 Hz, 1H), 6.94 (d, J=7.6 Hz, 1H), 4.28 (t, J=6.2 Hz, 2H), 1.88 (m, 3H), 1.05 (d, J=6.0 Hz, 6H); ES-LCMS m/z: 276.3 $[M+H]^+$.

Step 2: Synthesis of 5-Isopentyloxyquinoline-3,4-diamine

To a solution of 5-isopentyloxy-3-nitro-quinolin-4-amine (140.00 mg, 508.54 mol, 1.0 eq.) in MeOH (50.00 mL) was added Raney-Ni (100.00 mg, 1.17 mmol, 2.3 eq.) under $N_2$. The suspension was degassed under vacuum and purged with $H_2$ three times. The resulting mixture was stirred under $H_2$ (15 psi) at 20° C. for 2 h. The reaction mixture was filtered. The filtrate was concentrated in vacuo. The desired product of 5-isopentyloxyquinoline-3,4-diamine (120.00 mg, 489.16 μmol, 96.19% yield) was obtained as a green solid. $^1$H NMR (400 MHz, $CD_3OD$) δ ppm: 8.01 (s, 1H), 7.53 (t, J=8.2 Hz, 1H), 7.27 (d, J=8.8 Hz, 1H), 6.96 (d, J=8.0 Hz, 1H), 4.30 (t, J=6.2 Hz, 2H), 1.89-1.87 (m, 3H), 1.04 (d, J=6.4 Hz, 6H); ES-LCMS m/z: 246.3 $[M+H]^+$.

Step 3: Synthesis of 2-(Ethoxymethyl)-9-isopentyloxy-1H-imidazo[4,5-c]quinoline 5-Isopentyloxyquinoline-3,4-diamine (110.00 mg, 448.39 μmol, 1.0 eq.), 2-ethoxyacetic acid (1.21 g, 11.62 mmol, 1.10 mL, 25.9 eq.) and 4 Å MS (150.00 mg) were placed into a microwave tube.

The sealed tube was heated at 130° C. for 1 h under microwave. The solid was filtered off. The filtrate was diluted with DCM (50 mL) and water (20 mL). The mixture was adjusted to pH=7 with aqueous NaOH (1 M). The layers were separated. The organic phase was washed with brine (20 mL), dried over anhydrous $Na_2SO_4$, filtered and concentrated in vacuo. The residue was purified with prep-TLC (DCM/MeOH=20/1). The desired product of 2-(ethoxymethyl)-9-isopentyloxy-1H-imidazo[4,5-c]quinoline (130.00 mg, 414.82 μmol, 92.51% yield) was obtained as a yellow solid. $^1$H NMR (400 MHz, $CD_3OD$) δ ppm: 9.10 (s, 1H), 7.73 (d, J=8.8 Hz, 1H), 7.66 (t, J=8.4 Hz, 1H), 7.20 (d, J=7.6 Hz, 1H), 4.80 (s, 2H), 4.48 (t, J=6.6 Hz, 2H), 3.73-3.68 (m, 2H), 1.95-1.88 (m, 3H), 1.29 (t, J=7.0 Hz, 3H), 1.05 (d, J=6.0 Hz, 6H); ES-LCMS m/z: 314.3 $[M+H]^+$.

Step 4: Synthesis of 2-(Ethoxymethyl)-9-isopentyloxy-5-oxido-1H-imidazo[4,5-c]quinolin-5-ium To a solution of 2-(ethoxymethyl)-9-isopentyloxy-1H-imidazo[4,5-c]quinoline (130.00 mg, 414.82 μmol, 1.0 eq.) in DCM (30.00 mL) was added m-CPBA (126.33 mg, 622.23 μmol, 85% purity, 1.5 eq.). The resulting mixture was stirred at 20° C. for 0.5 h. The reaction mixture was diluted with DCM (20 mL) and washed with saturated $K_2CO_3$ (10 mL) via extraction. The combined organic layers were washed with brine (15 mL), dried over $Na_2SO_4$, filtered and concentrated under reduced pressure. The desired product of 2-(ethoxymethyl)-9-isopentyloxy-5-oxido-1H-imidazo[4,5-c]quinolin-5-ium (130.00 mg, 394.67 μmol, 95.14% yield) was obtained as a brown solid. $^1$H NMR (400 MHz, $CD_3OD$) δ ppm: 9.11 (s, 1H), 8.31 (d, J=8.4 Hz, 1H), 7.82 (t, J=8.8 Hz, 1H), 7.41-7.38 (m, 1H), 4.88 (s, 2H), 4.54 (t, J=6.6 Hz, 2H), 3.73-3.67 (m, 2H), 1.94-1.86 (m, 3H), 1.29 (t, J=7.0 Hz, 3H), 1.04 (d, J=6.0 Hz, 6H); ES-LCMS m/z: 330.3 $[M+H]^+$.

Step 5: Synthesis of 2-(Ethoxymethyl)-9-isopentyloxy-1H-imidazo[4,5-c]quinolin-4-amine To a solution of 2-(ethoxymethyl)-9-isopentyloxy-5-oxido-1H-imidazo[4,5-c]-quinolin-5-ium (130.00 mg, 394.67 μmol, 1.0 eq.) and $NH_3 \cdot H_2O$ (494.04 mg, 3.95 mmol, 542.90 μL, 28% purity, 10.0 eq.) in $CHCl_3$ (6.00 mL) was added TsCl (112.87 mg, 592.00 μmol, 1.5 eq.). The resulting mixture was stirred at 25° C. for 0.5 h. The solvent was then removed in vacuo. The residue was purified with prep-HPLC (MeCN/$H_2O$ as eluents, acidic condition). After lyophilization, the desired product of 2-(ethoxymethyl)-9-isopentyloxy-1H-imidazo[4,5-c]quinolin-4-amine (75.00 mg, 196.61 μmol, 49.82% yield, 95.65% purity, as HCl salt) was obtained as a white solid. $^1$H NMR (400 MHz, $CD_3OD$) δ ppm: 7.68 (t, J=8.2 Hz, 1H), 7.33 (d, J=8.4 Hz, 1H), 7.17 (d, J=8.4 Hz, 1H), 4.86 (s, 2H), 4.51 (t, J=6.8 Hz, 2H), 3.75-3.70 (m, 2H), 1.94-1.86 (m, 3H), 1.31 (t, J=7.0 Hz, 3H), 1.05 (d, J=6.4 Hz, 6H); ES-LCMS m/z: 329.3 $[M+H]^+$.

The following compound was prepared using the same method as that described in Example 3 using corresponding reagents.

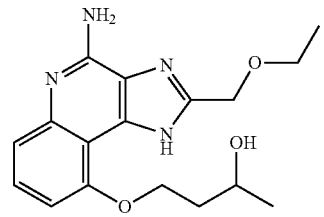 [SMILES: CCOCc1nc2c(N)nc3cccc(OCCC(C)O)c3c2[nH]1]

4-[[4-Amino-2-(ethoxymethyl)-1H-imidazo[4,5-c]quinolin-9-yl]oxy]butan-2-ol HCl salt was obtained in 20.06% yield with 100% purity as a white solid. H NMR (400 MHz, $CD_3OD$) δ ppm: 7.65 (t, J=8.4 Hz, 1H), 7.31 (d, J=8.0 Hz, 1H), 7.13 (d, J=8.4 Hz, 1H), 4.79 (s, 2H), 4.54-4.53 (m, 1H), 4.42-4.40 (m, 1H), 4.25-4.16 (m, 1H), 3.72-3.66 (m, 2H), 2.15-2.09 (m, 2H), 1.35 (d, J=6.4 Hz, 3H), 1.27 (t, J=7.0 Hz, 3H); ES-LCMS m/z: 330.9 $[M+H]^+$.

Example 4

Synthesis of 1-((4-amino-2-(ethoxymethyl)-1H-imidazo[4,5-c]quinolin-9-yl)oxy)propan-2-ol

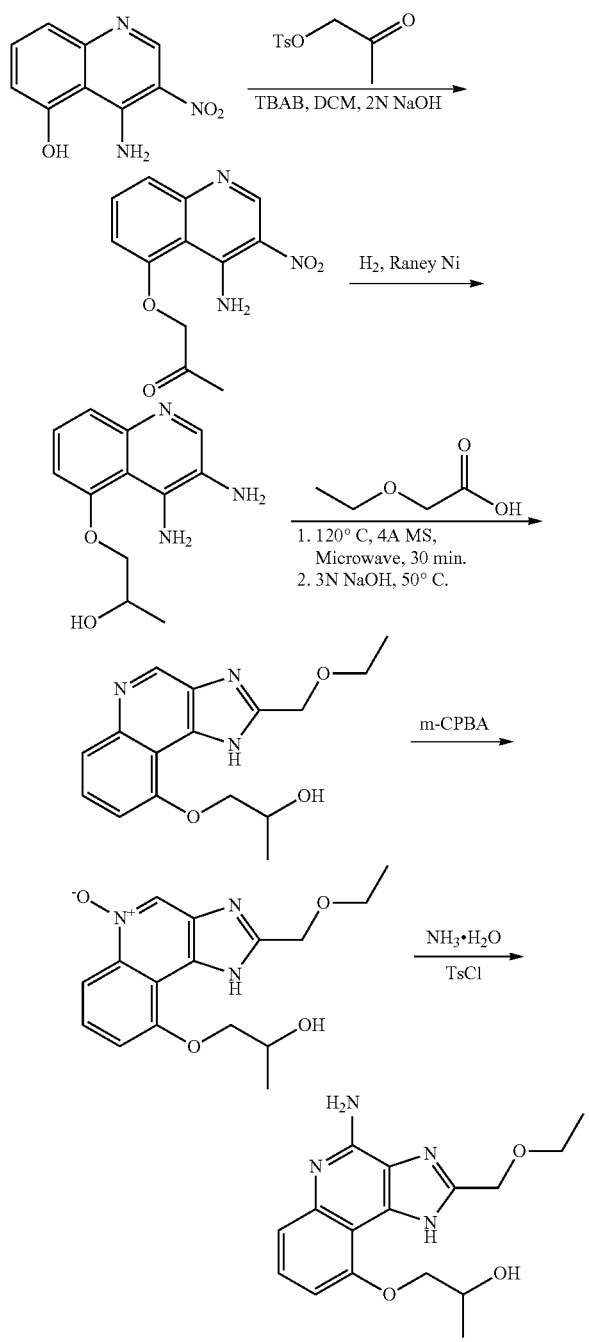

Step 1: Synthesis of 1-[(4-Amino-3-nitro-5-quinolyl)oxy]propan-2-one

To a solution of 4-amino-3-nitro-quinolin-5-ol (1.00 g, 4.87 mmol, 1.0 eq.), TBAB (1.57 g, 4.87 mmol, 1.0 eq.), KI (809.09 mg, 4.87 mmol, 1.0 eq.) in NaOH (2 M, 7.31 mL, 3.0 eq.) was added acetonyl 4-methylbenzenesulfonate (3.33 g, 14.61 mmol, 3.0 eq.) in DCM (8.00 mL) at 25° C. The mixture was stirred at 25° C. for 48 h. The reaction mixture was diluted with $H_2O$ (20 mL) and extracted with DCM (50 mL×2). The combined organic layers were washed with brine (20 mL), dried over $Na_2SO_4$, filtered and concentrated under reduced pressure to give a residue. The residue was purified with column chromatography (DCM to DCM/MeOH=20/1). The desired product of 1-[(4-amino-3-nitro-5-quinolyl)oxy]propan-2-one (220.00 mg, 842.17 μmol, 17.29% yield) was obtained as a yellow solid. $^1$H NMR (400 MHz, $CDCl_3$) δ ppm: 9.84 (br s, 1H), 9.41 (br s, 1H), 9.35 (s, 1H), 7.66-7.60 (m, 2H), 6.80-6.77 (m, 1H), 4.92 (s, 2H), 2.37 (s, 3H); ES-LCMS m/z: 262.2 [M+H]$^+$.

Step 2: Synthesis of 1-[(3,4-Diamino-5-quinolyl)oxy]propan-2-ol

To a solution of 1-[(4-amino-3-nitro-5-quinolyl)oxy]propan-2-one (220.00 mg, 842.17 μmol, 1.0 eq.) in MeOH (100.00 mL) was added Raney-Ni (100.29 mg, 1.17 mmol, 1.39 eq.) under $N_2$. The suspension was degassed under vacuum and purged with $H_2$ several times. The mixture was stirred under $H_2$ (15 psi) at 25° C. for 1 h. The solid was filtered off. The filtrate was concentrated in vacuo. The desired product of 1-[(3,4-diamino-5-quinolyl)oxy]-propan-2-ol (160.00 mg, 685.90 μmol, 81.44% yield) was obtained as a green solid. $^1$H NMR (400 MHz, $CD_3OD$) δ ppm: 7.95 (s, 1H), 7.64-7.60 (m, 1H), 7.28-7.26 (m, 1H), 7.02-6.90 (m, 1H), 4.32-4.29 (m, 2H), 4.07-4.04 (m, 1H), 1.33 (d, J=6.4 Hz, 3H); ES-LCMS m/z: 234.1 [M+H]$^+$.

Step 3: Synthesis of 1-[[2-(Ethoxymethyl)-1H-imidazo[4,5-c]quinolin-9-yl]oxy]propan-2-ol 1-[(3,4-Diamino-5-quinolyl)oxy]propan-2-ol (150.00 mg, 643.03 μmol, 1.0 eq.), 2-ethoxyacetic acid (1.10 g, 10.57 mmol, 1.00 mL, 16.4 eq.) and 4 Å MS (50.00 mg) were placed into a microwave tube. The sealed tube was heated at 120° C. for 0.5 h under microwave. An aqueous solution of 3 M NaOH (10 mL) and THF (3 mL) were added into the reaction mixture. The resulting mixture was stirred at 50° C. for 2 h. The mixture was extracted with ethyl acetate (50 mL×3). The combined organic layers were washed with saturated brine (10 mL), dried over anhydrous $Na_2SO_4$, filtered and concentrated under reduced pressure to give a residue. The residue was purified with prep-TLC (DCM/MeOH=15/1). The desired product of 1-[[2-(ethoxymethyl)-1H-imidazo[4,5-c]quinolin-9-yl]oxy]-propan-2-ol (23.00 mg, 76.33 μmol, 11.87% yield) was obtained as a yellow solid. $^1$H NMR (400 MHz, $CDCl_3$) δ ppm: 11.52 (s, 1H), 9.20 (s, 1H), 7.81 (d, J=8.4 Hz, 1H), 7.50 (t, J=8.0 Hz, 1H), 6.97 (d, J=7.6 Hz, 1H), 4.83 (s, 2H), 4.42 (m, 1H), 4.32-4.28 (m, 1H), 4.02 (t, J=8.2 Hz, 1H), 3.64-3.61 (m, 2H), 1.40 (m, 3H), 1.25 (m, 3H); ES-LCMS m/z: 302.2 [M+H]$^+$.

Step 4: Synthesis of 1-[[2-(Ethoxymethyl)-5-oxido-1H-imidazo[4,5-c]quinolin-5-ium-9-yl]oxy]propan-2-ol To a mixture of 1-[[2-(ethoxymethyl)-1H-imidazo[4,5-c]quinolin-9-yl]oxy]propan-2-ol (23.00 mg, 76.33 μmol, 1.0 eq.) in DCM (8.00 mL) was added m-CPBA (30.99 mg, 152.65 μmol, 85% purity, 2.0 eq.) in one portion at 25° C. The mixture was stirred at 25° C. for 1 h. The solvent was removed in vacuo. The crude product was used for the next step without further purification. The crude product of 1-[[2-(ethoxymethyl)-5-oxido-1H-imidazo[4,5-c]-quinolin-5-ium-9-yl]oxy]propan-2-ol (20.00 mg, 63.02 mol, 82.57% yield) was obtained as a brown solid. ¹H NMR (400 MHz, CDCl₃) δ ppm: 9.17 (s, 1H), 8.39 (d, J=8.8 Hz, 1H), 7.47-7.45 (m, 1H), 7.05-7.01 (m, 1H), 4.86 (s, 2H), 4.48 (m, 1H), 4.37 (m, 1H), 4.06 (d, J=8.4 Hz, 1H), 3.74-3.71 (m, 2H), 1.47 (br d, J=6.4 Hz, 3H), 1.35 (t, J=7.2 Hz, 3H); ES-LCMS m/z: =318.2 [M+H]⁺.

Step 5: Synthesis of 1-[[4-Amino-2-(ethoxymethyl)-1H-imidazo[4,5-c]quinolin-9-yl]oxy]-propan-2-ol To a mixture of 1-[[2-(ethoxymethyl)-5-oxido-1H-imidazo[4,5-c]quinolin-5-ium-9-yl]oxy]propan-2-ol (20.00 mg, 63.02 μmol, 1.0 eq.) and NH₃·H₂O (78.89 mg, 630.24 μmol, 86.69 μL, 28% purity, 10.0 eq.) in CHCl₃ (6.00 mL) was added TsCl (24.03 mg, 126.05 μmol, 2.0 eq.) at 25° C. The mixture was stirred at 25° C. for 3 h. The reaction mixture was concentrated under reduced pressure to remove the solvent. The residue was purified with preparative HPLC (MeCN/H₂O as eluents, acidic condition). After lyophilization, the desired product of 1-[[4-amino-2-(ethoxymethyl)-1H-imidazo[4,5-c]quinolin-9-yl]oxy]propan-2-ol (4.68 mg, 13.26 μmol, 21.04% yield, as HCl salt) was obtained as a white solid. ¹H NMR (400 MHz, CD₃OD) δ ppm: 7.66 (t, J=8.4 Hz, 1H), 7.35 (d, J=8.4 Hz, 1H), 7.20 (d, J=8.4 Hz, 1H), 4.83 (s, 2H), 4.42-4.39 (m, 1H), 4.36 (m, 1H), 4.18-4.16 (m, 1H), 3.71-3.68 (m, 2H), 1.36 (d, J=6.4 Hz, 3H), 1.29 (t, J=7.2 Hz, 3H); ES-LCMS m/z: 317.2 [M+H]⁺.

Example 5

Synthesis of 4-[[4-Amino-2-(2-methoxyethyl)-1H-imidazo[4,5-c]quinolin-9-yl]oxy]-2-methyl-butan-2-ol Scheme 5

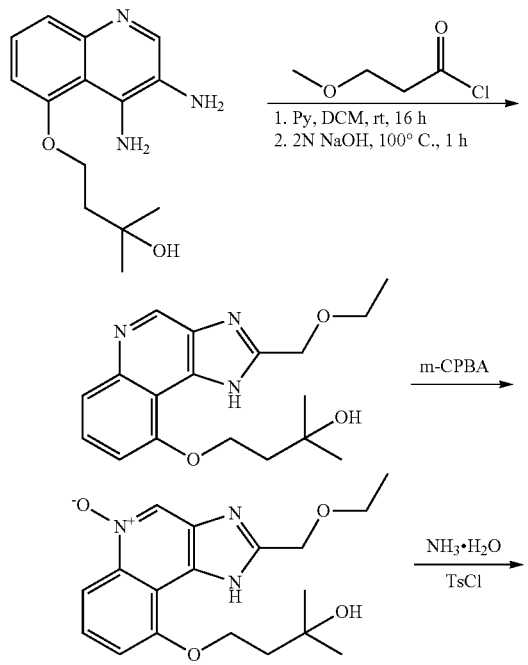

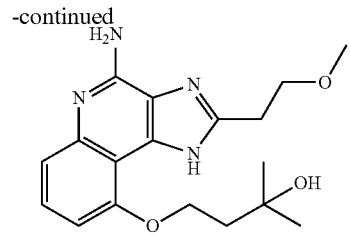

Step 1: Synthesis of 4-[[2-(2-Methoxyethyl)-1H-imidazo[4,5-c]quinolin-9-yl]oxy]-2-methyl-butan-2-ol To a solution of 4-[(3,4-diamino-5-quinolyl)oxy]-2-methyl-butan-2-ol (179.17 mg, 329.10 μmol, 1.0 eq.) and pyridine (260.32 mg, 3.29 mmol, 265.63 μL, 10.0 eq.) in DCM (2.00 mL) was added 3-methoxypropanoyl chloride (80.66 mg, 658.20 μmol, 2.0 eq.). The resulting mixture was stirred at 25° C. for 16 h. The solvent was removed in vacuo. The residue was dissolved in NaOH (2 M, 4.00 mL, 24.3 eq.) and stirred at 100° C. for 1 h. The mixture was diluted with water (10 mL) and extracted with DCM (50 mL×2). The combined organic phase was washed with brine (30 mL), dried over Na₂SO₄, filtered and concentrated in vacuo. The residue was purified with prep-TLC (DCM/MeOH=15/1). The desired product of 4-[[2-(2-methoxyethyl)-1H-imidazo[4,5-c]quinolin-9-yl]oxy]-2-methyl-butan-2-ol (90.00 mg, 273.23 μmol, 83.02% yield) was obtained as a brown solid. ¹H NMR (400 MHz, CD₃OD) δ ppm: 9.08 (s, 1H), 7.73 (d, J=8.4 Hz, 1H), 7.65 (t, J=8.0 Hz, 1H), 7.18 (d, J=7.2 Hz, 1H), 4.51 (t, J=6.0 Hz, 2H), 3.93 (t, J=6.4 Hz, 2H), 3.42 (s, 3H), 3.33-3.28 (m, 2H), 2.23 (t, J=6.0 Hz, 2H), 1.44 (s, 6H); ES-LCMS m/z: 330.3 [M+H]⁺.

Step 2: Synthesis of 4-[[2-(2-Methoxyethyl)-5-oxido-1H-imidazo[4,5-c]quinolin-5-ium-9-yl]oxy]-2-methyl-butan-2-ol To a solution of 4-[[2-(2-methoxyethyl)-1H-imidazo[4,5-c]quinolin-9-yl]oxy]-2-methyl-butan-2-ol (90.00 mg, 273.23 μmol, 1.0 eq.) in DCM (10.00 mL) was added m-CPBA (83.21 mg, 409.85 μmol, 85% purity, 1.5 eq.). The resulting mixture was stirred at 25° C. for 0.5 h. The solvent was removed in vacuo. The residue was purified with prep-TLC (DCM/MeOH=15/1). The desired product of 4-[[2-(2-methoxyethyl)-5-oxido-1H-imidazo[4,5-c]-quinolin-5-ium-9-yl]oxy]-2-methyl-butan-2-ol (60.00 mg, 173.72 mol, 63.58% yield) was obtained as a yellow solid. ¹H NMR (400 MHz, CDCl₃) δ ppm: 8.97 (s, 1H), 8.36 (d, J=8.8 Hz, 1H), 7.54 (t, J=8.4 Hz, 1H), 6.94 (d, J=8.0 Hz, 1H), 4.38 (t, J=5.6 Hz, 2H), 3.81 (t, J=6.2 Hz, 2H), 3.40 (s, 3H), 3.17 (t, J=6.0 Hz, 2H), 2.24 (t, J=5.6 Hz, 2H), 1.48 (s, 6H); ES-LCMS m/z: 345.9 [M+H]⁺.

Step 3: Synthesis of 4-[[4-Amino-2-(2-methoxyethyl)-1H-imidazo[4,5-c]quinolin-9-yl]oxy]-2-methyl-butan-2-ol To a solution of 4-[[2-(2-methoxyethyl)-5-oxido-1H-imidazo[4,5-c]quinolin-5-ium-9-yl]oxy]-2-methyl-butan-2-ol (60.00 mg, 173.72 μmol, 1.0 eq.) and NH₃·H₂O (217.81 mg, 1.74 mmol, 239.35 μL, 28% purity, 10.0 eq.) in CHCl₃ (6.00 mL) was added TsCl (66.24 mg, 347.44 mol, 2.0 eq.). The resulting mixture was stirred at 25° C. for 0.5 h. The solvent was removed in vacuo. The residue was purified with prep-HPLC (MeCN/H₂O as eluents, acidic condition). After lyophilization, the desired product of 4-[[4-amino-2-(2-methoxyethyl)-1H-imidazo[4,5-c]quinolin-9-yl]oxy]-2-methyl-butan-2-ol (24.95 mg, 63.20 μmol, 36.38% yield, 96.48% purity, as HCl salt) was obtained as a white solid. ¹H NMR (400 MHz, CD₃OD) δ ppm: 7.66 (t, J=8.2 Hz, 1H), 7.32 (d, J=8.0 Hz, 1H), 7.13 (d, J=8.0 Hz, 1H), 4.49 (t, J=6.0 Hz, 2H), 3.93 (t, J=6.6 Hz, 2H), 3.42 (s, 3H), 3.26 (t, J=6.2 Hz, 2H), 2.19 (t, J=5.8 Hz, 2H), 1.43 (s, 6H); ES-LCMS m/z: 345.3 [M+H]⁺.

Example 6

Synthesis of 4-[4-Amino-2-(ethoxymethyl)-1-methyl-imidazo[4,5-c]quinolin-9-yl]oxy-2-methyl-butan-2-ol Scheme 6

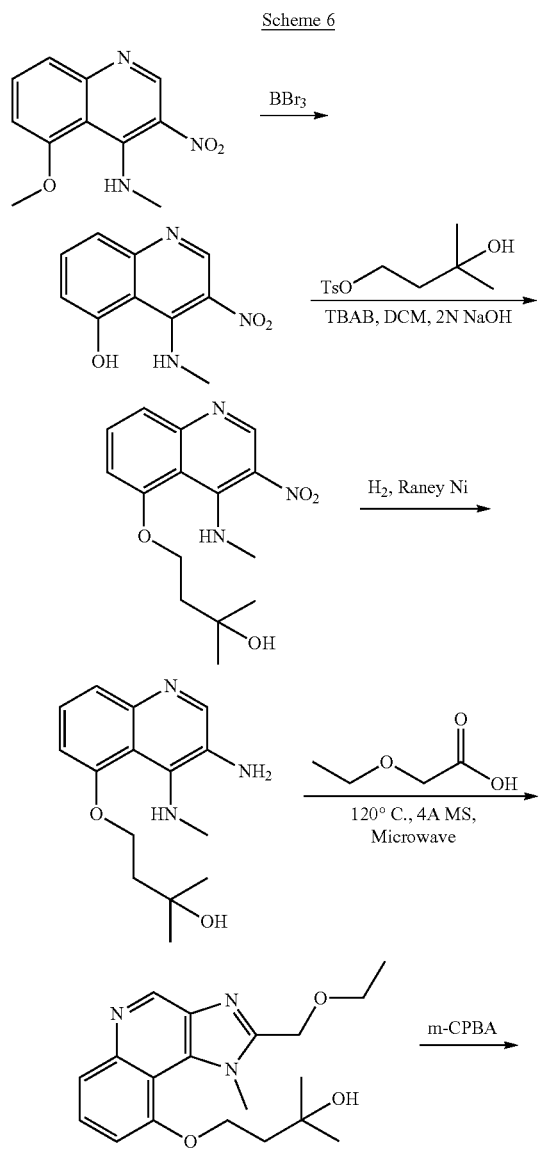

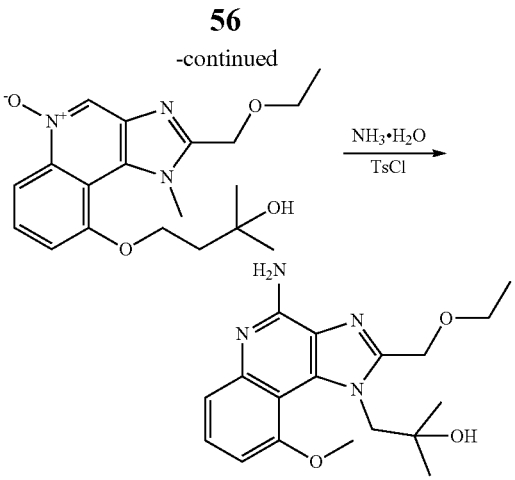

Step 1: Synthesis of 4-(methylamino)-3-nitro-quinolin-5-ol

To a solution of 5-methoxy-N-methyl-3-nitro-quinolin-4-amine (300.00 mg, 1.29 mmol, 1.0 eq.) in DCM (15.00 mL) was added BBr₃ (1.62 g, 6.45 mmol, 621.48 μL, 5.0 eq.) dropwise at −78° C. The resulting mixture was stirred at 60° C. for 2 h. The mixture was added to MeOH (100 mL) dropwise at −30° C. The solvent was removed in vacuo. The desired product of 4-(methylamino)-3-nitro-quinolin-5-ol (300.00 mg, crude) was obtained as a brown solid. ¹H NMR (400 MHz, CD₃OD) b ppm: 9.22 (s, 1H), 7.79 (m, 1H), 7.33 (m, 1H), 7.15-7.13 (m, 1H), 3.08 (s, 3H); ES-LCMS m/z: 220.2 [M+H]⁺.

Step 2: Synthesis of 2-methyl-4-[[4-(methylamino)-3-nitro-5-quinolyl]oxy]butan-2-ol To a solution of 4-(methylamino)-3-nitro-quinolin-5-ol (250.00 mg, 1.14 mmol, 1.0 eq.), TBAB (367.67 mg, 1.14 mmol, 1.0 eq.) and KI (189.32 mg, 1.14 mmol, 1.0 eq.) in NaOH (2 M, 1.71 mL, 3.0 eq.) was added a solution of (3-hydroxy-3-methyl-butyl)4-methylbenzenesulfonate (883.49 mg, 3.42 mmol, 3.0 eq.) in DCM (3.00 mL). The resulting mixture was stirred at 25° C. for 64 h. The reaction mixture was diluted with H₂O (10 mL) and extracted with DCM (30 mL×2). The combined organic layers were washed with brine (10 mL), dried over Na₂SO₄, filtered and concentrated under reduced pressure to give a residue. The residue was purified with column chromatography (DCM to DCM/MeOH=20/1). The desired product of 2-methyl-4-[[4-(methylamino)-3-nitro-5-quinolyl]oxy]butan-2-ol (100.00 mg, 327.51 μmol, 28.73% yield) was obtained as a yellow solid. ¹H NMR (400 MHz, CDCl₃) δ ppm: 9.36 (s, 1H), 9.02 (s, 1H), 7.61-7.55 (m, 2H), 6.91 (d, J=6.8 Hz, 1H), 4.36 (t, J=5.8 Hz, 2H), 2.84 (d, J=5.2 Hz, 3H), 2.13 (t, J=5.8 Hz, 2H), 1.41 (s, 6H); ES-LCMS m/z: 306.0 [M+H]⁺.

Step 3: Synthesis of 4-[[3-Amino-4-(methylamino)-5-quinolyl]oxy]-2-methyl-butan-2-ol To a solution of 2-methyl-4-[[4-(methylamino)-3-nitro-5-quinolyl]oxy]butan-2-ol (100.00 mg, 327.51 μmol, 1.0 eq.) in MeOH (50.00 mL) was added Raney-Ni (100.00 mg, 1.17 mmol, 3.6 eq.) under N₂. The suspension was degassed under vacuum and purged with H₂ several times. The mixture was stirred under H₂ (15 psi) at 25° C. for 1 h. The mixture was filtered. The filtrate was concentrated in vacuo.

The desired product of 4-[[3-amino-4-(methylamino)-5-quinolyl]oxy]-2-methyl-butan-2-ol (80.00 mg, 290.54 μmol, 88.71% yield) was obtained as a green solid. $^1$H NMR (400 MHz, CD$_3$OD) δ ppm: 8.07 (s, 1H), 7.44 (t, J=8.0 Hz, 1H), 7.29 (d, J=8.4 Hz, 1H), 6.95 (d, J=7.6 Hz, 1H), 4.35 (t, J=6.4 Hz, 2H), 3.19 (d, J=10.4 Hz, 3H), 2.10 (d, J=6.4 Hz, 2H), 1.33 (s, 6H); ES-LCMS m/z: 276.3 [M+H]$^+$.

Step 4: Synthesis of 4-[2-(ethoxymethyl)-1-methyl-imidazo[4,5-c]quinolin-9-yl]oxy-2-methyl-butan-2-ol 4-[[3-Amino-4-(methylamino)-5-quinolyl]oxy]-2-methyl-butan-2-ol (70.00 mg, 254.22 μmol, 1.0 eq.), 2-ethoxyacetic acid (1.65 g, 15.85 mmol, 1.50 mL, 62.4 eq.) and 4 Å MS (100.00 mg) were placed into a microwave tube. The sealed tube was heated at 120° C. for 30 minutes under microwave. The mixture was filtered. The filtrate was diluted with DCM (50 mL) and water (10 mL) and was adjusted to pH=7 by aqueous NaOH (2 M). The organic layer was separated and washed with brine (10 mL), dried with anhydrous Na$_2$SO$_4$, filtered and concentrated in vacuo. The crude product was purified with prep-TLC (DCM/MeOH=15/1). The desired product of 4-[2-(ethoxymethyl)-1-methyl-imidazo [4,5-c]quinolin-9-yl]oxy-2-methyl-butan-2-ol (20.00 mg, 58.24 μmol, 22.91% yield) was obtained as a yellow solid. $^1$H NMR (400 MHz, CDCl$_3$) δ ppm: 9.25 (s, 1H), 7.88 (d, J=7.6 Hz, 1H), 7.59 (t, J=8.2 Hz, 1H), 7.10 (d, J=7.2 Hz, 1H), 4.89 (s, 2H), 4.48 (t, J=7.6 Hz, 2H), 4.32 (s, 3H), 3.66-3.61 (m, 2H), 2.20 (t, J=7.6 Hz, 2H), 1.38 (s, 6H), 1.26 (m, 3H); ES-LCMS m/z: 344.3 [M+H]$^+$.

Step 5: Synthesis of 4-[2-(Ethoxymethyl)-1-methyl-5-oxido-imidazo[4,5-c]quinolin-5-ium-9-yl]oxy-2-methyl-butan-2-ol To a solution of 4-[2-(ethoxymethyl)-1-methyl-imidazo[4,5-c]quinolin-9-yl]-oxy-2-methyl-butan-2-ol (20.00 mg, 58.24 μmol, 1.0 eq.) in DCM (5.00 mL) was added m-CPBA (23.65 mg, 116.48 mol, 85% purity, 2.0 eq.). The resulting mixture was stirred at 25° C. for 0.5 h. The solvent was removed in vacuo. The residue was purified with prep-TLC (DCM/MeOH=10/1). The desired product of 4-[2-(ethoxymethyl)-1-methyl-5-oxido-imidazo[4,5-c]quinolin-5-ium-9-yl]oxy-2-methyl-butan-2-ol (20.00 mg, crude) was obtained as a white solid. $^1$H NMR (400 MHz, CDCl$_3$) δ ppm: 9.28 (s, 1H), 8.70 (d, J=8.8 Hz, 1H), 7.71 (t, J=8.2 Hz, 1H), 7.22 (d, J=8.0 Hz, 1H), 4.86 (s, 2H), 4.52-4.48 (m, 2H), 4.28 (s, 3H), 3.67-3.61 (m, 2H), 2.23-2.16 (m, 2H), 1.35 (s, 6H), 1.29-1.27 (m, 3H); ES-LCMS m/z: 360.3 [M+H]$^+$.

Step 6: Synthesis of 4-[4-Amino-2-(ethoxymethyl)-1-methyl-imidazo[4,5-c]quinolin-9-yl]oxy-2-methyl-butan-2-ol To a solution of 4-[2-(ethoxymethyl)-1-methyl-5-oxido-imidazo[4,5-c]quinolin-5-ium-9-yl]oxy-2-methyl-butan-2-ol (20.00 mg, 55.65 μmol, 1.0 eq.) and NH$_3$·H$_2$O (69.66 mg, 556.45 μmol, 76.54 μL, 28% purity, 10.0 eq.) in CHCl$_3$ (2.00 mL) was added TsCl (15.91 mg, 83.47 mol, 1.5 eq.). The resulting mixture was stirred at 25° C. for 0.5 h. The solvent was removed in vacuo. The residue was purified with prep-HPLC (MeCN/H$_2$O as eluents, acidic condition). After lyophilization, the desired product of 4-[4-amino-2-(ethoxymethyl)-1-methyl-imidazo[4,5-c]quinolin-9-yl]oxy-2-methyl-butan-2-ol (6.00 mg, 15.19 mol, 27.30% yield, as a HCl salt) was obtained as a white solid: $^1$H NMR (400 MHz, CD$_3$OD) δ ppm: 7.65 (t, J=8.2 Hz, 1H), 7.31 (d, J=8.4 Hz, 1H), 7.18 (d, J=8.0 Hz, 1H), 4.85 (s, 2H), 4.48 (t, J=7.8 Hz, 2H), 4.26 (s, 3H), 3.68-3.63 (m, 2H), 2.16 (t, J=7.8 Hz, 2H), 1.31 (s, 6H), 1.26 (t, J=6.8 Hz, 3H); ES-LCMS m/z: 359.3 [M+H]$^+$.

The following compound was prepared in a similar way as that described in Examples 5 and 6 using corresponding reagents.

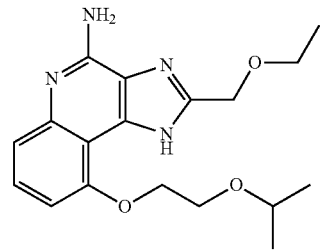 [SMILES: CCOCc1nc2c(N)nc3cccc(OCCOC(C)C)c3c2[nH]1]

2-(Ethoxymethyl)-9-(2-isopropoxyethoxy)-1H-imidazo[4,5-c]quinolin-4-amine was obtained in 40.79% yield with 100% purity as a HCl salt as a white solid. $^1$H NMR (400 MHz, CD$_3$OD) δ ppm: 7.63 (t, J=8.2 Hz, 1H), 7.30 (d, J=8.4 Hz, 1H), 7.18 (d, J=8.0 Hz, 1H), 4.79 (s, 2H), 4.54-4.51 (m, 2H), 3.94-3.91 (m, 2H), 3.75-3.69 (m, 1H), 3.66-3.64 (m, 2H), 1.24 (t, J=7.0 Hz, 3H), 1.15 (d, J=6.0 Hz, 6H); ES-LCMS m/z: 345.3 [M+H]+.

Example 7

Synthesis of 4-[4-Amino-2-(ethoxymethyl)-1-isobutyl-imidazo[4,5-c]quinolin-9-yl]oxy-2-methyl-butan-2-ol

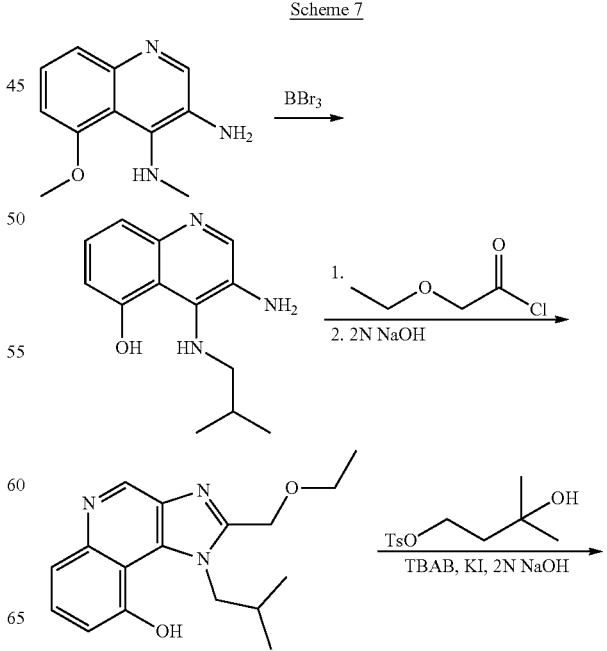

Scheme 7

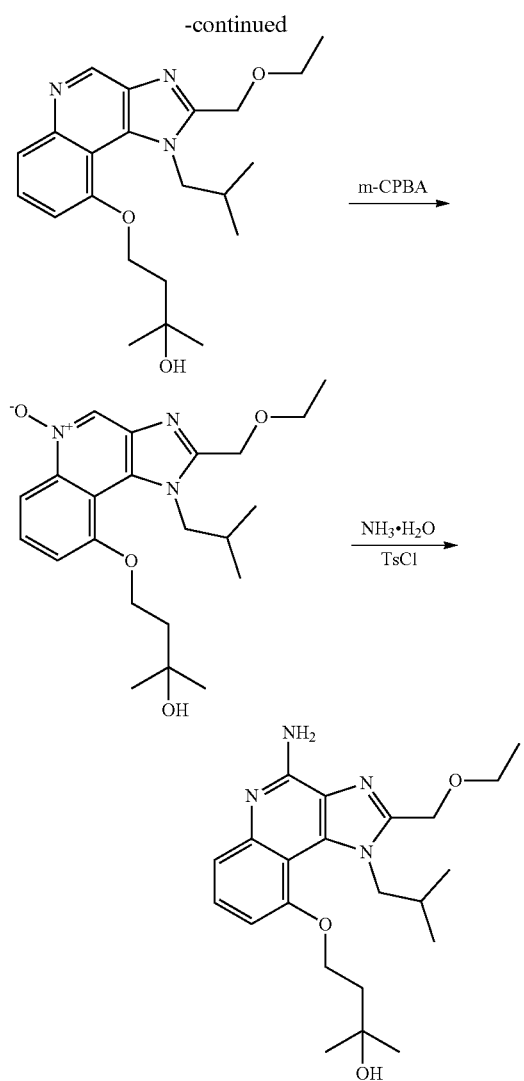

Step 1: Synthesis of 3-Amino-4-(isobutylamino)quinolin-5-ol

To a solution of $N^4$-isobutyl-5-methoxy-quinoline-3,4-diamine (450.00 mg, 1.83 mmol, 1.0 eq.) in DCM (30.00 mL) was added $BBr_3$ (2.30 g, 9.17 mmol, 883.73 μL, 5.0 eq.) dropwise at −78° C. The resulting mixture was stirred at 60° C. for 2 h. The mixture was added to MeOH (100 mL) dropwise at −30° C. The solvent was removed in vacuo. The desired product of 3-amino-4-(isobutylamino) quinolin-5-ol (500.00 mg, 1.64 mmol, 89.81% yield, as 2HCl salt) was obtained as a brown solid. $^1H$ NMR (400 MHz, $CD_3OD$) δ ppm: 8.19 (s, 1H), 7.65 (t, J=8.2 Hz, 1H), 7.24 (d, J=8.4 Hz, 1H), 6.97 (d, J=7.2 Hz, 1H), 3.80 (d, J=6.4 Hz, 2H), 2.07-2.02 (m, 1H), 1.10 (d, J=6.4 Hz, 6H); ES-LCMS m/z: 232.3 $[M+H]^+$.

Step 2: Synthesis of 2-(Ethoxymethyl)-1-isobutyl-imidazo[4,5-c]quinolin-9-ol To a solution of 3-amino-4-(isobutylamino)quinolin-5-ol (450.00 mg, 1.48 mmol, 1.0 eq., as 2HCl salt) in Pyridine (4.90 g, 61.95 mmol, 5.0 mL, 41.9 eq.) was added 2-ethoxyacetyl chloride (271.92 mg, 2.22 mmol, 1.5 eq.). The resulting mixture was stirred at 25° C. for 1 h. The solvent was removed in vacuo. The residue was dissolved in NaOH (2 M, 7.40 mmol, 3.0 mL, 5.0 eq.) and stirred at 100° C. for 2 h. The mixture was partitioned between DCM (40 mL) and water (10 mL). The organic layer was separated, washed with brine (10 mL), dried over $Na_2SO_4$, filtered and concentrated in vacuo. The residue was purified with column chromatography (DCM to DCM/MeOH=10/1). The desired product of 2-(ethoxymethyl)-1-isobutyl-imidazo[4,5-c]quinolin-9-ol (100.00 mg, 334.03 μmol, 22.58% yield) was obtained as a red solid. $^1H$ NMR (400 MHz, $CD_3OD$) δ ppm: 9.06 (s, 1H), 7.69-7.67 (m, 1H), 7.56 (t, J=8.0 Hz, 1H), 7.11-7.08 (m, 1H), 4.89 (s, 2H), 4.65-4.63 (m. 2H), 3.68-3.62 (m, 2H), 2.24-2.16 (m, 1H), 1.26 (t, J=7.0 Hz, 3H), 0.79-0.76 (m, 6H); ES-LCMS m/z: 300.3 $[M+H]^+$.

Step 3: Synthesis of 4-[2-(Ethoxymethyl)-1-isobutyl-imidazo[4,5-c]quinolin-9-yl]oxy-2-methyl-butan-2-ol To a solution of 2-(ethoxymethyl)-1-isobutyl-imidazo[4,5-c]quinolin-9-ol (60.00 mg, 200.42 mol, 1.0 eq.), TBAB (64.61 mg, 200.42 μmol, 1.0 eq.) and KI (33.27 mg, 200.42 μmol, 1.0 eq.) in NaOH (2 M, 300.63 μL, 3.0 eq.) was added a solution of (3-hydroxy-3-methyl-butyl)4-methylbenzenesulfonate (155.32 mg, 601.26 μmol, 3.0 eq.) in DCM (3.00 mL). The resulting mixture was stirred at 25° C. for 64 h. The reaction mixture was diluted with $H_2O$ (20 mL) and extracted with DCM (50 mL×2). The combined organic layers were washed with brine (20 mL), dried over $Na_2SO_4$, filtered and concentrated under reduced pressure to give a residue. The residue was purified with column chromatography (DCM to DCM/MeOH=10/1). The desired product of 4-[2-(ethoxymethyl)-1-isobutyl-imidazo[4,5-c] quinolin-9-yl]oxy-2-methyl-butan-2-ol (60.00 mg, 155.64 μmol, 77.66% yield) was obtained as a red solid. $^1H$ NMR (400 MHz, $CDCl_3$) δ ppm: 9.26 (s, 1H), 7.88 (d, J=8.4 Hz, 1H), 7.59 (t, J=8.2 Hz, 1H), 7.09 (d, J=7.2 Hz, 1H), 4.88 (s, 2H), 4.68 (br, s. 2H), 4.48 (t, J=7.4 Hz, 2H), 3.65-3.59 (m, 2H), 2.19 (t, J=7.6 Hz, 2H), 2.06-2.02 (m, 1H), 1.34 (s, 6H), 1.28-1.24 (m, 3H), 0.66 (d, J=6.0 Hz, 6H); ES-LCMS m/z: 386.4 $[M+H]^+$.

Step 4: Synthesis of 4-[2-(Ethoxymethyl)-1-isobutyl-5-oxido-imidazo[4,5-c]quinolin-5-ium-9-yl]oxy-2-methyl-butan-2-ol To a solution of 4-[2-(ethoxymethyl)-1-isobutyl-imidazo [4,5-c]quinolin-9-yl]oxy-2-methyl-butan-2-ol (60.00 mg, 155.64 μmol, 1.0 eq.) in DCM (10.00 mL) was added m-CPBA (47.40 mg, 233.46 mol, 85% purity, 1.5 eq.). The resulting mixture was stirred at 25° C. for 0.5 h. The solvent was removed in vacuo. The residue was purified with prep-TLC (DCM/MeOH=10/1). The desired product of 4-[2-(ethoxymethyl)-1-isobutyl-5-oxido-imidazo[4,5-c] quinolin-5-ium-9-yl]oxy-2-methyl-butan-2-ol (50.00 mg, 124.53 μmol, 80.01% yield) was obtained as a yellow solid. $^1H$ NMR (400 MHz, $CDCl_3$) δ ppm: 9.07 (s, 1H), 8.68 (d, J=8.0 Hz, 1H), 7.68 (t, J=8.4 Hz, 1H), 7.22 (d, J=8.0 Hz, 1H), 4.84 (s, 2H), 4.61 (br, s. 2H), 4.51 (t, J=7.8 Hz, 2H), 3.65-3.59 (m, 2H), 2.19 (t, J=7.6 Hz, 2H), 1.99-1.94 (m, 1H), 1.35 (s, 6H), 1.29-1.27 (m, 3H), 0.67 (d, J=6.0 Hz, 6H); ES-LCMS m/z: 402.4 $[M+H]^+$.

Step 5: Synthesis of 4-[4-Amino-2-(ethoxymethyl)-1-isobutyl-imidazo[4,5-c]quinolin-9-yl]oxy-2-methyl-butan-2-ol To a solution of 4-[2-(ethoxymethyl)-1-isobutyl-5-oxido-imidazo[4,5-c]quinolin-5-ium-9-yl]oxy-2-methyl-butan-2- ol (50.00 mg, 124.53 μmol, 1.0 eq.) and NH$_3$·H$_2$O (155.89 mg, 1.25 mmol, 171.31 μL, 28% purity, 10.0 eq.) in CHCl$_3$ (5.00 mL) was added TsCl (28.49 mg, 149.44 μmol, 1.2 eq.). The resulting mixture was stirred at 25° C. for 0.5 h. The solvent was removed in vacuo. The residue was purified with prep-HPLC (MeCN/H$_2$O as eluents, acidic condition). After lyophilization, the desired product of 4-[4-amino-2-(ethoxymethyl)-1-isobutyl-imidazo[4,5-c]quinolin-9-yl]oxy-2-methyl-butan-2-ol (26.50 mg, 60.38 μmol, 48.48% yield, 99.56% purity, as a HCl salt) was obtained as a white solid. $^1$H NMR (400 MHz, CD$_3$OD) δ ppm: 7.69 (t, J=8.2 Hz, 1H), 7.34 (t, J=8.0 Hz, 1H), 7.22 (d, J=8.4 Hz, 1H), 4.87 (s, 2H), 4.71 (br, s. 2H), 4.53 (t, J=7.6 Hz, 1H), 3.69-3.63 (m, 2H), 2.18 (t, J=7.6 Hz, 2H), 2.02-1.97 (m, 1H), 1.29 (s, 6H), 1.26 (t, J=7.0 Hz, 3H), 0.74 (d, J=4.2 Hz, 6H); ES-LCMS m/z: 401.4 [M+H]$^+$.

Example 8

Preparation of Intermediates

Intermediate 1:
4-Chloro-5-methoxy-3-nitro-quinoline

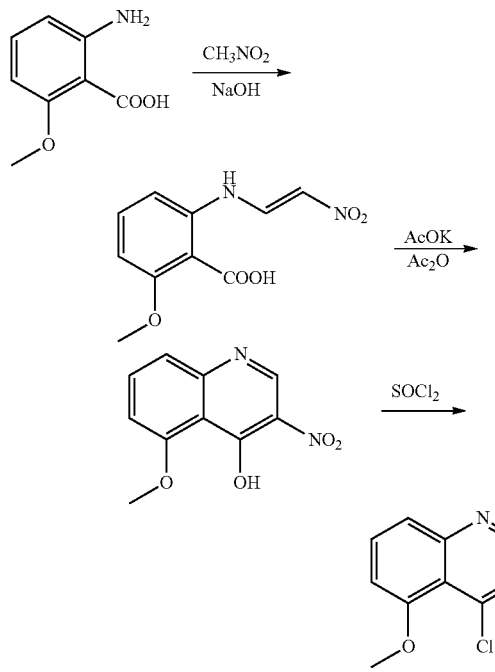

Step 1: Synthesis of 2-methoxy-6-[[(E)-2-nitrovinyl]amino]benzoic acid

To a solution of NaOH (40.20 g, 1.01 mol, 3.4 eq.) in water (100 mL) was added CH$_3$NO$_2$ (23.73 g, 388.84 mmol, 21.00 mL, 1.3 eq.) at 0° C. The mixture was warmed to 40° C. and additional amount of CH$_3$NO$_2$ (23.73 g, 388.84 mmol, 21.00 mL, 1.3 eq.) was added slowly at 40° C. This temperature was maintained until all solids dissolved and a clear red solution was obtained. The solution was cooled to 30° C., poured into 300 g of chipped ice, and acidified with concentrated HCl (100 mL). The mixture was immediately added to a solution of 2-amino-6-methoxy-benzoic acid (50.00 g, 299.11 mmol, 1.0 eq.) and conc. HCl (35 mL) in water (1400 mL). The solution was allowed to stir at 20° C. for 16 h. The mixture was filtered. The cake was washed with water (300 mL×3), and dried in vacuo. The desired product of 2-methoxy-6-[[(E)-2-nitrovinyl] amino]benzoic acid (67.00 g, 281.28 mmol, 94.04% yield) was obtained as a yellow solid. $^1$H NMR (400 MHz, CD$_3$OD) δ ppm: 7.70 (d, J=6.0 Hz, 1H), 7.51 (t, J=8.4 Hz, 1H), 7.11 (d, J=8.4 Hz, 1H), 6.93 (d, J=8.4 Hz, 1H), 6.68 (d, J=6.0 Hz, 1H), 3.89 (d, J=4.4 Hz, 3H); ES-LCMS m/z: 261.1 [M+Na]$^+$.

Step 2: Synthesis of
5-methoxy-3-nitro-quinolin-4-ol

A solution of 2-methoxy-6-[[(E)-2-nitrovinyl]amino]benzoic acid (56.00 g, 235.10 mmol, 1.0 eq.) in Ac$_2$O (300.00 mL) was heated at 105° C. for 0.5 h, and a clear solution was obtained. AcOK (27.69 g, 282.12 mmol, 1.2 eq.) was added. The resulting mixture was stirred at 105° C. for 2 h. The mixture was filtered. The cake was washed with acetic acid (30 mL×2) and water (100 mL×3). The cake was dried on oil pump. The desired product of 5-methoxy-3-nitro-quinolin-4-ol (19.00 g, 86.29 mmol, 36.70% yield) was obtained as an off-white solid. $^1$H NMR (400 MHz, DMSO-d$_6$) δ ppm: 12.59 (s, 1H), 8.96 (s, 1H), 7.62 (t, J=8.2 Hz, 1H), 7.16 (d, J=8.0 Hz, 1H), 6.95 (d, J=8.0 Hz, 1H), 3.83 (s, 3H); ES-LCMS m/z: 221.2 [M+H]$^+$.

Step 3: Synthesis of
4-chloro-5-methoxy-3-nitro-quinoline

To a suspension of 5-methoxy-3-nitro-quinolin-4-ol (2.00 g, 9.08 mmol, 1.0 eq.) in SOCl$_2$ (8.20 g, 68.92 mmol, 5.00 mL, 7.6 eq.) was added DMF (66.39 mg, 908.35 mol, 69.89 μL, 0.1 eq.). The resulting mixture was stirred at 80° C. for 4 h. The solvent was removed in vacuo. The desired product of 4-chloro-5-methoxy-3-nitro-quinoline (2.10 g, 8.80 mmol, 96.92% yield) was obtained as a brown solid. $^1$H NMR (400 MHz, CDCl$_3$) δ ppm: 9.12 (s, 1H), 8.08 (t, J=8.8 Hz, 1H), 7.96-7.92 (m, 1H), 7.20 (d, J=8.4 Hz, 1H), 4.08 (s, 3H); ES-LCMS m/z: 239.2 [M+H]$^+$.

Intermediate 2: 4-Amino-3-nitro-quinolin-5-ol

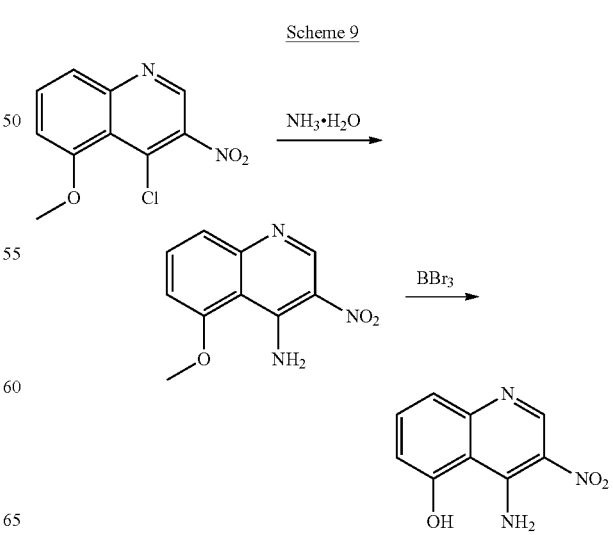

Step 1: Synthesis of 5-methoxy-3-nitro-quinolin-4-amine

A solution of 4-chloro-5-methoxy-3-nitro-quinoline (5.28 g, 22.13 mmol, 1.0 eq.) in THF (50 mL) was added to NH$_3$·H$_2$O (91.00 g, 726.96 mmol, 100.00 mL, 28% purity, 32.9 eq.) in THF (100 mL) dropwise at 0° C. The mixture was stirred at 25° C. for 2 h. The reaction mixture was filtered. The residue was washed with H$_2$O (50 mL×3) and dried in vacuo. The desired product of 5-methoxy-3-nitro-quinolin-4-amine (4.83 g, 22.03 mmol, 99.55% yield) was obtained as a yellow solid. $^1$H NMR (400 MHz, CD$_3$OD) δ ppm: 9.17 (s, 1H), 7.75 (t, J=8.4 Hz, 1H), 7.46 (d, J=8.4 Hz, 1H), 7.15 (d, J=8.0 Hz, 1H), 4.13 (s, 3H); ES-LCMS m/z: 220.2 [M+H]$^+$.

Step 2: Synthesis of 4-amino-3-nitro-quinolin-5-ol

To a solution of 5-methoxy-3-nitro-quinolin-4-amine (2.00 g, 9.12 mmol, 1.0 eq.) in DCM (100.00 mL) was added BBr$_3$ (22.86 g, 91.20 mmol, 8.79 mL, 10.0 eq.) dropwise at −78° C. The reaction mixture was stirred at 60° C. for 16 h. The reaction mixture was added to MeOH (200 mL) at −30° C., and then concentrated under reduced pressure to give a residue. The residue was suspended in DCM and filtered. The cake was dried in vacuo. The desired product of 4-amino-3-nitro-quinolin-5-ol (2.53 g, crude) was obtained as a green solid. $^1$H NMR (400 MHz, CD$_3$OD) δ ppm: 9.41 (s, 1H), 7.83 (t, J=8.4 Hz, 1H), 7.33 (d, J=8.4 Hz, 1H), 7.13 (d, J=8.4 Hz, 1H); ES-LCMS m/z: 206.2 [M+H]$^+$.

Intermediate 3: N$^4$—Isobutyl-5-methoxy-quinoline-3,4-diamine

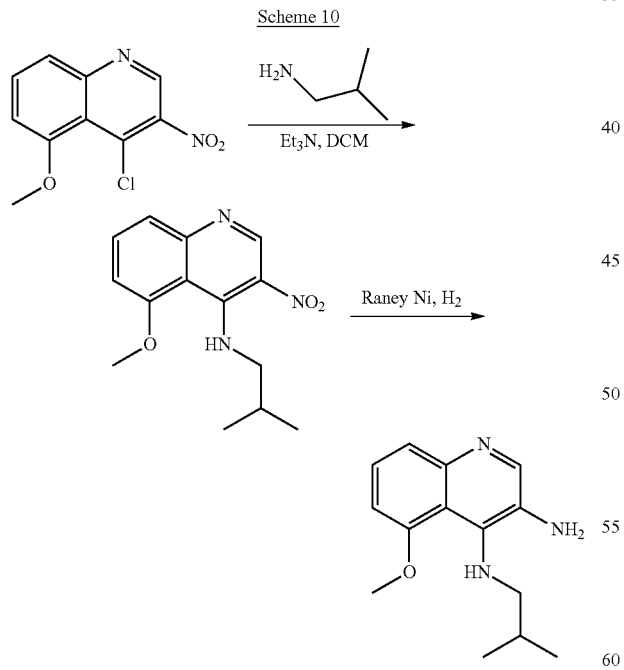

Scheme 10

Step 1: Synthesis of N-isobutyl-5-methoxy-3-nitro-quinolin-4-amine

To a solution of 2-methylpropan-1-amine (612.91 mg, 8.38 mmol, 828.26 μL, 2.0 eq.) and Et$_3$N (2.12 g, 20.95 mmol, 2.90 mL, 5.0 eq.) in DCM (50.00 mL) was added 4-chloro-5-methoxy-3-nitro-quinoline (1.00 g, 4.19 mmol, 1.0 eq.). The resulting mixture was stirred at 25° C. for 0.5 h. The reaction mixture was washed with water (30 mL) and brine (30 mL) via extraction. The organic phase was dried over anhydrous Na$_2$SO$_4$, filtered and concentrated in vacuo. The residue was purified with column chromatography (PE to PE/EtOAc=1/1). The desired product of N-isobutyl-5-methoxy-3-nitro-quinolin-4-amine (1.00 g, 3.63 mmol, 86.69% yield) was obtained as a yellow solid. $^1$H NMR (400 MHz, CD$_3$OD) δ ppm: 8.85 (s, 1H), 7.70 (t, J=8.2 Hz, 1H), 7.47 (d, J=7.6 Hz, 1H), 7.16 (d, J=8.0 Hz, 1H), 4.14 (s, 3H), 2.85 (d, J=6.4 Hz, 2H), 2.04-1.94 (m, 1H), 1.00 (d, J=6.8 Hz, 6H); ES-LCMS m/z: 276.2 [M+H]$^+$.

Step 2: Synthesis of N$^4$-isobutyl-5-methoxy-quinoline-3,4-diamine

To a solution of N-isobutyl-5-methoxy-3-nitro-quinolin-4-amine (300.00 mg, 1.09 mmol, 1.0 eq.) in MeOH (50.00 mL) was added Raney-Ni (100.00 mg, 1.17 mmol, 1.1 eq.) under N$_2$. The suspension was degassed under vacuum and purged with H$_2$ several times. The mixture was stirred under H$_2$ (15 psi) at 25° C. for 1 h. The reaction mixture was filtered. The filtrate was concentrated in vacuo. The desired product of N$^4$-isobutyl-5-methoxy-quinoline-3,4-diamine (250.00 mg, 1.02 mmol, 93.49% yield) was obtained as a yellow solid. $^1$H NMR (400 MHz, CD$_3$OD) δ ppm: 8.28 (s, 1H), 7.42-7.40 (m, 1H), 7.33 (t, J=8.2 Hz, 1H), 6.91 (d, J=7.6 Hz, 1H), 4.03 (s, 3H), 3.08 (d, J=6.8 Hz, 2H), 1.90-1.80 (m, 1H), 1.02 (d, J=6.8 Hz, 6H); ES-LCMS m/z: 246.3 [M+H]$^+$.

Intermediate 4: 4-[(3,4-Diamino-5-quinolyl)oxy]-2-methyl-butan-2-ol

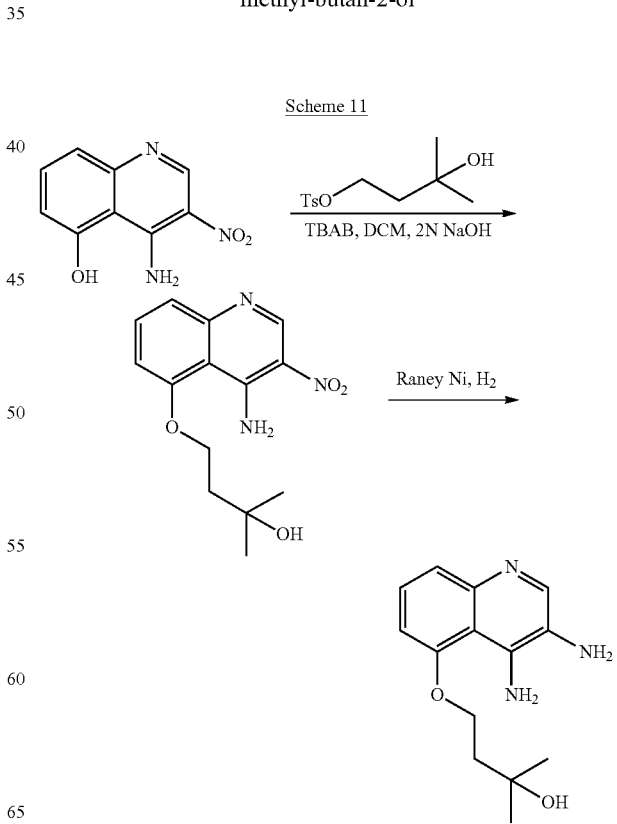

Scheme 11

Step 1: Synthesis of 4-[(4-amino-3-nitro-5-quinolyl)oxy]-2-methyl-butan-2-ol

To a solution of 4-amino-3-nitro-quinolin-5-ol (1.50 g, 7.31 mmol, 1.0 eq.), TBAB (2.36 g, 7.31 mmol, 1.0 eq.) and KI (405.04 mg, 2.44 mmol, 1.0 eq.) in NaOH (2 M, 3.66 mL, 3.0 eq.) was added a solution of (3-hydroxy-3-methyl-butyl) 4-methylbenzenesulfonate (5.67 g, 21.93 mmol, 3.0 eq.) in DCM (15.00 mL). The resulting mixture was stirred at 25° C. for 64 h. The reaction mixture was diluted with $H_2O$ (10 mL) and extracted with DCM (50 mL×2). The combined organic layers were washed with brine (10 mL), dried over anhydrous $Na_2SO_4$, filtered and concentrated under reduced pressure to give a residue. The residue was purified with column chromatography ($SiO_2$, DCM/MeOH=100/1 to 20/1). The desired product of 4-[(4-amino-3-nitro-5-quinolyl)oxy]-2-methyl-butan-2-ol (646.00 mg, 2.22 mmol, 30.34% yield) was obtained as a yellow solid. $^1$H NMR (400 MHz, $CDCl_3$) δ ppm: 9.59 (br s, 1H), 9.29 (s, 1H), 9.22 (br s, 1H), 7.63 (t, J=8.2 Hz, 1H), 7.54 (dd, J=8.4, 0.8 Hz, 1H), 6.92 (d, J=7.6 Hz, 1H), 4.38 (t, J=6.2 Hz, 2H), 2.14 (t, J=6.2 Hz, 2H), 1.41 (s, 6H); ES-LCMS m/z: 292.3 $[M+H]^+$.

Step 2: Synthesis of 4-[(3,4-diamino-5-quinolyl)oxy]-2-methyl-butan-2-ol

To a solution of 4-[(4-amino-3-nitro-5-quinolyl)oxy]-2-methyl-butan-2-ol (640.00 mg, 2.20 mmol, 1.0 eq.) in MeOH (150.00 mL) was added Raney-Ni (200.00 mg, 2.33 mmol, 1.1 eq.) under $N_2$. The suspension was degassed under vacuum and purged with $H_2$ Several times. The mixture was stirred under $H_2$ (15 psi) at 25° C. for 1 h. The reaction mixture was filtered. The filtrate was concentrated under reduced pressure to give a residue. The product was directly used in the next step without further purification. The desired crude product of 4-[(3,4-diamino-5-quinolyl)oxy]-2-methyl-butan-2-ol (570.00 mg, 2.18 mmol, 99.15% yield) was obtained as a black brown solid. H NMR (400 MHz, $CDCl_3$) δ ppm: 8.24 (s, 1H), 7.47 (d, J=8.4 Hz, 1H), 7.30 (t, J=8.0 Hz, 1H), 6.68 (d, J=7.6 Hz, 1H), 5.89 (br s, 2H), 4.28 (t, J=6.4 Hz, 2H), 2.11 (t, J=6.4 Hz, 2H), 1.36 (s, 6H); ES-LCMS m/z: 262.2 [M+H]+.

Intermediate 5: 5-Methoxy-N-methyl-3-nitro-quinolin-4-amine

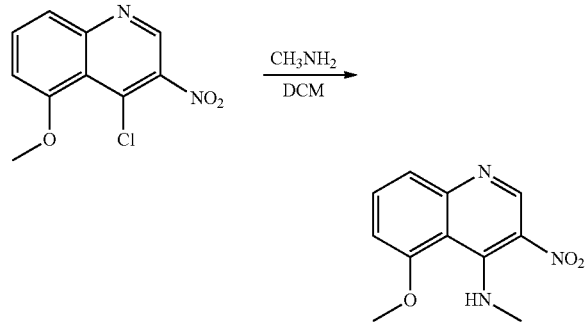

A solution of 4-chloro-5-methoxy-3-nitro-quinoline (1.00 g, 4.19 mmol, 1.0 eq.) in DCM (30.00 mL) was added to $MeNH_2$ (2 M in THF, 40.00 mL, 19.1 eq.). The mixture was stirred at 25° C. for 2 h. The mixture was concentrated to give a residue. The residue was purified with column chromatography ($SiO_2$, DCM/MeOH=50/1 to 20/1). The desired product of 5-methoxy-N-methyl-3-nitro-quinolin-4-amine (400.00 mg, 1.72 mmol, 40.93% yield) was obtained as a yellow solid. $^1$H NMR (400 MHz, $CDCl_3$) δ ppm: 9.03 (s, 1H), 8.79 (s, 1H), 7.62-7.60 (m, 2H), 6.94-6.92 (m, 1H), 4.09 (s, 3H), 2.94 (d, J=5.6 Hz, 3H); ES-LCMS m/z: 234.0 $[M+H]^+$.

Intermediate 6: 2-Ethoxyacetyl Chloride

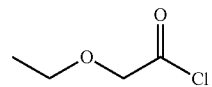

To a solution of 2-ethoxyacetic acid (1.00 g, 9.61 mmol, 909.09 μL, 1.0 eq.) and catalytic amount of DMF (10.00 mg, 136.82 mol, 10.53 μL, 0.01 eq.) in DCM (30.00 mL) was added oxalyl chloride (1.83 g, 14.41 mmol, 1.26 mL, 1.5 eq.) at 0° C. The resulting mixture was stirred at 25° C. for 2 h. The reaction mixture was concentrated under reduced pressure to remove the solvent. 2-Ethoxyacetyl chloride (900.00 mg, 7.34 mmol, 76.42% yield) was obtained as yellow oil.

Intermediate 7: 3-Methoxypropanoyl Chloride

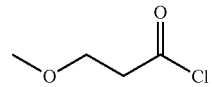

3-Methoxypropanoyl chloride was prepared in the same way as intermediate 6 using the corresponding starting material of 3-methoxypropanoic acid in 84.9% yield as yellow oil.

Intermediate 8: (3-Hydroxy-3-methyl-butyl) 4-methylbenzenesulfonate

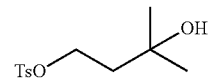 [SMILES: Cc1ccc(S(=O)(=O)OCCC(C)(C)O)cc1]

To a solution of 3-methylbutane-1,3-diol (10.00 g, 96.02 mmol, 10.20 mL, 1.0 eq.), $Et_3N$ (14.57 g, 144.03 mmol, 19.96 mL, 1.5 eq.) and DMAP (14.08 g, 115.22 mmol, 1.2 eq.) in DCM (200.00 mL) was added a solution of TsCl (17.39 g, 91.22 mmol, 0.95 eq) in DCM (100 mL) dropwise at 0° C. The resulting mixture was stirred at 0° C. for 1 h. The mixture was adjusted to pH=6 with citric acid. The organic layer was separated and washed with brine (100 mL), dried over anhydrous $Na_2SO_4$, filtered and concentrated in vacuo. (3-Hydroxy-3-methyl-butyl)4-methylbenzenesulfonate (19.80 g, 76.65 mmol, 79.83% yield) was obtained as a colorless oil. $^1$H NMR (400 MHz, $CDCl_3$) δ ppm: 7.80-7.78 (m, 2H), 7.34 (d, J=8.0 Hz, 2H), 4.22-4.19 (m, 2H), 2.45 (s, 3H), 1.87-1.84 (m, 2H), 1.21 (d, J=1.2 Hz, 6H); ES-LCMS m/z: 276.2 $[M+H_2O]^+$.

Intermediate 9: Isopentyl 4-methylbenzenesulfonate

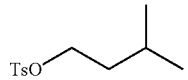

Isopentyl 4-methylbenzenesulfonate was prepared in a similar way as intermediate 8 using the corresponding starting material of 3-methylbutan-1-ol and purified with silica gel chromatography (PE/EA=20/1 to 10/1) to give 72.76% isolated yield as a yellow oil. $^1$H NMR (400 MHz, CDCl$_3$) δ ppm: 7.81-7.79 (m, 2H), 7.35 (d, J=8.0 Hz, 2H), 4.06 (t, J=6.6 Hz, 2H), 2.46 (s, 3H), 1.70-1.67 (m, 1H), 1.57-1.51 (m, 2H), 0.88-0.84 (m, 6H); ES-LCMS m/z: 264.9 [M+Na]$^+$.

Intermediate 10: 2-Isopropoxyethyl 4-methylbenzenesulfonate

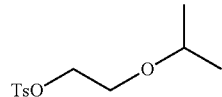 [SMILES: Cc1ccc(S(=O)(=O)OCCOC(C)C)cc1]

2-Isopropoxyethyl 4-methylbenzenesulfonate was prepared in a similar way as intermediate 8 using the corresponding starting material of 2-isopropoxyethanol in 81.44% yield as a colorless oil. $^1$H NMR (400 MHz, CDCl$_3$) δ ppm: 7.80 (d, J=8.0 Hz, 2H), 7.33 (d, J=8.4 Hz, 2H), 4.14-4.11 (m, 2H), 3.60-3.58 (m, 2H), 3.55-3.54 (m, 1H), 2.44 (s, 3H), 1.08 (d, J=6.0 Hz, 6H); ES-LCMS m/z: 259.3 [M+H]$^+$.

Intermediate 11: 3-Hydroxybutyl 4-methylbenzenesulfonate

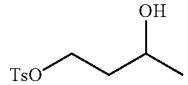 [SMILES: Cc1ccc(S(=O)(=O)OCCC(C)O)cc1]

3-Hydroxybutyl 4-methylbenzenesulfonate was prepared in a similar way as intermediate 8 using the corresponding starting material of butane-1,3-diol in 59.04% yield as a colorless oil. $^1$H NMR (400 MHz, CDCl$_3$) δ ppm: 7.83-7.79 (m, 2H), 7.37-7.34 (m, 2H), 4.26-4.22 (m, 1H), 4.15-4.12 (m, 1H), 3.98-3.93 (m, 1H), 2.46 (s, 3H), 1.85-1.81 (m, 1H), 1.74-1.68 (m, 1H), 1.20 (m, 3H); ES-LCMS m/z: 245.2 [M+H]$^+$.

Intermediate 12: Acetonyl 4-methylbenzenesulfonate

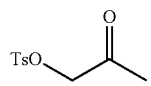

Acetonyl 4-methylbenzenesulfonate was prepared in a similar way as intermediate 8 using the corresponding starting material of 1-hydroxypropan-2-one in 25.31% yield as a colorless oil. $^1$H NMR (400 MHz, CDCl$_3$) δ ppm: 7.82 (d, J=8.4 Hz, 2H), 7.37 (d, J=8.4 Hz, 2H), 4.48 (s, 2H), 2.46 (s, 3H), 2.22 (s, 3H); ES-LCMS m/z: 229.2 [M+H]$^+$.

Other 2-aminoquinoline derivatives were prepared in a similar way as that described in Examples 1-7, and they are listed in Table 1. These compounds were prepared in HCl salt forms, and/or in the forms of neutral amine. A person skilled in the art can clearly understand and know that the other analogs could be prepared by the same or similar methods as described in Examples 1-7. These examples are not in any way to limit the analogs that can be made by applying the same or similar methods presented herein.

TABLE 1

2-Amino-Quinoline Derivatives Prepared

| Cmpd No. | Structure |
|---|---|
| 1 | 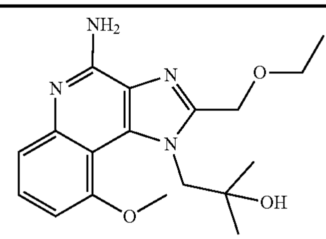 |
| 2 | 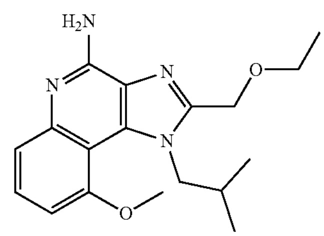 [SMILES: CCOCc1nc2c(N)nc3cccc(OC)c3c2n1CC(C)C] |
| 3 | 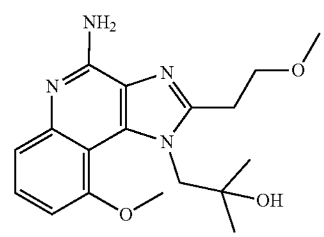 [SMILES: COCCc1nc2c(N)nc3cccc(OC)c3c2n1CC(C)(C)O] |
| 4 | 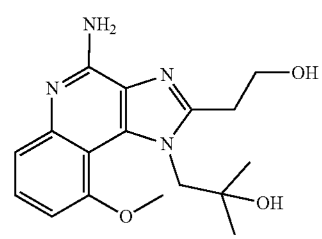 [SMILES: COc1cccc2nc(N)c3nc(CCO)n(CC(C)(C)O)c3c12] |
| 5 | 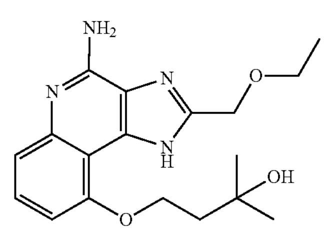 [SMILES: CCOCc1nc2c(N)nc3cccc(OCCC(C)(C)O)c3c2[nH]1] |

TABLE 1-continued

2-Amino-Quinoline Derivatives Prepared

| Cmpd No. | Structure |
|---|---|
| 6 | *(structure)* |
| 7 | *(structure)* |
| 8 | *(structure)* |
| 9 | *(structure)* |
| 10 | *(structure)* |
| 11 | *(structure)* |
| 12 | *(structure)* |
| 13 | *(structure)* |
| 14 | *(structure)* |
| 15 | *(structure)* |
| 16 | *(structure)* |

TABLE 1-continued

2-Amino-Quinoline Derivatives Prepared

| Cmpd No. | Structure |
|---|---|
| 17 | *chemical structure* |
| 18 | *chemical structure* |
| 19 | *chemical structure* |
| 20 | *chemical structure* |
| 21 | *chemical structure* |
| 22 | *chemical structure* |
| 23 | *chemical structure* |
| 24 | *chemical structure* |
| 25 | *chemical structure* |
| 26 | *chemical structure* |
| 27 | *chemical structure* |

TABLE 1-continued

2-Amino-Quinoline Derivatives Prepared

| Cmpd No. | Structure |
|---|---|
| 28 | [Structure: 4-amino imidazoquinoline with 2-(ethoxymethyl), 1-methyl, and 9-O-(pyrrolidin-3-yloxy) substituents] |
| 29 | [Structure: 4-amino imidazoquinoline with 2-(ethoxymethyl), 1-methyl, and 9-O-(piperidin-4-yloxy) substituents] |
| 30 | [Structure: 4-amino pyrazoloquinoline with 9-OH] |
| 31 | [Structure: 4-amino pyrazoloquinoline, 2-isopentyl, 9-OH] |
| 32 | [Structure: 4-amino pyrazoloquinoline, 2-isopentyl, 9-O-isopentyl] |
| 33 | [Structure: 4-amino pyrazoloquinoline, 2-butyl, 9-O-isobutyl] |
| 34 | [Structure: 4-amino imidazoquinoline with 2-(ethoxymethyl), 1-methyl, 9-O-(CH2)3-NH-C(=O)-C15H31] |
| 35 | [Structure: 4-amino imidazoquinoline with 2-(ethoxymethyl), 1-methyl, 9-O-(CH2)4-NH-C(=O)-C15H31] |
| 36 | [Structure: 4-amino imidazoquinoline with 2-(ethoxymethyl), 1-methyl, 9-O-(CH2)3-NH2] |
| 37 | [Structure: 4-amino imidazoquinoline with 2-(ethoxymethyl), 1-methyl, 9-O-isopropyl] |
| 38 | [Structure: 4-amino imidazoquinoline with 2-(ethoxymethyl), 1-methyl, 9-O-CH2-C(CH3)2-OH] |

TABLE 1-continued

2-Amino-Quinoline Derivatives Prepared

| Cmpd No. | Structure |
|---|---|
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |

The compound functionality was tested for some of the compounds prepared by stimulation and determination of cytokine production in PBMCs.

Human PBMCs were prepared from buffy coat obtained from healthy volunteer donor by Ficoll centrifugation and were adjusted to the final cell concentration to $1 \times 10^6$ cells/mL.

For evaluation of compound activities, $1 \times 10^5$ PBMCs were plated in a 96-well plate in 100 µl of RPMI 1640 complete medium (cat no. 31800-022, GIBCO by Life Technologies, Grand Island, NY, USA) supplemented with 10% fetal bovine serum, the tested compound was first dissolved in DMSO and further diluted in PBS and RPMI 1640 medium to the final concentration of 2004 (corresponding to 6.28 µg/mL), then 3-fold serially dilution was made in a 96-well round-bottom plate. 100 µl diluted compound was added to the same volume of $1 \times 10^5$ PBMCs plate and cultured for 20-22 hours at 37° C. in a humidified atmosphere of 5% $CO_2$. The supernatant was collected for human IFN-α, IL12(p70) and IL-6 analysis by ELISA assay according to the manufacturer's instructions (Mabtech AB, Sweden). Resiquimod was used as a positive control.

Table 2 below lists the testing results on the evaluation of cytokine production for most of the compounds prepared.

TABLE 2*
| Compound No. | Structure | M.W. | Production of IFNa on PBMC* | Production of IL-6 on PBMC* |
|---|---|---|---|---|
| 1 | 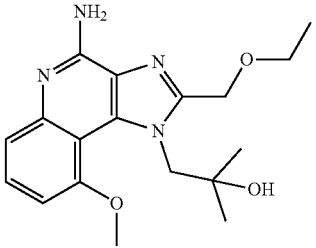 [SMILES: CCOCc1nc2c(N)nc3cccc(OC)c3c2n1CC(C)(C)O] | 344.41 | + | + |
| 2 | 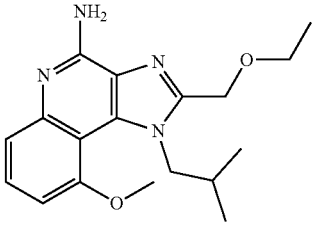 [SMILES: CCOCc1nc2c(N)nc3cccc(OC)c3c2n1CC(C)C] | 328.41 | + | + |
| 3 | 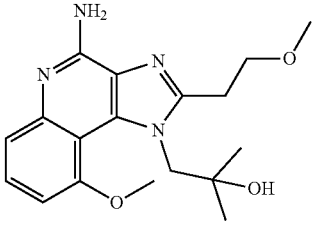 [SMILES: COCCc1nc2c(N)nc3cccc(OC)c3c2n1CC(C)(C)O] | 344.41 | − | − |
| 4 | 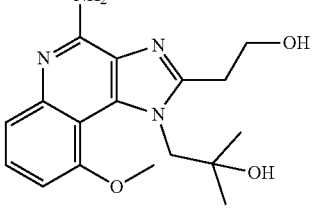 | 330.38 | − | − |
| 5 | 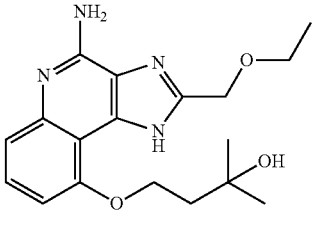 | 344.41 | + | + |
| 6 | 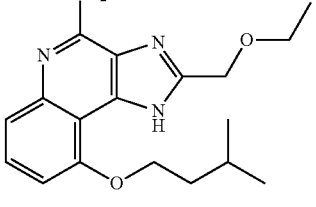 | 328.41 | N/A | + |

TABLE 2*-continued

| Compound No. | Structure | M.W. | Production of IFNa on PBMC* | Production of IL-6 on PBMC* |
|---|---|---|---|---|
| 7 | 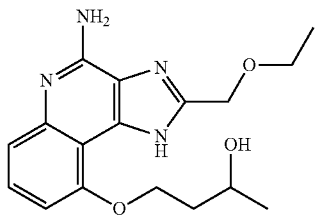 [SMILES: CCOCc1nc2c(N)nc3cccc(OCCC(C)O)c3c2[nH]1] | 330.38 | N/A | + |
| 8 | 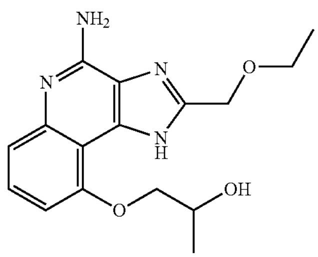 [SMILES: CCOCc1nc2c(N)nc3cccc(OCC(C)O)c3c2[nH]1] | 316.35 | + | + |
| 9 | 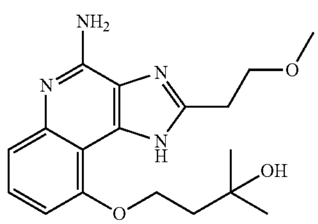 [SMILES: COCCc1nc2c(N)nc3cccc(OCCC(C)(C)O)c3c2[nH]1] | 344.41 | N/A | + |
| 10 | 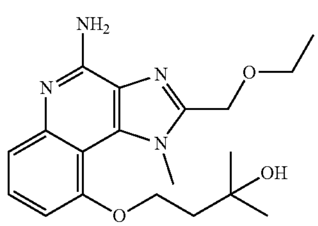 [SMILES: CCOCc1nc2c(N)nc3cccc(OCCC(C)(C)O)c3c2n1C] | 358.43 | N/A | + |
| 11 | 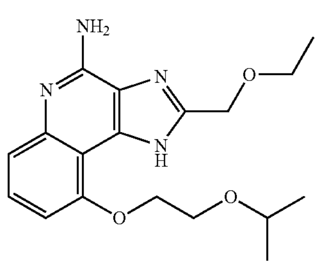 [SMILES: CCOCc1nc2c(N)nc3cccc(OCCOC(C)C)c3c2[nH]1] | 344.41 | + | + |
| 12 | 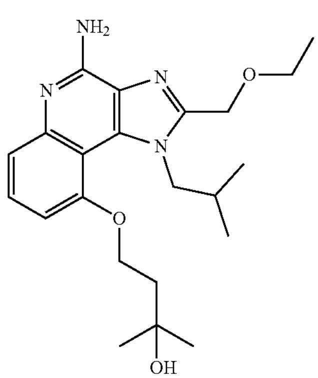 [SMILES: CCOCc1nc2c(N)nc3cccc(OCCC(C)(C)O)c3c2n1CC(C)C] | 400.51 | + | + |

TABLE 2*-continued

| Compound No. | Structure | M.W. | Production of IFNa on PBMC* | Production of IL-6 on PBMC* |
|---|---|---|---|---|
| 13 | 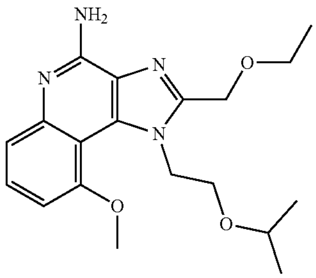 [SMILES: CCOCc1nc2c(N)nc3cccc(OC)c3c2n1CCOC(C)C] | 358.43 | + | + |
| 14 | 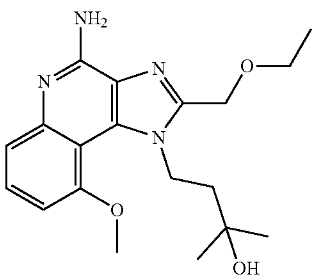 [SMILES: CCOCc1nc2c(N)nc3cccc(OC)c3c2n1CCC(C)(C)O] | 358.43 | + | + |
| 15 | 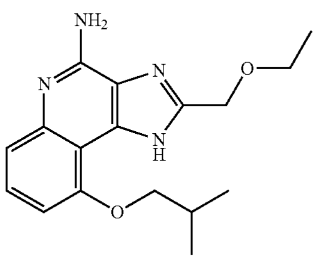 | 314.38 | + | + |
| 16 | 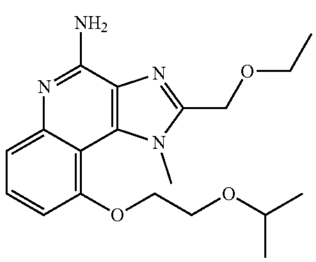 [SMILES: CCOCc1nc2c(N)nc3cccc(OCCOC(C)C)c3c2n1C] | 358.43 | + | + |
| 17 | 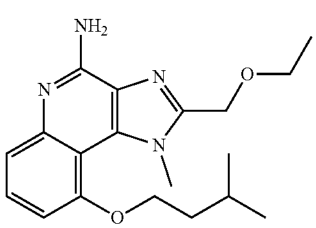 [SMILES: CCOCc1nc2c(N)nc3cccc(OCCC(C)C)c3c2n1C] | 342.44 | + | + |
| 18 | 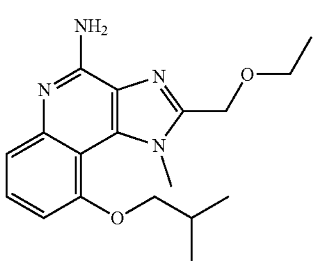 [SMILES: CCOCc1nc2c(N)nc3cccc(OCC(C)C)c3c2n1C] | 328.41 | + | + |

TABLE 2*-continued

| Compound No. | Structure | M.W. | Production of IFNa on PBMC* | Production of IL-6 on PBMC* |
|---|---|---|---|---|
| 19 | 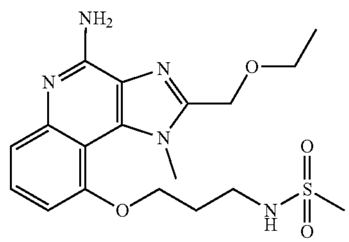 [SMILES: CCOCc1nc2c(N)nc3cccc(OCCCNS(C)(=O)=O)c3c2n1C] | 407.49 | + | + |
| 20 | 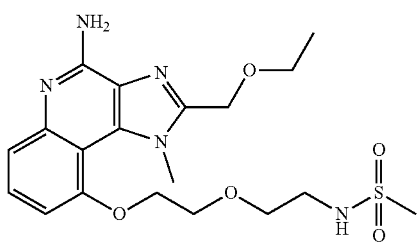 [SMILES: CCOCc1nc2c(N)nc3cccc(OCCOCCNS(C)(=O)=O)c3c2n1C] | 437.51 | + | + |
| 22 | 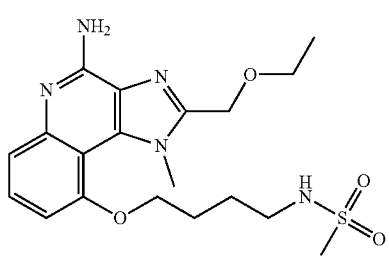 [SMILES: CCOCc1nc2c(N)nc3cccc(OCCCCNS(C)(=O)=O)c3c2n1C] | 421.51 | + | + |
| 23 | 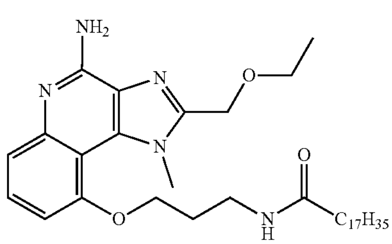 | 595.86 | + | + |
| 24 | 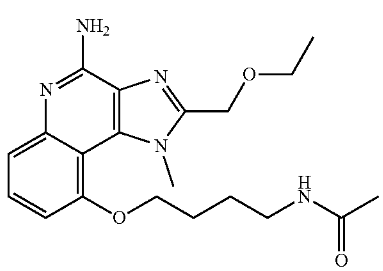 [SMILES: CCOCc1nc2c(N)nc3cccc(OCCCCNC(C)=O)c3c2n1C] | 385.46 | + | + |
| 25 | 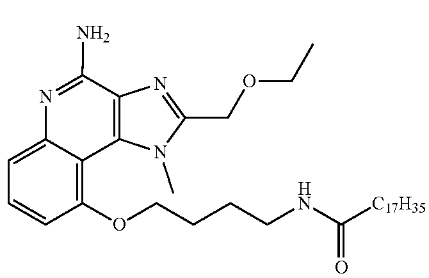 | 609.89 | + | + |

TABLE 2*-continued

| Compound No. | Structure | M.W. | Production of IFNa on PBMC* | Production of IL-6 on PBMC* |
|---|---|---|---|---|
| 27 | 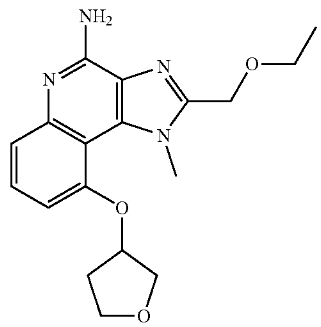 [SMILES: CCOCc1nc2c(N)nc3cccc(OC4CCOC4)c3c2n1C] | 342.39 | + | + |
| 28 | 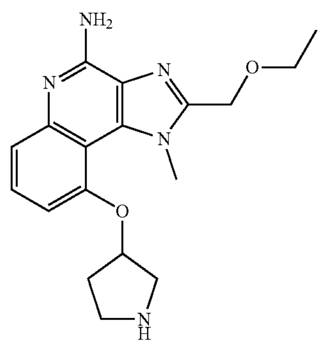 [SMILES: CCOCc1nc2c(N)nc3cccc(OC4CCNC4)c3c2n1C] | 341.41 | + | + |
| 29 | 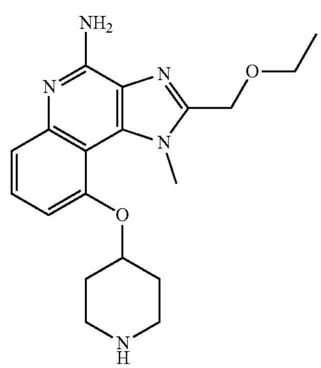 [SMILES: CCOCc1nc2c(N)nc3cccc(OC4CCNCC4)c3c2n1C] | 355.43 | + | + |
| 31 | 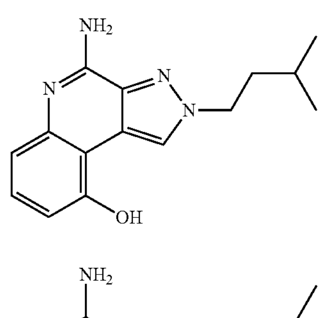 | 270.33 | − | − |
| 32 | 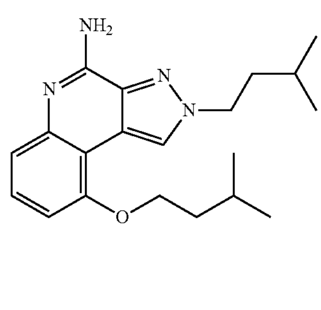 [SMILES: CC(C)CCOc1cccc2nc(N)c3nn(CCC(C)C)cc3c12] | 340.46 | − | − |

TABLE 2*-continued

| Compound No. | Structure | M.W. | Production of IFNa on PBMC* | Production of IL-6 on PBMC* |
|---|---|---|---|---|
| 33 | 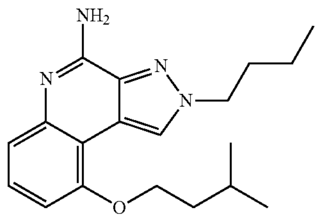 | 326.44 | − | + |
| 34 | 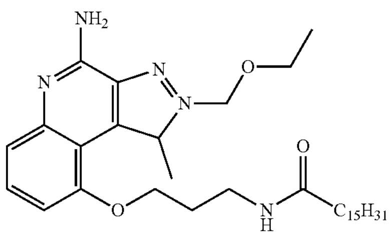 | 567.81 | + | + |
| 35 | 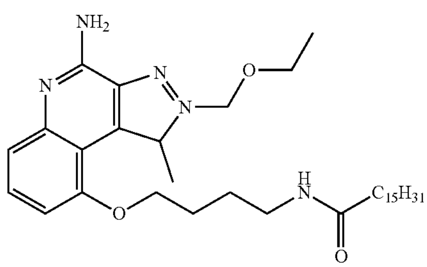 | 581.83 | + | + |
| 36 | 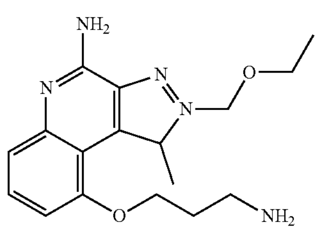 | 329.40 | + | + |
| 37 | 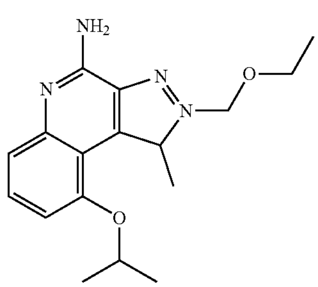 | 314.38 | + | + |
| 38 | 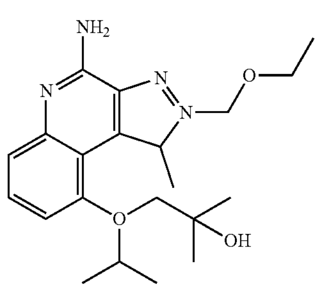 | 344.41 | + | + |

TABLE 2*-continued

| Compound No. | Structure | M.W. | Production of IFNa on PBMC* | Production of IL-6 on PBMC* |
|---|---|---|---|---|
| 39 | 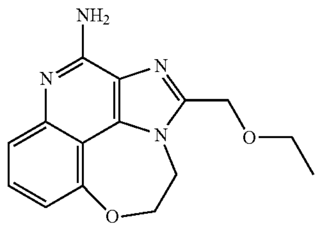 [SMILES: CCOCc1nc2c(N)nc3cccc4c3c2n1CCO4] | 284.31 | + | + |
| 40 | 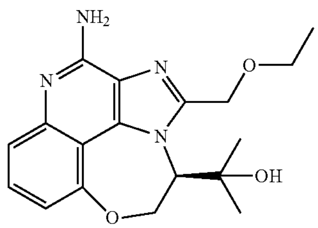 [SMILES: CCOCc1nc2c(N)nc3cccc4c3c2n1[C@@H](C(C)(C)O)CO4] | 342.39 | N/A | − |
| 41 | 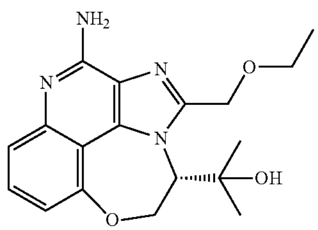 [SMILES: CCOCc1nc2c(N)nc3cccc4c3c2n1[C@H](C(C)(C)O)CO4] | 342.39 | N/A | + |
| 42 | 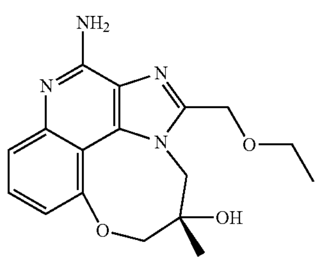 [SMILES: CCOCc1nc2c(N)nc3cccc4c3c2n1C[C@](C)(O)CO4] | 328.37 | + | + |
| 43 | 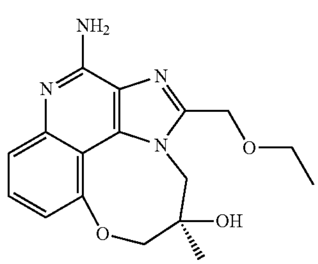 [SMILES: CCOCc1nc2c(N)nc3cccc4c3c2n1C[C@@](C)(O)CO4] | 328.37 | N/A | − |
| 44 | 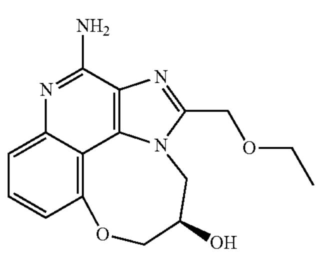 [SMILES: CCOCc1nc2c(N)nc3cccc4c3c2n1C[C@@H](O)CO4] | 314.34 | N/A | − |

TABLE 2*-continued

| Compound No. | Structure | M.W. | Production of IFNa on PBMC* | Production of IL-6 on PBMC* |
|---|---|---|---|---|
| 45 | 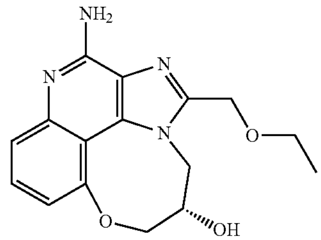 [SMILES: CCOCc1nc2c(N)nc3cccc4c3c2n1C[C@H](O)CO4] | 314.34 | N/A | + |
| 46 | 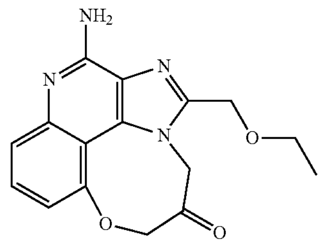 [SMILES: CCOCc1nc2c(N)nc3cccc4c3c2n1CC(=O)CO4] | 312.32 | N/A | + |

*Note 1:
All the compounds were tested at concentration of 10 uM.
Note 2:
"+" means that there was production of IFNa or IL-6 on PBMC; while "-"means that noproduction of IFNa or IL-6 on PBMC was detected.

What is claimed is:

1. A compound represented by a formula:

or a salt thereof;
wherein a dashed line represents the presence or absence of a bond;
$A^1$ is $CR^1$, $NR^{1A}$, or N;
$A^2$ is $CR^2$;
$B^1$ is $CR^5$ or N;
$B^2$ is $CR^6$ or N;
$B^3$ is $CR^7$ or N;
$R^1$ and $R^2$ are independently F, Cl, Br, I, $NO_2$, CN, $R^a$, —$OR^a$, —$NR^aR^b$, —$NHCOR^a$, —$NHSO_2R^a$, —$OCOR^a$, or —$SO_2R^a$;
X is a bond, O, $NR^a$, —CO—, —SO—, or —$SO_2$—, —$CONR^a$, hydrocarbyl, and $R^3$ is H or $C_{1-30}$ organyl; or X—$R^3$ is F or Cl;
$R^{1A}$, $R^4$, $R^a$, and $R^b$ are independently H or $C_{1-30}$ organyl;
$R^5$, $R^6$, and $R^7$ are independently F, Cl, Br, I, $NO_2$, —$CO_2R^a$, —$CONR^aR^b$, CN, $R^a$, —$OR^a$, —$NR^aR^b$, —$NHCOR^a$, —$NHSO_2R^a$, —$OCOR^a$, —$SO_2R^a$, —$SO_2NHR^a$, or —$X^1$—$(C_mH_{2m}O_{0-1})$—Z—$(C_nH_{2n+1})$, —$(C_mH_{2m}O_{0-1})$—Z—$(C_nH_{2n+1})$, wherein $R^5$ and $R^6$ or $R^6$ and $R^7$ can be optionally linked to form a ring;
wherein $X^1$ is a bond, O, $NR^a$, —CO—, —SO—, or —$SO_2$—;
Z is a bond, O, $NHSO_2$, or NHCO;
m is 0, 1, 2, 3, 4, 5, 6, 7, 8, 9, or 10; and
n is 1, 2, 3, 4, 5, 6, 7, 8, 9, 10, 11, 12, 13, 14, 15, 16, 17, 18, 19, 20, 21, 22, or 23.

2. The compound of claim 1, further represented by a formula:

or a salt thereof;
wherein $R^4$ is H, $C_{1-30}$ non-aromatic organyl, or $C_{1-30}$ aromatic organyl containing an aromatic group that is not directly attached to the N atom.

3. The compound of claim 1 wherein $R^1$ or $R^{1A}$ is $C_{1-12}$ optionally substituted alkyl.

4. The compound of claim 3, wherein $R^1$ or $R^{1A}$ is —$C_rH_{2r+1}O$, or an ester thereof, wherein r is 1, 2, 3, 4, 5, 6, 7, 8, 9, or 10.

5. The compound of claim 4, wherein $R^1$ or $R^{1A}$ is —$C_3H_7O$.

6. The compound of claim 5, wherein $R^1$ or $R^{1A}$ is —$CH_2OCH_2CH_3$.

7. The compound of claim 1, wherein $R^2$ is H or $C_{1-12}$ optionally substituted alkyl.

8. The compound of claim 7, wherein $R^2$ is $C_{1-6}$ alkyl, or —$C_yH_{2y+1}O$ or an ester thereof, wherein y is 1, 2, 3, 4, 5, 6, 7, 8, 9, or 10.

9. The compound of claim 8, wherein $R^2$ is $CH_3$.

10. The compound of claim 7, wherein $R^2$ is H.

11. The compound of claim 7, wherein $R^2$ is $C_4H_9$.

12. The compound of claim 1, wherein $R^3$ is $C_{1-30}$ optionally substituted alkyl.

13. The compound of claim 12, wherein $R^3$ is $C_{1-10}$ alkyl, or $-C_wH_{2w+1}O$ or an ester thereof, wherein w is 1, 2, 3, 4, 5, 6, 7, 8, 9, or 10.

14. The compound of claim 1, wherein $R^3$ is $-(C_tH_{2t}O_{0-1})-$Ht, wherein t is 0, 1, 2, 3, 4, 5, 6, 7, 8, 9, or 10, and Ht is optionally substituted $C_{3-6}$ heterocyclyl.

15. The compound of claim 1, wherein $R^3$ is $-(C_uH_{2u}O_{0-1})-Z-(C_vH_{2v+1})$, wherein Z is a bond, O, $NHSO_2$, or NHCO, u is 0, 1, 2, 3, 4, 5, or 6, and v is 1, 2, 3, 4, 5, 6, 7, 8, 9, 10, 11, 12, 13, 14, 15, 16, 17, 18, 19, 20, 21, 22, or 23.

16. The compound of claim 1, wherein $R^3$ is $-(C_uH_{2u}O_{0-1})-NR^aR^b$, and u is 1, 2, 3, 4, 5, or 6, wherein $R^a$ and $R^b$ are independently H or $C_{1-6}$ alkyl.

17. The compound of claim 13, wherein $R^3$ is $C_5H_{11}O$.

18. The compound of claim 17, wherein $R^3$ is $-CH_2-CH_2-C(CH_3)_2OH$.

19. The compound of claim 16, wherein $R^3$ is $-CH_2-CH_2-CH_2-NH_2$.

20. The compound of claim 1, wherein $R^4$ is H or $C_{1-6}$ alkyl.

21. The compound of claim 20, wherein $R^4$ is H.

22. The compound of claim 1, wherein $R^5$ is $R^a$, F, Cl, $-CO_2R^a$, $-CONR^aR^b$, CN, $-OR^a$, $-NR^aR^b$, $-OCOR^a$, or $-SO_2R^a$, $-SO_2NHR^a$, wherein $R^a$ and $R^b$ are independently H or $C_{1-6}$ alkyl.

23. The compound of claim 22, wherein $R^5$ is H.

24. The compound of claim 1, wherein $R^5$ is $-(C_mH_{2m}O_{0-1})-Z-(C_nH_{2n+1})$, wherein Z is a bond, O, $NHSO_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, or 23.

25. The compound of claim 1, wherein $R^6$ is $R^a$, F, Cl, $-CO_2R^a$, $-CONR^aR^b$, CN, $-OR^a$, $-NR^aR^b$, $-OCOR^a$, or $-SO_2R^a$, $-SO_2NHR^a$, wherein $R^a$ and $R^b$ are independently H or $C_{1-6}$ alkyl.

26. The compound of claim 25, wherein $R^6$ is H.

27. The compound of claim 1, wherein $R^6$ is $-(C_mH_{2m}O_{0-1})-Z-(C_nH_{2n+1})$, wherein Z is a bond, O, $NHSO_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, or 23.

28. The compound of claim 1, wherein $R^7$ is $R^a$, F, Cl, $-CO_2R^a$, $-CONR^aR^b$, CN, $-OR^a$, $-NR^aR^b$, $-OCOR^a$, or $-SO_2R^a$, $-SO_2NHR^a$, wherein $R^a$ and $R^b$ are independently H or $C_{1-6}$ alkyl.

29. The compound of claim 28, wherein $R^7$ is H.

30. The compound of claim 1, wherein $R^7$ is $-(C_mH_{2m}O_{0-1})-Z-(C_nH_{2n+1})$, wherein Z is a bond, O, $NHSO_2$, or NHCO, m is 0, 1, 2, 3, 4, 5, 6, 7, 8, 9, or 10, and n is 1, 2, 3, 4, 5, 6, 7, 8, 9, 10, 11, 12, 13, 14, 15, 16, 17, 18, 19, 20, 21, 22, or 23.

31. The compound of claim 1, $R^3$ is H, OH, or $CH_3$.

32. The compound of claim 31, wherein $R^8$ is OH.

33. The compound of claim 31, wherein $R^8$ is H.

34. A compound, which is:

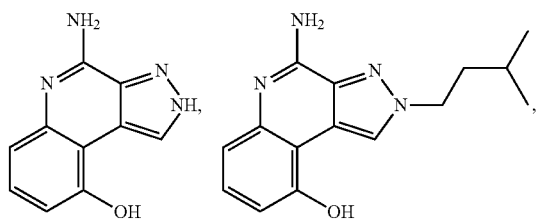

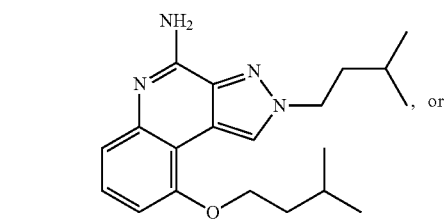

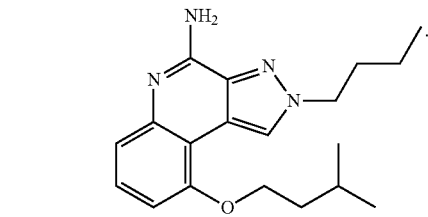

35. The compound of claim 1 which is optionally substituted 9-methoxy-2H-pyrazolo[3,4-c]quinolin-4-amine.

36. The compound of claim 1 which is optionally substituted 4-amino-2H-pyrazolo[3,4-c]quinolin-9-ol or a salt thereof; optionally substituted 4-amino-2-isopentyl-2H-pyrazolo[3,4-c]quinolin-9-ol or a salt thereof; optionally substituted 2-isopentyl-9-(isopentyloxy)-2H-pyrazolo[3,4-c]quinolin-4-amine or a salt thereof; or optionally substituted 2-butyl-9-(isopentyloxy)-2H-pyrazolo[3,4-c]quinolin-4-amine or a salt thereof.

37. The compound of claim 1, which is represented by a formula:

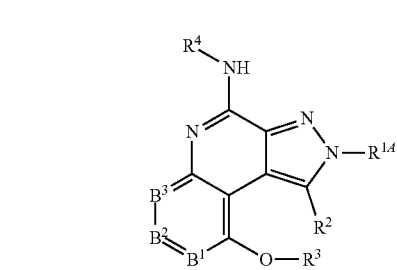

or a salt thereof.

38. The compound of claim 1, which is represented by a formula:

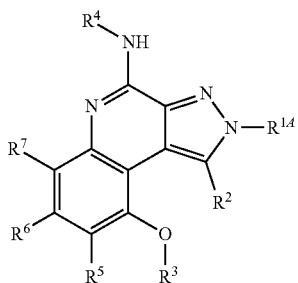

or a salt thereof.

39. The compound of claim 1, which is represented by a formula:

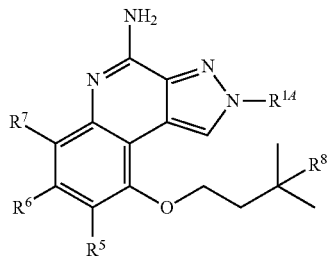

or a salt thereof.

40. The compound of claim 1, which is represented by a formula:

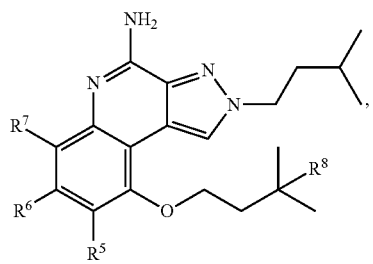

or a salt thereof.

41. A method of treating a viral infection, comprising administering the compound of claim 1, to a mammal in need thereof.

42. The method of claim 41, wherein the viral infection comprises HCV infection.

43. A dosage form suitable for administration to a mammal, comprising the compound of claim 1.

44. A method, comprising administering the compound of claim 1, to a mammal.

* * * * *